US011225526B2

(12) United States Patent
Larsen et al.

(10) Patent No.: US 11,225,526 B2
(45) Date of Patent: Jan. 18, 2022

(54) ANTIBODIES TO MASP-2

(71) Applicant: Helion Biotech ApS, Copenhagen N (DK)

(72) Inventors: Flemming Larsen, Copenhagen O (DK); Ulla Wahlers, Glostrup (DK)

(73) Assignee: Helion Biotech ApS, Copenhagen (DK)

( * ) Notice: Subject to any disclaimer, the term of this patent is extended or adjusted under 35 U.S.C. 154(b) by 0 days.

(21) Appl. No.: 17/181,983

(22) Filed: Feb. 22, 2021

(65) Prior Publication Data

US 2021/0261688 A1 Aug. 26, 2021

Related U.S. Application Data

(62) Division of application No. 16/209,255, filed on Dec. 4, 2018, now Pat. No. 11,008,404, which is a division of application No. 14/745,247, filed on Jun. 19, 2015, now Pat. No. 10,189,909, which is a division of application No. 10/556,509, filed as application No. PCT/DK2004/000338 on May 12, 2004, now Pat. No. 9,096,676.

(30) Foreign Application Priority Data

May 12, 2003 (DK) .......................... PA 2003 00716

(51) Int. Cl.
C07K 16/40 (2006.01)
(52) U.S. Cl.
CPC .......... C07K 16/40 (2013.01); *C07K 2317/24* (2013.01); *C07K 2317/54* (2013.01); *C07K 2317/55* (2013.01); *C07K 2317/622* (2013.01)
(58) Field of Classification Search
None
See application file for complete search history.

(56) References Cited

U.S. PATENT DOCUMENTS

| | | |
|---|---|---|
| 4,331,647 A | 5/1982 | Goldenberg |
| 4,394,370 A | 7/1983 | Jefferies |
| 4,526,909 A | 7/1985 | Urist |
| 4,563,489 A | 1/1986 | Urist |
| 4,816,567 A | 3/1989 | Cabilly et al. |
| 4,946,778 A | 8/1990 | Ladner et al. |
| 4,975,527 A | 12/1990 | Koezuka et al. |
| 5,211,657 A | 5/1993 | Yamada et al. |
| 5,223,409 A | 6/1993 | Ladner et al. |
| 5,403,484 A | 4/1995 | Ladner et al. |
| 5,552,157 A | 9/1996 | Yagi et al. |
| 5,565,213 A | 10/1996 | Nakamori et al. |
| 5,567,434 A | 10/1996 | Szoka, Jr. |
| 5,571,698 A | 11/1996 | Ladner et al. |
| 5,610,288 A | 3/1997 | Rubenstein |
| 5,693,762 A | 12/1997 | Queen et al. |
| 5,718,709 A | 2/1998 | Considine et al. |
| 5,738,868 A | 4/1998 | Shinkarenko |
| 5,739,119 A | 4/1998 | Galli et al. |
| 5,741,516 A | 4/1998 | Webb et al. |
| 5,759,829 A | 6/1998 | Shewmaker et al. |
| 5,789,573 A | 8/1998 | Baker et al. |
| 5,795,587 A | 8/1998 | Gao et al. |
| 5,801,154 A | 9/1998 | Baracchini et al. |
| 6,008,017 A | 12/1999 | Arleth et al. |
| 6,235,494 B1 | 5/2001 | Hugli |
| 6,297,024 B1 | 10/2001 | Hugli et al. |
| 6,407,213 B1 | 6/2002 | Carter et al. |
| 6,420,432 B2 | 7/2002 | Demopulos et al. |
| 6,492,332 B1 | 12/2002 | Demopulos et al. |
| 6,562,784 B1 | 5/2003 | Thiel et al. |
| 6,645,168 B2 | 11/2003 | Demopulos et al. |
| 6,649,592 B1 | 11/2003 | Larson |
| 6,846,649 B1 | 1/2005 | Thiel et al. |
| 6,969,601 B2 | 11/2005 | Jensenius et al. |
| 7,060,267 B2 | 6/2006 | Jensenius et al. |
| 7,083,786 B2 | 8/2006 | Jensenius et al. |
| 7,112,414 B2 | 9/2006 | Jensenius et al. |
| 7,728,114 B2 | 6/2010 | Mach et al. |
| 2002/0019369 A1 | 2/2002 | Li et al. |
| 2002/0082208 A1 | 6/2002 | Jensenius et al. |
| 2002/0082209 A1 | 6/2002 | Jensenius et al. |
| 2002/0094332 A1 | 7/2002 | Bell |
| 2002/0187526 A1 | 12/2002 | Ruben et al. |

(Continued)

FOREIGN PATENT DOCUMENTS

| | | |
|---|---|---|
| EP | 0 321 201 B1 | 12/1994 |
| EP | 1 033 401 A2 | 9/2000 |

(Continued)

OTHER PUBLICATIONS

Weman et al., Ann Thorac Surg. Sep. 2000;70(3):807-12. (Year: 2000).*
Guan et al., J Cardiovasc Pharmacol, May 2003;41: 699-705. (Year: 2003).*
Cseh et al., International Immunopharmacology 318 (2002) at 1253-1254, Abstract#78. (Year: 2002).*
Cseh, S., et al., "Characterization of the Interaction Between L-Ficolon/P35 and Mannan-binding lectin-asociated Serine Proteases-1 and -2," *Journal of Immunology* 169:5735-5743 (2002).
Holmskov, U., et al., "Collectins and Ficolins: Humoral Lectins of the Innate Immune Defence," *Annu Rev Immunol* 21:547-78 (2003).
Matsushita, M., et al., "The Role of Ficolins in Innate Immunity," *Immunobiol* 205:490-497 (2002).

(Continued)

*Primary Examiner* — Zachary S Skelding
(74) *Attorney, Agent, or Firm* — Tineka J. Quinton, Esq.

(57) ABSTRACT

The invention relates to antibodies to MASP-2 and functional equivalents thereof. In particular, the invention relates to MASP-2 antibodies capable of inhibiting the function of MASP-2. The invention furthermore discloses MASP-2 epitopes, wherein antibodies recognising said epitopes are in particularly useful for inhibiting MASP-2 activity. The invention also relates to methods of producing said antibodies, methods of inhibiting MASP-2 activity as well as to pharmaceutical compositions comprising the MASP-2 antibodies.

5 Claims, 11 Drawing Sheets

Specification includes a Sequence Listing.

(56) References Cited

U.S. PATENT DOCUMENTS

| | | |
|---|---|---|
| 2003/0049260 A1 | 3/2003 | Bell |
| 2003/0186419 A1 | 10/2003 | Jensenius |
| 2003/0207309 A1 | 11/2003 | Hageman |
| 2003/0235582 A1 | 12/2003 | Singh et al. |
| 2004/0038297 A1 | 2/2004 | Jensenius et al. |
| 2004/0081619 A1 | 4/2004 | Bell |
| 2004/0219147 A1 | 11/2004 | Bell |
| 2004/0259771 A1 | 12/2004 | Stahl et al. |
| 2005/0004031 A1 | 1/2005 | Subasinghe et al. |
| 2005/0222027 A1 | 10/2005 | Chiang et al. |
| 2006/0002937 A1 | 1/2006 | Schwaeble et al. |
| 2006/0018896 A1 | 1/2006 | Schwaeble et al. |
| 2006/0275764 A1 | 12/2006 | Thiel et al. |
| 2007/0009528 A1 | 1/2007 | Larsen et al. |
| 2007/0031420 A1 | 2/2007 | Jensenius et al. |
| 2008/0171014 A1 | 7/2008 | Wu et al. |

FOREIGN PATENT DOCUMENTS

| | | |
|---|---|---|
| JP | 7-238100 A | 9/1995 |
| JP | 11-123085 | 11/1999 |
| WO | WO 1995/023161 A1 | 8/1995 |
| WO | WO 2000/022160 | 4/2000 |
| WO | WO 2000/035483 A1 | 6/2000 |
| WO | WO 2000/055180 | 9/2000 |
| WO | WO 2001/007067 A2 | 2/2001 |
| WO | WO 2001/10902 A2 | 2/2001 |
| WO | WO 2001/012212 A1 | 2/2001 |
| WO | WO 2001/040451 A2 | 7/2001 |
| WO | WO 2002/006460 A2 | 1/2002 |
| WO | WO 2003/009803 A2 | 2/2003 |
| WO | WO 2003/061765 A1 | 7/2003 |
| WO | WO 2003/063799 A2 | 8/2003 |
| WO | WO 2004/009664 A2 | 1/2004 |
| WO | WO 2004/022096 A1 | 3/2004 |
| WO | WO 2004/050907 A2 | 6/2004 |
| WO | WO 2004/075837 A2 | 9/2004 |
| WO | WO 2004/106384 A1 | 12/2004 |
| WO | WO 2005/002627 A2 | 1/2005 |
| WO | WO 2005/024013 A1 | 3/2005 |
| WO | WO 2005/120222 A2 | 12/2005 |
| WO | WO 2005/123128 A2 | 12/2005 |
| WO | WO 2005/123776 A1 | 12/2005 |

OTHER PUBLICATIONS

Jack, D.L., et al., "Mannose-binding lectin: targeting the micobiol world for complement attack and opsonophagocytosis," *Immunological Reviews* 180:86-99 (2001).
Turner, M.W., et al., "The role of mannose-binding lectin in health and disease," *Molecular Immunology* 40:423-429 (2003).
Madalinski, K., et al., "The lectin pathway of vomplement activation. The role of complement in pathological processes and possible strategies of its activity modulation in therapy of some diseases," *Centr Eur J Immunol* 28(2):67-73 (2003).
Chen, C.B., et al., "Stoichiometry of Complexes Between MannoseBinding Protein and Its Associated Serine Proteases," *Journal of Biological Chemistry* 276(28):25894-25902, (2001).
Feinberg, H., et al., "Crystal Structure of the CUB1-EGF-CUB2 Region of Mannose-Binding Protein Associated Serine Protease-2," *EMBO Journal* 22(10):2348-2359, (2003).
Ji, H., et al., "Arthritis Critically Dependent on Innate Immune System Players," *Immunity* 16(2):157-168, (2002).
Lynch, N.J., et al., "L-Ficolin Specifically Binds to Lipoteichoic Acid, a Cell Wall Constituent of Gram-Positive Bacteria, and Activates the Lectin Pathway of Complement," *Journal of Immunology* 172(2):1198-1202, (2004).
Stover, C.M., et al., "Two Constituents of the Initiation Complex of the Mannan Binding Lectin Activation Pathway of Complement Are Encoded by a Single Structural Gene," *Journal of Immunology* 162(6):3481-3490, (1999).

Stover, C.M., et al., "The Rat and Mouse Homologues of MASP-2 and MAp19, Components of the Lectin Activation Pathway of Complement," *Journal of Immunology* 163(12):6848-6859, (1999).
Thiel, S., et al., "A Second Serine Protease Associated With Mannan-Binding Lectin That Activates Complement," *Nature* 386(6624):506-510, (1997).
Thiel, S., et al., "Interaction of C1q and Mannan-Binding Lectin (MBL) With C1r, C1s, MBL-Associated Serine Proteases 1 and 2, and the MBL-Associated Protein MAp19," *Journal of Immunology* 165(2):878-887, (2000).
Vorup-Jensen, T., et al., "Distinct Pathways of Mannan-Binding Lectin (MBL) and C1-Complex Autoactivation Revealed by Reconstitution of MBL With Recombinant MBL-Associated Serine Protease-2," *Journal of Immunology* 165(4):2093-2100, (2000).
Gupta-Bansal, R., et al., "Inhibition of Complement Alternative Pathway Function With Anti-Properdin Monoclonal Antibodies," *Molecular Immunology* 37(5):191-201, (2000).
Thielens, N.M., et al., "Interaction Properties of Human Mannan-Binding Lectin (MBL)-Associated Serine Proteases-I and-2, MBL-Associated Protein 19, and MBL," *Journal of Immunology* 166(8):5068-5077, (2001).
Huber-Lang, M.S., et al., "Complement-Induced Impairment of Innate Immunity During Sepsis," *Journal of Immunology* 169(6):3223-3231, (2002).
Matsushita, M., et al., "Cutting Edge: Complement-Activating Complex of Ficolin and Mannose-Binding Lectin-Associated Serine Protease," *Journal of Immunology* 164(5):2281-2284, (2000).
Matsushita, M., et al., "Proteolytic Activites of Two Types of Mannose Binding Lectin-Associated Serine Protease," *Journal of Immunology* 165(5):2637-2642, (2000).
Amsterdam, E.A., et al., "Limitation of Reperfusion Injury by a Monoclonal Antibody to C5a During Myocardial Infarction in Pigs," *American Journal of Physiology* 268(1 Pt 2):H448-H457, (1995).
Gralinski, M.R., et al., "Selective Inhibition of the Alternative Complement Pathway by sCR1 [desLHR-A] Protects the Rabbit Isolated Heart From Human Complement-Mediated Damage," *Immunopharmacology* 34(2-3):79-88, (1996).
Molina, H., "Update on Complement in the Pathogenesis of Systemic Lupus Erythematosus," *Current Opinion in Rheumatology* 14(5):492-497, (2002).
Fitch, J.C.K., et al., "Pharmacology and Biological Efficacy of a Recombinant, Humanized, Single-Chain Antibody C5 Complement Inhibitor in Patients Undergoing Coronary Artery Bypass Graft Surgery With Cardiopulmonary Bypass," *Circulation* 100(25):2499-2506, (1999).
Wang, H., et al., "Complement Inhibition With an Anti-C5 Monoclonal Antibody Prevents Hyperacute Rejection in a Xenograft Heart Transplantation Model," *Transplantation* 68(11): 1643-1651, (1999).
Wang, Y., et al., "Anti-C5 Monoclonal Antibody Therapy Prevents CollagenInduced Arthritis and Ameliorates Established Disease," *Proceedings of the National Academy of Sciences of the United States of America* 92(19):8955-8959, (1995).
Haeger, M., "The Role of Complement in Pregnancy-Induced Hypertensive Disease," *International Journal of Gynecology and Obstetrics* 43(2):113-127, (1993).
D'Cruz, O.J., et al., "Recombinant Soluble Human Complement Receptor Type 1 Inhibits Antisperm Antibody- and Neutrophil-Mediated Injury to Human Sperm," *Biology of Reproduction* 54(6):1217-1228, (1996).
Xu, C., et al., "A Critical Role for Murine Complement Regulator Crry in Fetomatemal Tolerance," *Science* 287(5452):498-501, (2000).
Ohsawa, I., et al., "Cryoprecipitate of Patients With Cryoglobulinemic Glomerulonephritis Contains Molecules of the Lectin Complement Pathway," *Clinical Immunology* 101(1):59-66, (2001).
Endo, M., et al., "Regulation of in Situ Complement Activation Via the Lectin Pathway in Patients With IgA Nephropathy," *Clinical Nephrology* 55(3):185-191, (2001).
Rinder, C.S., et al., "Selective Blockade of Membrane Attack Complex Formation During Simulated Extracorporeal Circulation Inhibits Platelet But Not Leukocyte Activation," *Journal of Thoracic Cardiovascular Surgery* 118(3):460-466, (1999).

(56) References Cited

OTHER PUBLICATIONS

Craddock, P.R., et al., "Complement and Leukocyte-Mediated Pulmonary Dysfunction in Hemodialysis," *New England Journal of Medicine* 296(14):769-774, (1977).
Johnson, R.J., "Complement Activation During Extracorporeal Therapy: Biochemistry, Cell Biology and Clinical Relevance," *Nephrology Dialysis Transplantation* 9(Suppl 2):36-45, (1994).
Verrier, E.D., et al., "Terminal Complement Blockade With Pexelizumab During Coronary Artery Bypass Graft Surgery Requiring Cardiopulmonary Bypass: A Randomized Trial," *Journal of the American Medical Association* 291(19):2319-2327, (2004).
Woodruff, T.M., et al., "A Potent Human C5a Receptor Antagonist Protects Against Disease Pathology in a Rat Model of Inflammatory Bowel Disease," *Journal of Immunology* 171(10):5514-5520, (2003).
Shen, Y., et al., "Yin and Yang: Complement Activation and Regulation in Alzheimer's Disease," *Progress in Neurobiology* 70(6):463-472, (2003).
Gasque, P., et al., "Complement Components of the Innate Immune System in Health and Disease in the CNS," *Immunopharmacology* 49(1-2):171-186, (2000).
Piddlesden, S.J., et al., "Soluble Complement Receptor 1 (sCR1) Protects Against Experimental Autoimmune Myasthenia Gravis," *Journal of Neuroimmunology* 71(1-2):173-177, (1996).
Barnum, S.R., "Complement in Central Nervous System Inflammation," *Immunologic Research* 26(1-3):7-13, (2002).
Vakeva, A.P., et al., "Myocardial Infarction and Apoptosis After Myocardial Ischemia and Reperfusion: Role of the Terminal Complement Components and Inhibition by Anti-C5 Therapy," *Circulation* 97(22):2259-2267, (1998).
Mulligan, M.S., et al., "Requirement and Role of C5a in Acute Lung Inflammatory Injury in Rats," *Journal of Clinical Investigation* 98(2):503-512, (1996).
Humbles, A.A., et al., "A Role for the C3a Anaphylatoxin Receptor in the Effector Phase of Asthma," *Nature* 406(6799):998-1001, (2000).
Riedemann, N.C., and P.A. Ward, "Complement in Ischemia Reperfusion Injury," *American Journal of Pathology* 162(2):363-367, (2003).
Geertinger, P., et al., "On the Reduced Atherogenic Effect of Cholesterol Feeding in Rabbits With Congenital Complement (C6) Deficiency," *Artery* 1:177-184, (1977).
Schmiedt, W., et al., "Complement C6 Deficiency Protects Against Diet-Induced Atherosclerosis in Rabbits," *Arteriosclerosis, Thrombosis, and Vascular Biology* 18(11):1790-1795, (1998).
Seifert, P.S., et al., "Isolation and Characterization of a Complement-Activating Lipid Extracted From Human Atherosclerotic Lesions," *Journal of Experimental Medicine* 172(2):547-557, (1990).
Seifert, P.S., and M.D. Kazatchkine, "Generation of Complement Anaphylatoxins and C5b-9 by Crystalline Cholesterol Oxidation Derivatives Depends on Hydroxyl Group Number and Position," *Molecular Immunology* 24(12):1303-1308, (1987).
Seifert, P.S., and M.D. Kazatchkine, "The Complement System in Atherosclerosis," *Atherosclerosis* 73(2-3):91-104, (1988).
Matsushita, M., et al., "Activation of the Lectin Complement Pathway by H-Ficolin (Hakata Antigen)," *Journal of Immunology* 168(7):3502-3506, (2002).
Fung, M., et al., "Inhibition of Complement, Neutrophil, and Platelet Activation by an Anti-Factor D Monoclonal Antibody in Simulated Cardiopulmonary Bypass Circuits," *Journal of Thoracic and Cardiovascular Surgery* 122(1):113-122, (2001).
Stengaard-Pedersen, K., et al., "Inherited Deficiency of Mannan-Binding Lectin-Associated Serine Protease 2," *New England Journal of Medicine* 349(6):554-560, (2003).
Takahashi, M., et al., "A Truncated Form of Mannose-Binding LectinAssociated Serine Protease (MASP)-2 Expressed by Alternative Polyadenylation Is a Component of the Lectin Complement Pathway," *International Immunology* 11(5):859-863, (1999).
Terui, T., "Inflammatory and Immune Reactions Associated With Stratum Corneum and Neutrophils in Sterile Pustular Dermatoses," *Tohoku Journal of Experimental Medicine* 190(4):239-248, (2000).

Ambrus, G., et al., "Natural Substrates and Inhibitors of Mannan-Binding LectinAssociated Serine Protease-I and -2: A Study on Recombinant Catalytic Fragments," *Journal of Immunology* 170:1374-1382, (2003).
Möller-Kristensen, M., et al., "Levels of Mannan-Binding Lectin-Associated Serine Protease-2 in Healthy Individuals," *Journal of Immunological Methods* 282(1-2):159-167, (2003).
Petersen, S.V., et al., "Control of the Classical and the MBL Pathway of Complement Activation," *Molecular Immunology* 37(14):803-811, (2000).
Dahl, M.R., et al., "MASP-3 and Its Association With Distinct Complexes of the Mannan-Binding Lectin Complement Activation Pathway," *Immunity* 15(1):127-135, (2001).
Petersen, S.V., et al., "An Assay for the Mannan-Binding Lectin Pathway of Complement Activation," *Journal of Immunological Methods* 257(1-2):107-116, (2001).
Endo, M., et al., "Complement Activation Through the Lectin Pathway in Patients With Henoch-Schonlein Purpura Nephritis," *American Journal of Kidney Diseases* 35(3):401-407, (2000).
Collard, C.D., et al., "Complement Activation After Oxidative Stress: Role of the Lectin Complement Pathway," *American Journal of Pathology* 156(5): 1549-1556, (2000).
Lu, J., et al., "Collectins and Ficolins: Sugar Pattern Recognition Molecules of the Mammalian Innate Immune System," *Biochimica et Biophysica Acta* 1572(2-3):387-400, (2002).
Schweinle, J.E., et al., "Human Mannose-Binding Protein Activates the Alternative Complement Pathway and Enhances Serum Bactericidal Activity on a Mannose-Rich Isolate of *Salmonella,*" *Journal of Clinical Investigation* 84(6):1821-1829, (1989).
Jordan, J.E., et al., "Inhibition of Mannose-Binding Lectin Reduces Postischemic Myocardial Reperfusion Injury," *Circulation* 104(12):1413-1418, (2001).
Stahl, G.L., et al., "Role for the Alternative Complement Pathway in Ischemia/Reperfusion Injury," *American Journal of Pathology* 162(2):449-455, (2003).
Collard, C.D., et al., "Endothelial Oxidative Stress Activates the Lectin Complement Pathway: Role of Cytokeratin 1," *American Journal of Pathology* 159(3):1045-1054, (2001).
Ji, Y.-H., et al., "Activation of the C4 and C2 Components of Complement by a Proteinase in Serum Bactericidal Factor, Ra Reactive Factor," *Journal of Immunology* 150(2):571-578, (1993).
Kilpatrick, D.C., "Mannan-Binding Lectin: Clinical Significance and Applications," *Biochimica et Biophysica Acta* 1572(2-3):401-413, (2002).
Mulligan, M.S., et al., "Protective Effects of Soluble CR1 in Complement- and Neutrophil-Mediated Tissue Injury," *Journal of Immunology* 148(5):1479-1485, (1992).
Chai, P.J., et al., "Soluble Complement Receptor-I Protects Heart, Lung, and Cardiac Myofilament Function From Cardiopulmonary Bypass Damage," *Circulation* 101(5):541-546, (2000).
Czermak, B.J., et al., "Protective Effects of C5a Blockade in Sepsis," *Nature Medicine* 5(7):788-792, (1999).
Goodfellow, R.M., et al., "Soluble Complement Receptor One (sCR1) Inhibits the Development and Progression of Rat Collagen-Induced Arthritis," *Clinical Experimental Immunology* 119(1):210-216, (2000).
Goodfellow, R.M., et al., "Local Therapy With Soluble Complement Receptor 1 (sCR1) Suppresses Inflammation in Rat Mono-Articular Arthritis," *Clinical Experimental Immunology* 110(1):45-52, (1997).
Morgan, K., et al., "Native Type II Collagen-Induced Arthritis in the Rat: The Effect of Complement Depletion by Cobra Venom Factor," *Arthritis and Rheumatism* 24(11):1356-1362, (1981).
Van Lent, P.L.E.M., et al., "Cationic Immune Complex Arthritis in Mice—A New Model: Synergistic Effect of Complement and Interleukin-I," *American Journal of Pathology* 140(6):1451-1461, (1992).
Kemp, P.A., et al., "Immunohistochemical Determination of Complement Activation in Joint Tissues of Patients With Rheumatoid Arthritis and Osteoarthritis Using Neoantigen-Specific Monoclonal Antibodies," *Journal of Clinical and Laboratory Immunology* 37(4):147-162, (1992).

(56) References Cited

OTHER PUBLICATIONS

Kaczorowski, S.L., et al., "Effect of Soluble Complement Receptor-I on Neutrophil Accumulation After Traumatic Brain Injury in Rats," *Journal of Cerebral Blood Flow and Metabolism* 15(5):860-864, (1995).
Sanders, M.E., et al., "Detection of Activated Terminal Complement (C5b-9) in Cerebrospinal Fluid From Patients With Central Nervous System Involvement of Primary Sjogren's Syndrome or Systemic Lupus Erythematosus," *Journal of Immunology* 138(7):2095-2099, (1987).
Wallis, R., et al., "Localization of the Serine Protease-Binding Sites in the Collagen-Like Domain of Mannose-Binding Protein," *Journal of Biological Chemistry* 279(14):14065-14073, (2004).
Jensenius, J.C., et al., "Recombinant Mannan-Binding Lectin (MBL) for Therapy," *Biochemical Society Transactions* 31(Pt 4):763-767, (2003).
Wallis, R., et al., "Interaction of Mannose-Binding Protein With Associated Serine Proteases: Effects of Naturally Occurring Mutations," *Journal of Biological Chemistry* 275(40):30962-30969, (2000).
Petersen, S.V., et al., "Generation of Antibodies Towards MASP-1 and MASP-2 Using Bacterial Expression Systems," *Molecular Immunology* 35(6-7):409, (1998) [abstract].
Chenoweth, D.E., "Complement Activation in Extracorporeal Circuits," *Annals of the New York Academy of Sciences* 516:306-313, (1987).
Bone, R.C., et al., "Definitions for Sepsis and Organ Failure," *Critical Care Medicine* 20(6):724-726, (1992).
Campbell, L.A., et al., "Detection of *Chlamydia pneumoniae* TWAR in Human Coronary Atherectomy Tissues," *Journal of Infectious Diseases* 172(2):585-588, (1995).
Cheung, A.K., "Biocompatibility of Hemodialysis Membranes," *Journal of the American Society of Nephrology.* 1(2):150-161, (1990).
Couser, W.G., et al., "The Effects of Soluble Recombinant Complement Receptor 1 on Complement-Mediated Experimental Glomerulonephritis," *Journal of the American Society of Nephrology* 5(11):1888-1894, (1995).
Bartlow, B.G., et al., "Nonimmunoglobulin C3 Activating Factor in Membranoproliferative Glomerulonephritis," *Kidney International* 15I(3):294-302, (1979).
Johnson, L.V., et al., "Complement Activation and Inflammatory Processes in Drusen Formation and Age Related Macular Degeneration," *Experimental Eye Research* 73(6):887-896, (2001).
Hugli, T.E., "Biochemistry and Biology of Anaphylatoxins," *Complement* 3(3):111-127, (1986).
Hageman, G.S., et al., "An Integrated Hypothesis That Considers Drusen as Biomarkers of Immune-Mediated Processes at the RPE-Bruch's Membrane Interface in Aging and Age-Related Macular Degeneration," *Progress in Retinal and Eye Research* 20(6):705-732, (2001).
Gerl, V.B., et al., "Extensive Deposits of Complement C3d and C5b-9 in the Choriocapillaris of Eyes of Patients With Diabetic Retinopathy," *Investigative Ophthalmology & Visual Science* 43(4):1104-1108, (2002).
Geertinger, P., et al., "Complement as a Factor in Arteriosclerosis," *Acta Pathologica et Microbiologica Scandinavica: Section A Pathology* 78A(3):284-288, (1970).
Francis, K., et al., "Complement C3a Receptors in the Pituitary Gland: A Novel Pathway by Which an Innate Immune Molecule Releases Hormones Involved in the Control of Inflammation," *FASEB Journal* 17(15):2266-2268, (2003).
Czlonkowska, A., et al., "Immune Processes in the Pathogenesis of Parkinson's Disease—A Potential Role for Microglia and Nitric Oxide," *Medical Science Monitor* 8(8):RA165-RA177, (2002).
Brenchley, P.E., et al., "Urinary C3dg and C5b-9 Indicate Active Immune Disease in Human Membranous Nephropathy," *Kidney International* 41(4):933-937, (1992).
Salant, D.J., et al., "Heymann Nephritis: Mechanisms of Renal Injury," *Kidney International* 35(4):976-984, (1989).

Seelen, M.A., et al., "Autoantibodies Against Mannose-Binding Lectin in Systemic Lupus Erythematosus," *Clinical Experimental Immunology* 134(2):335-343, (2003).
Schwaeble, W., et al., "The Mannan-Binding Lectin-Associated Serine Proteases (MASPs) and MAp 19: Four Components of the Lectin Pathway Activation Complex Encoded by Two Genes," *Immunobiology* 205(4-5):455-466, (2002).
Tada, T., et al., "Membrane Attack Complex of Complement and 20 kDa Homologous Restriction Factor (CD59) in Myocardial Infarction," *Virchows Archiv* 430(4):327-332, (1997).
Ohkohchi, K., et al., "Plasma Concentrations of Complement-Modulating Proteins (C1 Inhibitor, C4 Binding Protein, Factor Hand Factor I) in Inflammatory Dermatoses With Special Reference to Psoriasis," *Dermatologica* 179(Suppl 1):30-34, (1989).
Kerjaschki, D., "The Pathogenesis of Membranous Glomerulonephritis: From Morphology to Molecules," *Virchows Archiv B: Cell Pathology* 58(4):253-271, (1990).
Solomkin, J.S., et al., "Complement Activation and Clearance in Acute Illness and Injury: Evidence for C5a as a Cell-Directed Mediator of the Adult Respiratory Distress Syndrome in Man," *Surgery* 97(6):668-678, (1985).
Gatenby, P.A., "The Role of Complement in the Aetiopathogenesis of Systemic Lupus Erythematosus," *Autoimmunity* 11(1):61-66, (1991).
Weisman, H.F., et al., "Soluble Human Complement Receptor Type 1: In Vivo Inhibitor of Complement Suppressing Post-Ischemic Myocardial Inflammation and Necrosis," *Science* 249(4965):146-151, (1990).
Terui, T., et al., "Role of Neutrophils in Induction of Acute Inflammation in T-Cell-Mediated Immune Dermatosis, Psoriasis: A Neutrophil-Associated Inflammation-Boosting Loop," *Experimental Dermatology* 9(1):1-10, (2000).
Van Der Kolk, L.E., et al., "Complement Activation Plays a Key Role in the Side-Effects of Rituximab Treatment," *British Journal of Haematology* 115(4):807-811, (2001).
Trouw, L.A., et al., "Autoantibodies to Complement Components," *Molecular Immunology* 38(2-3):199-206, (2001).
Zhou, W., et al., "Predominant Role for C5b-9 in Renal Ischemia/Reperfusion Injury," *Journal of Clinical Investigation* 105(10):1363-1371, (2000).
Zhang, J., et al., "Early Complement Activation and Decreased Levels of Glycosylphosphatidylinositol-Anchored Complement Inhibitors in Human and Experimental Diabetic Retinopathy," *Diabetes* 51(12):3499-3504, (2002).
Takematsu, H., et al., "Activation of the Alternative Pathway of Complement in Psoriatic Lesional Skin," *Dermatologica* 181(4):289-292, (1990).
Scandrett, A.L., et al., "Acute Inflammation Is the Harbinger of Glomerulosclerosis in Anti-Glomerular Basement Membrane Nephritis," *American Journal of Physiology* 268(2 Pt 2):F258-F265, (1995).
Rumfeld, W.R., et al., "The Ninth Complement Component in Rheumatoid Arthritis, Behçet's Disease and Other Rheumatic Diseases," *British Journal of Rheumatology* 25(3):266-270, (1986).
Van De Graaf, E.A., et al., "ELISA of Complement C3a in Bronchoalveolar Lavage Fluid," *Journal of Immunological Methods* 147(2):241-250, (1992).
Ravirajan, C.T., et al., "Effect of Neutralizing Antibodies to IL-10 and C5 on the Renal Damage Caused by a Pathogenic Human Anti-dsDNA Antibody," *Rheumatology* 43(4):442-447, (2004).
Hammerschmidt, D.E., et al., "Association of Complement Activation and Elevated Plasma-C5a With Adult Respiratory Distress Syndrome: Pathophysiological Relevance and Possible Prognostic Value," *Lancet* 1(8175):947-949, (1980).
Glover, G.I., et al., "Synthetic Peptide Inhibitors of Complement Serine Proteases-I. Identification of Functionally Equivalent Protease Inhibitor Sequences in Serpins and Inhibition of Cls and D," *Molecular Immunology* 25(12):1261-1267, (1988).
Hogaboam, C.M., et al., "Mannose-Binding Lectin Deficiency Alters the CO0332 Development of Fungal Asthma: Effects on Airway Response, Inflammation, and Cytokine Profile," *Journal of Leukocyte Biology* 75(5):805-814, (2004).

(56) References Cited

OTHER PUBLICATIONS

Holm-Bentzen, M., et al., "A Prospective Double-Blind Clinically Controlled Multicenter Trial of Sodium Pentosanpolysulfate in the Treatment of Interstitial Cystitis and Related Painful Bladder Disease," *Journal of Urology* 138(3):503-507, (1987).
Kitano, A., et al., "Multifunctional Effects of Anticomplementary Agent K-76 on Carrageenan-Induced Colitis in the Rabbit," *Clinical Experimental Immunology* 94(2):348-353, (1993).
Matsushita, M., et al., "Activation of the Classical Complement Pathway by Mannose-Binding Protein in Association With a Novel Cls-Like Serine Protease," *Journal of Experimental Medicine* 176(6):1497-1502, (1992).
Morgan, B.P., "Clinical Complementology: Recent Progress and Future Trends," *European Journal of Clinical Investigation* 24(4):219-228, (1994).
Ikeda, K., et al., "Serum Lectin With Known Structure Activates Complement Through the Classical Pathway," *Journal of Biological Chemistry* 262(16):7451-7454, (1987).
Linton, S.M., et al., "Complement Activation and Inhibition in Experimental Models of Arthritis," *Molecular Immunology* 36(13-14):905-914, (1999).
Baldwin, W.M., et al., "Complement in Transplant Rejection: Diagnostic and Mechanistic Considerations," *Springer Seminars in Immunopathology* 25(2):181-197, (2003).
Neth, O., et al., "Mannose-Binding Lectin Binds to a Range of Clinically Relevant Microorganisms and Promotes Complement Deposition," *Infection and Immunity* 68(2):688-693, (2000).
Kitano, A., et al., "New Treatment of Ulcerative Colitis With K-76," *Diseases of the Colon & Rectum* 35(6):560-567, (1992).
Kuhlman, M., et al., "The Human Mannose-Binding Protein Functions as an Opsonin," *Journal of Experimental Medicine* 169(5):1733-1745, (1989).
Meri, S., et al., "Activation of the Alternative Pathway of Complement by Monoclonal λ Light Chains in Membranoproliferative Glomerulonephritis," *Journal of Experimental Medicine* 175(4):939-950, (1992).
Mollnes, T.E., and A. Paus, "Complement Activation in Synovial Fluid and Tissue From Patients With Juvenile Rheumatoid Arthritis," *Arthritis and Rheumatism* 29(11):1359-1364, (1986).
Niculescu, F., et al., "Persistent Complement Activation on Tumor Cells in Breast Cancer," *American Journal of Pathology* 140(5):1039-1043, (1992).
Nilsson, B., et al., "Compstatin Inhibits Complement and Cellular Activation in Whole Blood in Two Models of Extracorporeal Circulation," *Blood* 92(5):1661-1667, (1998).
Riedemann, N.C., et al., "Increased C5a Receptor Expression in Sepsis," *Journal of Clinical Investigation* 110(1):101-108, (2002).
Polotsky, V.Y., et al., "Interactions of Human Mannose-Binding Protein With Lipoteichoic Acids," *Infection and Immunity* 64(1):380-383, (1996).
Brandt, J., et al., "Role of the Complement Membrane Attack Complex (C5b-9) in Mediating Experimental Mesangioproliferative Glomerulonephritis," *Kidney International* 49(2):335-343, (1996).
Klein, R.J., et al., "Complement Factor H Polymorphism in Age-Related Macular Degeneration," *Science* 308(5720):385-389, (2005).
Haines, J.L., et al., "Complement Factor H Variant Increases the Risk of Age Related Macular Degeneration," *Science* 308(5720):419-421, (2005).
Edwards, A.O., et al., "Complement Factor H Polymorphism and Age-Related Macular Degeneration," *Science* 308(5720):421-424, (2005).
Iwaki, D., et al., "Production and Purification of Recombinants of Mouse MASP-2 and sMAP," *Journal of Endotoxin Research* 11(1):47-50, (2005).
Hart, M.L., et al., "Gastrointestinal Ischemia-Reperfusion Injury Is Lectin Complement Pathway Dependent Without Involving C1q," *Journal of Immunology* 174(10):6373-6380, (2005).
Walsh, M.C., et al., "Mannose-Binding Lectin Is a Regulator of Inflammation That Accompanies Myocardial Ischemia and Reperfusion Injury," *Journal of Immunology* 175(1):541-546, (2005).

Roos, A., et al., "Human IgA Activates the Complement System Via the Mannan Binding Lectin Pathway," *Journal of Immunology* 167(5):2861-2868, (2001).
Banda, N.K., et al., "Prevention of Collagen-Induced Arthritis in Mice Transgenic for the Complement Inhibitor Complement Receptor I—Related Gene/Protein y," *Journal of Immunology* 171(4):2109-2115, (2003).
Celik, I., et al., "Role of the Classical Pathway of Complement Activation in Experimentally Induced Polymicrobial Peritonitis," *Infection and Immunity* 69(12):7304-7309, (2001).
Pratt, J.R., et al., "Nontransgenic Hyperexpression of a Complement Regulator in Donor Kidney Modulates Transplant Ischemia/Reperfusion Damage, Acute Rejection, and Chronic Nephropathy," *American Journal of Pathology* 163(4):1457-1465, (2003).
Turnberg, D., et al., "CD59a Deficiency Exacerbates Ischemia-Reperfusion Injury in Mice," *American Journal of Pathology* 165(3):825-832, (2004).
Takahashi, M., et al., "Role of MASP-1 and/or MASP-3 in Activation of the Lectin Pathway," in "Oral Session 1: Mechanisms of Activation," *International Immunopharmacology* 2(9):1220, (2002).
Casanova, J.-L., et al., "Human Mannose-Binding Lectin in Immunity: Friend, Foe, or Both?" *Journal of Experimental Medicine* 199(10):1295-1299, (2004).
Malhotra, R., et al., "Glycosylation Changes of IgG Associated With Rheumatoid Arthritis Can Activate Complement Via the Mannose-Binding Protein," *Nature Medicine* 1(3):237-243, (1995).
Hansen, T.K., et al., "Elevated Levels of Mannan-Binding Lectin in Patients With Type 1 Diabetes," *Journal of Clinical Endocrinology & Metabolism* 88(10):4857-4861, (2003).
Hovind, P., et al., "Mannose-Binding Lectin as a Predictor of Microalbuminuria in Type 1 Diabetes: An Inception Cohort Study," *Diabetes* 54(5):1523-1527, (2005).
Hansen, T.K., et al., "Mannose-Binding Lectin and Mortality in Type 2 Diabetes," *Archives of Internal Medicine* 166(18):2007-2013, (2006).
Hansen, T.K., et al., "Association Between Mannose-Binding Lectin and Vascular Complications in Type 1 Diabetes," *Diabetes* 53(6):1570-1576, (2004).
De Vries, B., et al., "The Mannose-Binding Lectin-Pathway Is Involved in Complement Activation in the Course of Renal Ischemia-Reperfusion Injury," *American Journal of Pathology* 165(5):1677-1688, (2004).
Nozaki, M., et al., "Drusen Complement Components C3a and C5a Promote Choroidal Neovascularization," *Proceedings of the National Academy of Sciences of the United States of America* 103(7):2328-2333, (2006).
Bora, P.S., et al., "Role of Complement and Complement Membrane Attack Complex in Laser-Induced Choroidal Neovascularization," *Journal of Immunology* 174(1):491-497, (2005).
Connolly, A.M., et al., "Complement 3 Deficiency and Oral Prednisolone Improve Strength and Prolong Survival of Laminin al-Deficient Mice," *Journal of Neuroimmunology* 127(1):80-87, (2002).
Spuler, S., et al., "Unexpected Sarcolemmal Complement Membrane Attack Complex Deposits on Nonnecrotic Muscle Fibers in Muscular Dystrophies," *Neurology* 50(1):41-46, (1998).
Liu, J., et al., "Dysferlin, a Novel Skeletal Muscle Gene, Is Mutated in Miyoshi Myopathy and Limb Girdle Muscular Dystrophy," *Nature Genetics* 20(1):31-36, (1998).
Porter, J.D., et al., "A Chronic Inflammatory Response Dominates the Skeletal Muscle Molecular Signature in Dystrophin-Deficient mdx Mice," *Human Molecular Genetics* 11(3):263-272, (2002).
Cuchacovich, M., et al., "Potential Pathogenicity of Deglycosylated IgG Cross Reactive With Streptokinase and Fibronectin in the Serum of Patients With Rheumatoid Arthritis," *Journal of Rheumatology* 23(1):44-51, (1996).
Baelder, R., et al., "Pharmacological Targeting of Anaphylatoxin Receptors During the Effector Phase of Allergic Asthma Suppresses Airway Hyperresponsiveness and Airway Inflammation," *Journal of Immunology* 174(2):783-789, (2005).
Taube, C., et al., "Inhibition of Complement Activation Decreases Airway Inflammation and Hyperresponsiveness," *American Journal of Respiratory and Critical Care Medicine* 168(11):1333-1341, (2003).

(56) References Cited

OTHER PUBLICATIONS

Drouin, S.M., et al., "Cutting Edge: The Absence of C3 Demonstrates a Role for Complement in Th2 Effector Functions in a Murine Model of Pulmonary Allergy," *Journal of Immunology* 167(8):4141-4145, (2001).

Peng, T., et al., "Role of C5 in the Development of Airway Inflammation, Airway Hyperresponsiveness, and Ongoing Airway Response," *Journal of Clinical Investigation* 115(6):1590-1600, (2005).

Huang, Z., "Structural Chemistry and Therapeutic Intervention of Protein-Protein Interactions in Immune Response, Human Immunodeficiency Virus Entry, and Apoptosis," *Pharmacology & Therapeutics* 86(3):201-215, (2000).

Khan, A.U., et al., "Ribozymes: A Modern Tool in Medicine," *Journal of Biomedical Science* 10(5):457-467, (2003).

Shoji, Y., et al., "Current Status of Delivery Systems to Improve Target Efficacy of Oligonucleotides," *Current Pharmaceutical Design* 10(7):785-796, (2004).

Takahashi, M., et al., "Essential Role of Mannose-Binding Lectin Associated Serine Protease-I in Activation of the Complement Factor D, " *Journal of Experimental Medicine* 207(1):29-37, (2010).

Rieben, R., et al., "Immunoglobulin M-Enriched Human Intravenous Immunoglobulin Prevents Complement Activation In Vitro and In Vivo in a Rat Model of Acute Inflammation," *Blood* 93(3):942-951, (1999).

Simon, H.U., et al., "IVIG—Mechanisms of Action," *Allergy* 58(7):543-552, (2003).

Harlow, E., et al., "Using Antibodies: A Laboratory Manual," Cold Spring Harbor Press, Cold Spring Harbor, N.Y., 1999, pp. 44, 45, and 52.

Tan, S., et al., "Improvements on the Purification of Mannan-Binding Lectin and Demonstration of Its Ca2+-Independent Association With a C 1 s-Like Serine Protease," *Biochemical Journal* 319(Pt 2):329-332, (1996).

MacKinnon, C.M., et al., "Molecular Cloning of cDNA for Human Complement Component Cls: The Complete Amino Acid Sequence," *European Journal of Biochemistry* 169(3):547-553, (1987).

Journet, A., and M. Tosi, "Cloning and Sequencing of Full-Length cDNA Encoding the Precursor of Human Complement Component Clr," *Biochemical Journal* 240(3):783-787, (1986).

Endo, Y., et al., "Exon Structure of the Gene Encoding the Human Mannose Binding Protein-Associated Serine Protease Light Chain: Comparison With Complement Clr and Cls Genes," *International Immunology* 8(9):1355-1358, (1996).

Baatrup, G., et al., "Demonstration in Human Plasma of a Lectin Activity Analogous to That of Bovine Conglutinin," *Scandinavian Journal of Immunology* 26(4):355-361, (1987).

Jack, D.L., and M.W. Turner, "Anti-Microbial Activities of Mannose-Binding Lectin," *Biochemical Society Transactions* 31(Pt 4):753-757, (2003).

Bally, I., et al., "Residue GLN340, at the Interface Between the CCP1 and CCP2 Modules of Cls, Is a Key Element of C4 Recognition," *International Immunopharmacology* 2(9):1228, (2002) [abstract].

Barton, G.J., "Protein Multiple Sequence Alignment and Flexible Pattern Matching," *Methods in Enzymology* 183:403-428, (1990).

Davies, E.J., et al., "Mannose-Binding Protein Gene Polymorphism in Systemic Lupus Erythematosus," *Arthritis & Rheumatism* 38(1): 110-114, (1995).

Deng, Y.-J., et al., "Molecular Determinants of Polyreactive Antibody Binding: HCDR3 and Cyclic Peptides," *Clinical & Experimental Immunology* 119(1):69-76, (2000).

Garred, P., et al., "Increased Frequency of Homozygosity of Abnormal Mannan-Binding-Protein Alleles in Patients With Suspected Immunodeficiency," *Lancet* 346(8980):941-943, (1995).

Garred, P., et al., "Susceptibility to HIV Infection and Progression of AIDS in Relation to Variant Alleles of Mannose-Binding Lectin," *Lancet* 349(9047):236-240, (1997).

Garred, P., et al., "Diallelic Polymorphism May Explain Variations of the Blood Concentration of Mannan-Binding Protein in Eskimos, But Not in Black Africans," *European Journal of Immunogenetics* 19(6):403-412, (1992).

Jensenius, J.C., "Mannan-Binding Lectin (MBL): From Investigations on Fish and Chickens to Substitution Therapy in an Infant With Severe Infections," in M.W. Steward (ed.), *Immunology: Joint Congress of BSI and NVVI Abstracts* 86(Suppl 1):100, (1995).

Jensenius, J.C., et al., "Eggs: Conveniently Packaged Antibodies. Methods for Purification of Yolk IgG," *Journal of Immunological Methods* 46(1):63-68, (1981).

Kawasaki, T., et al., "Isolation and Characterization of a Mannan-Binding Protein From Rabbit Liver," *Biochemical and Biophysical Research Communications* 81(3):1018-1024, (1978).

Kawasaki, N., et al., "A Serum Lectin (Mannan-Binding Protein) Has Complement-Dependent Bactericidal Activity," *Journal of Biochemistry* 106(3):483-489, (1989).

Kilpatrick, D.C., "Mannan Binding Protein in Sera Positive for Rheumatoid Factor," *British Journal of Rheumatology* 36(2):207-209, (1997).

Klein, J., et al., "B-Cell Receptors, Immunoglobulins and FC Receptors," "Immunology," 2d ed., *Blackwell Science*, Oxford, United Kingdom, Chapter 8, pp. 229-240 (1997).

Law, S.K.A., et al., "Complement," 2d ed., IRL Press, Oxford, United Kingdom, 1995, 27 pages.

Leytus, S.P. et al., "Nucleotide Sequence of the cDNA Coding for Human Complement Clr," *Biochemistry* 25(17):4855-4863, (1986).

Lipscombe, R.J., et al., "High Frequencies in African and Non-African Populations of Independent Mutations in the Mannose-Binding Protein Gene," *Human Molecular Genetics* 1(9):709-715, (1992).

Madsen, H.O., et al, "A New Frequent Allele Is the Missing Link in the Structural Polymorphism of the Human Mannan-Binding Protein," *Immunogenetics* 40(1):37-44, (1994).

Matsushita, M., et al., "Cleavage of the Third Component of Complement (C3) by Mannose-Binding Protein-Associated Serine Protease (MASP) With Subsequent Complement Activation," *Immunobiology* 194(4-5):443-448, (1995).

Nielsen, S.L., et al., "The Level of the Serum Opsonin, Mannan-Binding Protein in HIV-1 Antibody-Positive Patients," *Clinical and Experimental Immunology* 100(2):219-222, (1995).

Rossi, V., et al., "Baculovirus-Mediated Expression of Truncated Modular Fragments From the Catalytic Region of Human Complement Serine Protease Cls," *Journal of Biological Chemistry* 273(2):1232-1239, (1998).

Rossi, V., et al., "Cls/MASP-2 Chimeras: Tools to Determine the Relative Contributions of the CCP Modules and 7 Serine Protease Domain of MASP-2 to Its Higher C4 Cleaving Activity," *International Immunopharmacology* 2(9):1253, (2002) [abstract].

Rossi, V., et al., "Substrate Specificities of Recombinant Mannan-Binding Lectin-Associated Serine Proteases-1 and -2," *Journal of Biological Chemistry* 276(44):40880-40887, (2001).

Sato, T., et al., "Molecular Characterization of a Novel Serine Protease Involved in Activation of the Complement System by Mannose-Binding Protein," *International Immunology* 6(4):665-669, (1994).

Sumiy A. M., et al., "Molecular Basis of Opsonic Defect in Immunodeficient Children," *Lancet* 337(8757):1569-1570, (1991).

Summerfield, J.A., et al., "Mannose-Binding Protein Gene Mutations Associated With Unusual and Severe Infections in Adults," *Lancet* 345(8954):886-889, (1995).

Super, M., et al., "Association of Low Levels of Mannan-Binding Protein With a Common Defect of Opsonisation," *Lancet* 11(8674):1236-1239, (1989).

Takada, F., et al., "A New Member of the Cls Family of Complement Proteins Found in a Bactericidal Factor, Ra-Reactive Factor, in Human Serum," *Biochemical and Biophysical Research Communications* 196(2):1003-1009, (1993).

Thiel, S., et al., "Identification of a New Mannan-Binding Protein Associated Serine Protease (MASP-2)," *Immunology* 86(Suppl. 1):101, 1995 [abstract].

(56) References Cited

OTHER PUBLICATIONS

Tosi, M., et al., "Complete cDNA Sequence of Human Complement Cls and Close Physical Linkage of the Homologous Genes Cls and Clr," *Biochemistry* 26(26):8516-8524, (1987).
Turner, MW., "Mannose-Binding Lectin (MBL) in Health and Disease," *Immunobiology* 199(2):327-339, (1998).
Turner, M.W., "Mannose-Binding Lectin: The Pluripotent Molecule of the Innate Immune System," *Immunology Today*17(11):532-540, (1996).
Van De Geijn, F.E., et al., "Mannose-Binding Lectin Polymorphisms Are Not Associated With Rheumatoid Arthritis—Confirmation in Two Large Cohorts," *Rheumatology* 47(8):1168-1171, (2008).
Abaza et al., "Effects of amino acid substitutions outside an antigenic site on protein binding to monoclonal antibodies of predetermined specificity obtained by peptide immunization: demonstration with region 94-100 (antigenic site 3) of myoglobin," *Journal of Protein Chemistry* 11(5):433-444, (1992).
Colman et al., "Effects of amino acid sequence changes on antibody-antigen interactions," *Research in Immunology* 145(1):33-36, (1994).
Harlow et al., *Antibodies, Cold Spring Harbor Labrotaries*, 567-569, (1988).
Lederman et al., "A single amino acid substitution in a common African allele of the CD4 molecule ablates binding of the monoclonal antibody, OKT4," *Molecular Immunology* 28(11):1171-1181, (1991).
Ziccardi, R.J., "Nature of the Interaction between the C1q and $C1r_2s_2$ Subunits of the First Component of Human Complement," *Molecular Immunology* 22(4): 489-494 (1985).
Kilpatrick, D.C., et al., "Association between mannan binding protein deficiency and recurrent miscarriage," *Human Reproduction* 10(9): 2501-2505 (1995).
Vorup-Jensen, T., et al., "Cloning of cDNA Encoding a Human MASP-like Protein (MASP-2)" *Mol. Immunol*. 33(Suppl. 1): 81 (1996). (Meeting abstract).
Rasmussen, H.H., et al., "Towards a Comprehesive Database of Proteins from the Urine of Patients with Bladder Cancer," *Journal of Urology* 155:2113-2119 (1996).
Thiel, S., et al., "Identification of a New Mannan-Binding Lectin Associated Serine Protease (MAP-2)," *Mol Immunol* 33(Suppl. 1):91 (1996). (Abstract).
Thiel et al., "Assays for the functional activity of the mannan-binding lectin pathway of complement activation," *Immunobiol*. 205(4-5) 446-454, (2002).
Chen, M., et al., "ANCA-associated vasculitides—advances in pathogenesis and treatment," *Nat. Rev. Rheumatol*. 6:653-664 (2010).
International Search Report dated Aug. 25, 2004, issued in corresponding PCT/DK2004/000338, filed May 12, 2004, 4 pages.
Harlow, E., "Antibody Responses," In: *Antibodies, A Laboratory Manual*, Cold Spring Harbor Laboratory, Chapter 4, p. 37-59, (1988).
Damschroder, M. M., et al., "Analysis of human and primate CD2 molecules by protein sequence and epitope mapping with anti-human CD2 antibodies," *Mol Immunol* 41(10):985-1000 (2004).
Sotgiu, S., et al., "Genes, environment, and susceptibility to multiple sclerosis," *Neurobiology of Disease* 17:131-143 (2004).
Wakai, K., et al., "Risk Factors for IgA Nephropathy: A Case-Control Study with Incident Cases in Japan," *Nephron* 90:16-23 (2002).
Carter, John Mark and Loomis-Price, Larry, "B Cell Epitope Mapping Using Synthetic Peptides" In: *Current Protocols in Immunology*, (2004) 9.4.1-9.4.23 (Supplement 60).

* cited by examiner

```
Structure       ----signal-----------)-----------------------[---H1--]--------
P18525          MDFGLSLIFLVLVKGVLCEVKLVESGGGLVQPGGSLKLSCAASGFTFSSYTMSWVRQTP
P18526          MDFGLRLIFLVLTLKGVKCEVQLVESGGGLVKPGGSLKLSCAASGFAFSSYDMSWVRQTP
P18529          MDFVLSLIFLALILKGVQCEVHLVESGGGLVKPGGSLKLSCVVSGFTPNKYAMSWVRQTP
P01764          MDFGLSWLFLVAILKGVQCEVQLLESGGGLVQPGGSLRLSCAASGFTFSSYAMSWVRQAP
P01783          ---RLNLVPLVLILKGVQCDVQLVESGGGLVQPGGSRKLSCAASGFTFSSFGMHWVRQAP
DNE16140-4con   MSFSNTLVFLLFLLKGILCEVQLVESGGGLVQPGRSLKLSCLVSGFTFSNFGMNWIRQAP
DNE16140-5con   MSFSNTLVFLLFLLKGILCEVQLVESGGGLVQPGRSLKLSCLVSGFTFSNFGMNWIRQAP
DNE16140-1con   MSFSNTLVFLLFLLKGILCEVQLVESGGGLVQPGRSLKLSCLVSGFTFSNFGMNWIRQAP
DNE16140-2con   MSFSNTLVFLLFLLKGILCEVQLVESGGGLVQPGRSLKLSCLVSGFTPSNFGMNWIRQAP
DNE16140-3con   MSFSNTLVFLLFLLKGILCEVQLVEPGGGLVQPGRSLKLSCLVSGFTFSNFGMNWIRQAP
DNE16140-8con   MSFSNTLVFLLFLLKGILCEVQLVESGGGLVQPGRSLKLSCLVSGFTFSNFGMNWIRQAP
P01868          ------------------------------------------------------------
P01869          ------------------------------------------------------------
P20759          ------------------------------------------------------------
P20760          ------------------------------------------------------------

Structure       --------[--H2---]------------------------------------[--
P18525          EKRLEWVAYISNGGGSTYYPDTVKGRFTISRDNAKNNLYLQMSSLKSEDTAMYYCAR---
P18526          EKRLEWVAYISSGSGSTYYPDTVKGRFTISRDNAKNTLYLQMSSLKSEDTAMYYCAR---
P18529          EKRLEWVATISGGGLYTYYPDSVKGRFTISRDNAQNTLYLQMSSLRSEDTAMYYCAR---
P01764          GKGLEWVSAISGSGGSTYYGDSVKGRFTISRDNSENTLYLQMNSLRAEDTAVYYCAK---
P01783          EKGLEWVAYISSGSGTLHYADTVEGRFTISRDNPENTLFLQMTSLRSEDTAMYYCARNGN
DNE16140-4con   GKGLEWVASISSGGTYIYHADTLKGRFTISRENAKNTLYLQMTSLRSEDTALYYCARGPY
DNE16140-5con   GKGLEWVASISSGGTYIYHADTLKGRFTISRENAKNTLYLQMTSLRSEDTALYYCARGPY
DNE16140-1con   GKGLEWVASISSGGTYIYHADTLKGRFTISRENAKNTLYLQMTSLRSEDTALYYCARGPY
DNE16140-2con   GKGLEWVASISSGGTYIYHADTLKGRFTISRENAKNTLYLQMTSLRSEDTALYYCARGPY
DNE16140-3con   GKGLEWVASISSGGTYIYHADTLKGRFTISRENAKNTLYLQMTSLRSEDTALYYCARGPY
DNE16140-8con   GKGLEWVASISSGGTYIYHADTLKGRFTISRENAKNTLYLQMTSLRSEDTALYYCARGPY
P01868          ------------------------------------------------------------
P01869          ------------------------------------------------------------
P20759          ------------------------------------------------------------
P20760          ------------------------------------------------------------

Structure       -H3--------)-----------[--------------CH1------------------
P18525          ------------------------------------------------------------
P18526          ------------------------------------------------------------
P18529          ------------------------------------------------------------
P01764          ------------------------------------------------------------
P01783          ---YPYYAMDYWGQGTSVTVSS---------------------------------------
DNE16140-4con   HSRYIPYLMDAWGQGASVTVSSAETTAPSVYPLAPGTALKSNSMVTLGCLVKGYFPEPVT
DNE16140-5con   HSRYIPYLMDAWGQGASVTVSSAETTAPSVYPLAPGTALKSNSMVTLGCLVKGYFPEPVT
DNE16140-1con   HSRYIPYLMDAWGQGASVTVSSAETTAPSVYPLAPGTALKSNSMVTLGCLVKGYFPEPVT
DNE16140-2con   HSRYIPYLMDAWGQGASVTVSSAETTAPSVYPLAPGTALKSNSMVTLGCLVKGYFPEPVT
DNE16140-3con   HSRYIPYLMDAWGQGASVTVSSAETTAPSVYPLAPGTALKSNSMVTLGCLVKGYFPEPVT
DNE16140-8con   HSRYIPYLMDAWGQGASVTVSSAETTVPSVYPLAPGTALKSNSMVTLGCLVKGYFPEPVT
P01868          ----------------------AKTTPPSVYPLAPGSAAQTNSMVTLGCLVKGYFPEPVT
P01869          ----------------------AKTTPPSVYPLAPGSAAQTNSMVTLGCLVKGYFPEPVT
P20759          ----------------------AETTAPSVYPLAPGTALKSNSMVTLGCLVKGYFPEPVT
P20760          ----------------------AETTAPSVYPLAPGTALKSNSMVTLGCLVKGYFPEPVT P18525          ------------------------------------------------------------
P18526          ------------------------------------------------------------
P18529          ------------------------------------------------------------
P01764          ------------------------------------------------------------
P01783          ------------------------------------------------------------
DNE16140-4con   VTWNSGALSSGVHTFPAVLQSGLYTLTSSVTVPSSTWPSQTVTCNVAHPASSTKVDKKIV
DNE16140-5con   VTWNSGALSSGVHTFPAVLQSGLYTLTSSVTVPSSTWPSQTVTCNVAHPASSTKVDKKIV
DNE16140-1con   VTWNSGALSSGVHTFPAVLQSGLYTLTSSVTVPSSTWPSQTVTCNVAHPASSTKVDKKIV
DNE16140-2con   VTWNSGALSSGVHTFPAVLQSGLYTLTSSVTVPSSTWPSQTVTCNVAHPASSTKVDKKIV
DNE16140-3con   VTWNSGALSSGVHTFPAVLQSGLYTLTSSVTVPSSTWPSQTVTCNVAHPASSTKVDKKIV
DNE16140-8con   VTWNSGALSSGVHTFPAVLQSGLYTLTSSVTVPSSTWPSQTVTCNVAHPASSTKVDKKIV
P01868          VTWNSGSLSSGVHTFPAVLQSDLYTLSSSVTVPSSPRPSETVTCNVAHPASSTKVDKKIV
P01869          VTWNSGSLSSGVHTFPAVLQSDLYTLSSSVTVPSSPRPSETVTCNVAHPASSTKVDKKIV
P20759          VTWNSGALSSGVHTFPAVLQSGLYTLTSSVTVPSSTWPSQTVTCNVAHPASSTKVDKKIV
P20760          VTWNSGALSSGVHTFPAVLQSGLYTLTSSVTWNSQAVTCNVAHPASSTKVDKKIV
```

FIG. 11

```
Structure       ---Signal--------------------------------[---L1----]------
DWE16140-6con   MGVPTQLLGLLLLWITDAICDIQMTQSPGSLCASLGETVTIECRASDDIYSNLAWYQQKP
DWE16140-7con   MGVPTQLLGLLLLWITDAICDIQMTQSPGSLCASLGETVTIECRASDDIYSNLAWYQQKP
DWE16140-10con  MGVPTQLLGLLLLWITDAICDIQMTQSPGSLCASLGETVTIECRASDDIYSNLAWYQQKP
DWE16140-9      MGVPTQLLGLLLLWITDAICDIQMTQSPGSLCASLGETVTIECRASDDIYSNLAWYQQKP
P01594          ------------DIQMTQSPSSLSASVGDRVTITCQASQDISDYLNWYQQKP
P01595          ------------DIQMTQSPSPLSASVGDSVTITCQASQDIRNSLIWYQQKP
P01635          MSVLTQVLALLLLWLTGARCDIQMTQSPASLSASVGETVTITCRASGNIHNYLAWYQQKQ
P01636          ------------DIQMTQSPDYLSASVGETVTITCRASENIYSYLAWYQQKQ
P01637          MRTPAQFLGILLLWFPGIKCDIKMTQSPSSMYASLGERVTISCKASQDINSYLTWFQQKP
P01835          ------------------------------------------------------------
P01836          ------------------------------------------------------------
P01837          ------------------------------------------------------------

Structure       -------[--L2--]---------------------------[--L3---]---
DWE16140-6con   GNSPQLLIFDGNRLADGVPSRFSGSGSGTQYSLKMKSLQFEDVASYFCQQYNNYPLTFGS
DWE16140-7con   GNSPQLLIFDGNRLADGVPSRFSGSGSGTQYSLKMKSLQFEDVASYFCQQYNNYPLTFGS
DWE16140-10con  GNSPQLLIFDGNRLADGVPSRFSGSGSGTQYSLKMKSLQFEDVASYFCQQYNNYPLTFGS
DWE16140-9      GNSPQLLIFDGNRLADGVPSRFSGSGSGTQYSLKMKSLQFEDVASYFCQQYNNYPLTFGS
P01594          GKAPKLLIYDASNLESGVPSRFSGSGSGAHPTFTISSLQPEDIATYYCQQYDYLPWTFGQ
P01595          GKAPKFLIYDAENLEIGVPSRFEGSGSGTDFALSISSLQPEDFATYYCQQYINLPYTFGQ
P01635          GKSPQLLVYNAKTLADGVPSRFSGSGSGTQYSLKINSLQPEDFGSTYCQHFWSTP-----
P01636          GKSPQLLVYDAKTLVEGVPSRFSGSGSGTQFSLKINSLQPEDFGSYYCQHHYGIPFTFGS
P01637          GKSPKTLIYRANRLVDGVPSRFSGSGSGQDFSLTISSLEYEDMGIYYCLQYDEFPLTFGA
P01835          ------------------------------------------------------------
P01836          ------------------------------------------------------------
P01837          ------------------------------------------------------------

Structure       ------------[--------------------------CL----------------
DWE16140-6con   GTKLEIKRADAAPTVSIFPPSMEQLTSGGATVVCFVNNFYPRDISVKWKIDGSEQRDGVL
DWE16140-7con   GTKLEIKRADAAPTVSIFPPSMEQLTSGGATVVCFVNNFYPRDISVKWKIDGSEQRDGVL
DWE16140-10con  GTKLEIKRADAAPTVSIFPPSMEQLTSGGATVVCFVNNFYPRDISVKWKIDGSEQRDGVL
DWE16140-9      GTKLEIKRADAAPTVSIFPPSMEQLTSGGATVVCFVNNFYPRDISVKWKIDGSEQRDGVL
P01594          GTKVEIKR----------------------------------------------------
P01595          GTKLEIKR----------------------------------------------------
P01635          ------------------------------------------------------------
P01636          GTKLEIKR----------------------------------------------------
P01637          GTKLEIKR----------------------------------------------------
P01835          --------ADAAPTVSIFPPSTEQLATGGASVVCLMNNFYPRDISVKWKIDGTERRDGVL
P01836          --------ADAAPTVSIFPPSMEQLTSGGATVVCFVNNFYPRDISVKMKIDGSEQRDGVL
P01837          --------ADAAPTVSIFPPSSEQLTSGGASVVCFLNNFYPRDINVEWKIDGSERQNGVL Structure       ------------------------------------------------------------
DWE16140-6con   DSVTDQDSKDSTYSMSSTLSLTKVEYERHNLYTCEVVHKTSSSPVVKSFNRNEKGEFQHT
DWE16140-7con   DSVTDQDSKDGTYSMSSTLSLTKVEYERHNLYTCEVVHKTSSSPVVKSFNRNEKGEFQHT
DWE16140-10con  DSVTDQDSKDSTYSMSSTLSLTKVEYERHNLYTCEVVHKTSFS-----------------
DWE16140-9      DSVTDQDSKDSTYSMSSTLSLTKVEYERHNLYTCEVVHKTSSSPVVKSFNRNEKGEFQHT
P01594          ------------------------------------------------------------
P01595          ------------------------------------------------------------
P01635          ------------------------------------------------------------
P01636          ------------------------------------------------------------
P01637          ------------------------------------------------------------
P01835          DSVTDQDSKDSTYSMSSTLSLTKADYESHNLYTCEVVHKTSSSPVVKSFNRNEC------
P01836          DSVTDQDSKDSTYSMSSTLSLTKVEYERIENLYTCEVVHKTSSSPVVKSFNRNEC------
P01837          NSWTDQDSKDSTYSMSSTLTLTKDEYERHNSYTCEATHKTSTSPIVKSFNRNEC------
```

Sequence of the heavy chain (DWE16140-1,2,3,4, 5,8) and sequence of the light chain (DWE16140-6,7,10,9) of the antibody Nimoab101 aligned to the homologue sequences identified by Blast searches.

ANTIBODIES TO MASP-2

CROSS REFERENCE TO RELATED APPLICATIONS

The present application is a divisional of pending U.S. patent application Ser. No. 16/209,255, filed Dec. 4, 2018, which is a divisional of prior U.S. patent application Ser. No. 14/745,247, filed Jun. 19, 2015, now issued a U.S. Pat. No. 10,189,909, which is a divisional of prior U.S. patent application Ser. No. 10/556,509, filed Aug. 23, 2006, now issued as U.S. Pat. No. 9,096,676, priority from the filing date of which is hereby claimed under 35 U.S.C. § 120, which is a 371 National Phase Application of International PCT Application No. PCT/DK04/00338, filed May 12, 2004, now lapsed, which claims priority to Danish Patent Application No. PA 2003 00716, filed May 12, 2003, now lapsed.

STATEMENT REGARDING SEQUENCE LISTING

The sequence listing associated with this application is provided in text format in lieu of a paper copy and is hereby incorporated by reference into the specification. The name of the text file containing the sequence listing is MP_1_0117_US6_SequenceListingasFiled_20210218. K the text file is 86 KB, was created on Feb. 18, 2021; and is being submitted via EFS-Web with the filing of the specification.

FIELD OF INVENTION

The present invention relates to antibodies to MASP-2 and functional equivalents thereof. In particular, the invention relates to MASP-2 antibodies capable of inhibiting the function of MASP-2. Furthermore, the invention relates to methods of producing said antibodies, methods of inhibiting MASP-2 activity as well as to pharmaceutical compositions comprising the MASP-2 antibodies.

BACKGROUND OF INVENTION

The complement system comprises a complex array of enzymes and non-enzymatic proteins of importance to the function of the innate as well as the adaptive immune defense[1]. Until recently two modes of activation were known, the classical pathway initiated by antibody-antigen complexes and the alternative pathway initiated by certain structures on microbial surfaces. A third, novel antibody-independent pathway of complement activation has been described[2]. This pathway is initiated when mannan-binding lectin (MBL, first described as mannan-binding protein[3], MBP, see Ezekowitz, U.S. Pat. No. 5,270,199) binds to carbohydrates and is known as the MBLectin pathway.

MBL is structural related to the C1q subcomponent of component C1 of complement, and it appears that MBL activates the complement system via an associated serine protease termed MASP[4] or p100[5], which is similar to the C1 r and C1 s components of the classical pathway. The new complement activation pathway is called the MBLectin pathway. According to the mechanism postulated for this pathway, MBL binds to specific carbohydrate structures found on the surface of a range of microorganisms including bacteria, yeast, parasitic protozoa and viruses[5], and its antimicrobial activity results from activation of the terminal, lytic complement pathway components[7] or promoting phagocytosis[8].

MASPs (MBL-associated serine protease) are serine proteases similar in structure to C1 r and C1 s of the complement pathway. MASP-1 has a histidine loop structure of the type found in trypsin and trypsin-like serine proteases. MASP-1 has been found to be involved in complement activation by MBL. A cDNA clone encoding MASP-1 has been reported that encodes a putative leader peptide of 19 amino acids followed by 680 amino acid residues predicted to form the mature peptide.

MASP-2 (MBL-associated serine protease 2)[22] is a serine protease also similar in structure to C1 r and C1 s of the complement pathway. Like these, and contrary to MASP1, it has no histidine loop structure of the type found in trypsin and trypsin-like serine proteases. MASP-2 has been found to be involved in complement activation by MBL.

Antibodies to MASP-2 has been described in the prior art. WO 02/06460 describes human MASP-2. The document furthermore describes antibodies to MASP-2 raised by immunising rabbits with the N-terminal 19 amino acids of human MASP-2 or chickens with aa 505 to 523 and aa 538 to 556 of human MASP-2.

SUMMARY OF INVENTION

Interestingly, the inventors of the present invention have recognised that inhibition of the MBLectin pathway may be desirable in the treatment of a number of clinical conditions. However, specific inhibitors of the MBLectin pathway are not well characterised in the prior art and therefore an unmet need of specific inhibitors exists.

The present invention discloses that antibodies to the C-terminal part of MASP-2 are capable of inhibiting the activity of MASP-2 more efficiently than antibodies to the N-terminal part of MASP-2. The invention furthermore discloses MASP-2 epitopes, wherein antibodies recognising said epitopes are in particularly useful for inhibiting the activity of MASP-2. Preferred epitopes are describes herein below.

In one aspect the invention relates to an antibody or a functional equivalent thereof specifically recognising and binding at least part of an epitope recognised by one or more reference antibodies selected from the group consisting of
  i the monoclonal antibody produced by the hybridoma cell line deposited under the deposition number 03050904;
  ii the monoclonal antibody produced by the hybridoma cell line designated M0545YM029;
  iii the monoclonal antibody produced by the hybridoma cell line designated M0545YM035;
  iv the monoclonal antibody produced by the hybridoma cell line designated M0545YM046; and
  v the monoclonal antibody produced by the hybridoma cell line designated M0545YM048.

Accordingly, it is an objective of the present invention to provide antibodies or functional equivalents thereof specifically recognising and binding an epitope within the C-terminal part of MASP-2 or a functional homologue thereof.

It is furthermore an objective of the present invention to provide isolated polypeptides comprising a C-terminal fragment of MASP-2, said polypeptide being useful for raising antibodies to epitopes within the C-terminus of MASP-2. In particular, the isolated polypeptides from the C-terminal part of MASP-2 or a functional homologue thereof, may be polypeptides comprising or consisting of:

i. the EGF, CUB2, CCP1, CCP2 and serine protease domains; or
ii. the CUB2, CCP1, CCP2 and serine protease domains; or
iii. the CCP1 domain; or
iv. the CCP2 domain; or
the CCP1, and CCP2 domain It is furthermore an objective of the present invention to provide methods of producing an antibody inhibiting MASP-2 activity, by immunising an animal, preferably a mammal, with isolated polypeptides comprising a C-terminal fragment of MASP-2, said polypeptide being useful for raising antibodies to epitopes within the C-terminus of MASP-2. In particular, the isolated polypeptides from the C-terminal part of MASP-2 or a functional homologue thereof, may be polypeptides comprising or consisting of:

v. the EGF, CUB2, CCP1, CCP2 and serine protease domains; or
vi. the CUB2, CCP1, CCP2 and serine protease domains; or
vii. the CCP1 domain and the serine protease domain; or
viii. the CCP2 domain and the serine protease domain; or
ix. the CCP1, CCP2 and the serine protease domains
x. the serine protease domain It is a further objective of the present invention to provide methods of producing an antibody specifically recognising and binding an epitope within the C-terminal part of MASP-2 or a functional homologue thereof, comprising the step of administering to a mammal the C-terminal part of MASP-2 or a fragment thereof or a functional homologue thereof. Antibodies produced according to the method are also disclosed by the invention.

It is an even further objective of the invention to provide methods of inhibiting the activity of MASP-2 comprising the steps of 1) Providing a composition comprising MASP-2;
2) Providing a MASP-2 antibody according to the invention;
3) Incubating said composition with said antibody, thereby inhibiting MASP-2 activity Inhibition of MASP-2 will lead to inhibition of complement activation, preferably to inhibition of the MBLectin pathway. Accordingly, antibodies inhibiting the activity of MASP-2 may be used to inhibit activation of the MBLectin pathway and accordingly, said antibodies may be useful for treatment of clinical conditions characterised by improper activation of complement, preferably improper activation of the MBLectin pathway.

Hence, the invention also relates to methods of inhibiting the MBLectin pathway, preferably said methods involv the use of antibodies to MASP-2, capable of inhibiting the activity of MASP-2.

It is a still further objective of the present invention to provide pharmaceutical compositions comprising MASP-2 antibodies or functional equivalents thereof recognising an epitope within the C-terminal part of MASP-2 together with pharmaceutically acceptable excipients.

It is yet another objective of the present invention to provide a medicament for treatment of a clinical condition comprising an antibody or a functional equivalent thereof recognising an epitope within the C-terminal part of MASP-2 as an active ingredient.

It is also an objective of the present invention to provide methods of treatment of a clinical condition comprising administering to an individual in need thereof a therapeutically effective dosage of an antibody or a functional equivalent thereof recognising an epitope within the C-terminus of MASP-2.

It is furthermore an objective of the present invention to provide uses of antibodies or functional equivalents thereof recognising an epitope within the C-terminal part of MASP-2, for the preparation of a medicament for the treatment of a clinical condition in an individual in need thereof.

DESCRIPTION OF DRAWINGS

FIG. 2 shows an alignment of the human MASP-1 (SEQ ID NO:15), MASP-2 (SEQ ID NO:14, C1r (SEQ ID NO:16) and C1s (SEQ ID NO:17) sequences indicating the presence of the individual domains in MASP-2. Amino acids conserved in the four proteins are furthermore indicated by asterisk.

FIG. 10 shows an alignment between sequences of the heavy chain of the Ni-moAb101 antibody (DWE16140-1con (SEQ ID NO:29), DWE16140-2con (SEQ ID NO:30), DWE16140-3con (SEQ ID NO:31), DWE16140-4con (SEQ ID NO:27), DWE16140-5con (SEQ ID NO:28), and DWE16140-8con (SEQ ID NO:32)) together with homologous sequences P18525 (SEQ ID NO:22), P18526 (SEQ ID NO:23), P18529 (SEQ ID NO:24), P01764 (SEQ ID NO:25), P01783 (SEQ ID NO:26), P01868 (SEQ ID NO:33), P01869 (SEQ ID NO:34), P20759 (SEQ ID NO:35) and P20760 (SEQ ID NO:36) identified by BLAST searches.

FIG. 11 shows an alignment between sequences of the light chain of the NimoAb101 antibody (DWE16140-6con (SEQ ID NO:37), DWE16140-7con (SEQ ID NO:38), DWE16140-9con (SEQ ID NO:39) and DWE16140-10con (SEQ ID NO:40)) together with homologous sequences P01594 (SEQ ID NO: 41), P01595 (SEQ ID NO: 42), P01635 (SEQ ID NO: 43), P01636 (SEQ ID NO: 44), P01637 (SEQ ID NO: 45), P01835 (SEQ ID NO: 46), P01836 (SEQ ID NO: 47), and P01837 (SEQ ID NO: 48) identified by BLAST searches.

Figure 1:
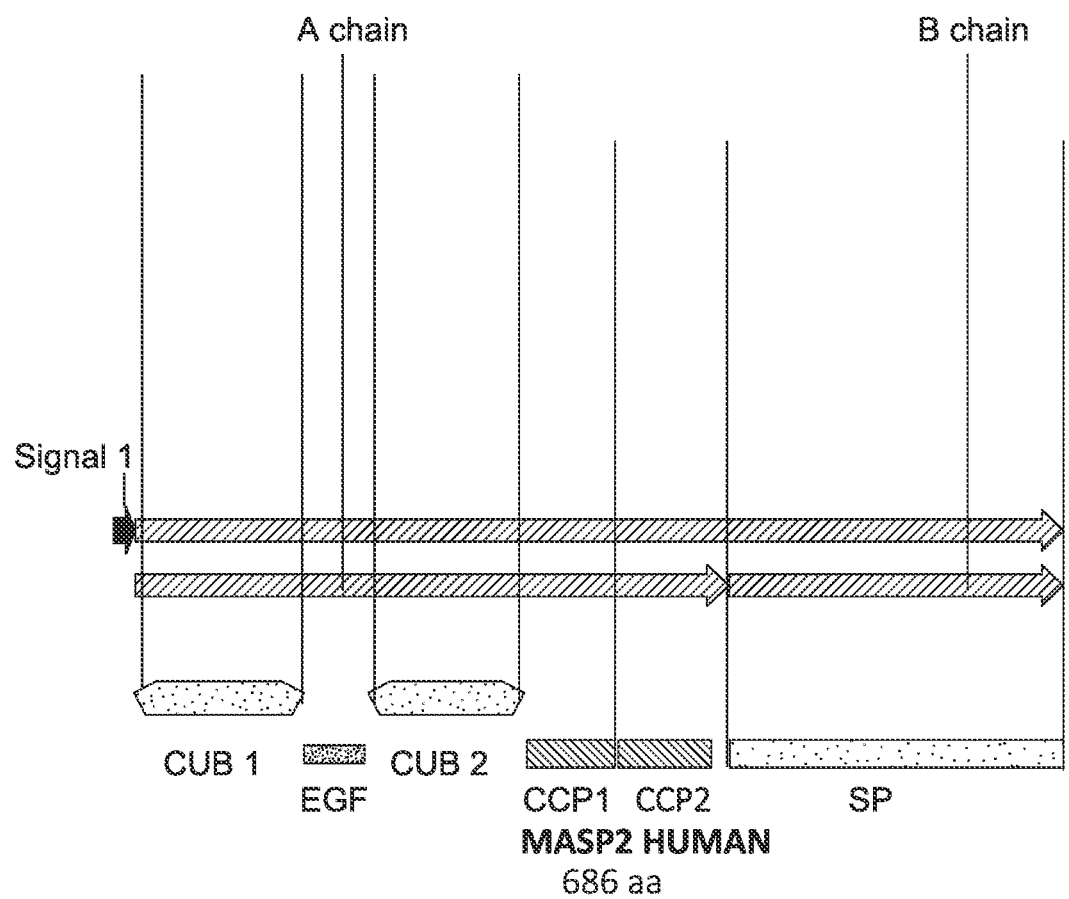
FIG. 1 depicts a schematic representation of MASP-2 indicating the individual domains.

| Sequence listing | |
|---|---|
| SEQ ID NO: 1 | Human MASP-2 |
| SEQ ID NO: 2 | Part of heavy chain of NimoAb101 including the variable region |

-continued

Sequence listing

| | |
|---|---|
| SEQ ID NO: 3 | Part of light chain of NimoAb101 including the variable region |
| SEQ ID NO: 4 | Part of heavy chain of NimoAb101 including the variable region |
| SEQ ID NO: 5 | Part of light chain of NimoAb101 including the variable region |
| SEQ ID NO: 6 | CDR1 of heavy chain (also designated H1) of NimoAb101 |
| SEQ ID NO: 7 | CDR2 of heavy chain (also designated H2) of NimoAb101 |
| SEQ ID NO: 8 | CDR3 of heavy chain (also designated H3) of NimoAb101 |
| SEQ ID NO: 9 | CDR1 of light chain (also designated L1) of NimoAb101 |
| SEQ ID NO: 10 | CDR2 of light chain (also designated L2) of NimoAb101 |
| SEQ ID NO: 11 | CDR3 of light chain (also designated L3) of NimoAb101 |
| SEQ ID NO: 12 | PCR primer |
| SEQ ID NO: 13 | PCR primer |
| SEQ ID NO: 14 | MASP-2 (FIG. 2) |
| SEQ ID NO: 15 | MASP-1 (FIG. 2) |
| SEQ ID NO: 16 | C1r (FIG. 2) |
| SEQ ID NO: 17 | C1s (FIG. 2) |
| SEQ ID NO: 18 | Nucleotide sequence encoding the variable region of the light chain of the NimoAb101 antibody (DWE16140-6cons, FIG. 8) |
| SEQ ID NO: 19 | Variable region of the light chain of the NimoAb101 antibody (DWE16140-6cons, FIG. 8) |
| SEQ ID NO: 20 | Nucleotide sequence encoding the variable region of the heavy chain of NimoAb101 antibody (DWE16140-3consRev, FIG. 9) |
| SEQ ID NO: 21 | Variable region of the heavy chain of NimoAb101 antibody (DWE16140-3consRev, FIG. 9) |
| SEQ ID NO: 22 | P18525 (FIG. 10) |
| SEQ ID NO: 23 | P18526 (FIG. 10) |
| SEQ ID NO: 24 | P18529 (FIG. 10) |
| SEQ ID NO: 25 | P01764 (FIG. 10) |
| SEQ ID NO: 26 | P01783 (FIG. 10) |
| SEQ ID NO: 27 | DWE16140-4con (FIG. 10) |
| SEQ ID NO: 28 | DWE16140-5con (FIG. 10) |
| SEQ ID NO: 29 | DWE16140-1con (FIG. 10) |
| SEQ ID NO: 30 | DWE16140-2con (FIG. 10) |
| SEQ ID NO: 31 | DWE16140-3con (FIG. 10) |
| SEQ ID NO: 32 | DWE16140-8con (FIG. 10) |
| SEQ ID NO: 33 | P01868 (FIG. 10) |
| SEQ ID NO: 34 | P01869 (FIG. 10) |
| SEQ ID NO: 35 | P20759 (FIG. 10) |
| SEQ ID NO: 36 | P20760 (FIG. 10) |
| SEQ ID NO: 37 | DWE16140-6con (FIG. 11) |
| SEQ ID NO: 38 | DWE16140-7con (FIG. 11) |
| SEQ ID NO: 39 | DWE16140-9con (FIG. 11) |
| SEQ ID NO: 40 | DWE16140-10con (FIG. 11) |
| SEQ ID NO: 41 | P01594 (FIG. 11) |
| SEQ ID NO: 42 | P01595 (FIG. 11) |
| SEQ ID NO: 43 | P01635 (FIG. 11) |
| SEQ ID NO: 44 | P01636 (FIG. 11) |
| SEQ ID NO: 45 | P01637 (FIG. 11) |
| SEQ ID NO: 46 | P01835 (FIG. 11) |
| SEQ ID NO: 47 | P01836 (FIG. 11) |
| SEQ ID NO: 48 | P01837 (FIG. 11) |

Definitions

The term "C-terminal part of MASP-2" refers to the C-terminus of MASP-2 comprising the EGF, CUB2, CCP1, CCP2 and serine protease domains, wherein the C-terminal part of MASP-2 does not include the CUB1 domain.

The term "epitope" refers to a specific site on a compound, i.e. a protein to which a certain antibody specifically binds. An epitope may be linear, i.e. a peptide or an epitope may be a three dimensional structure.

DETAILED DESCRIPTION OF THE INVENTION

Antibodies

It is one aspect of the present invention to provide antibodies or functional equivalents thereof specifically recognising and binding an epitope within the C-terminal part of MASP-2 or a functional homologue thereof. The epitope may be any of the epitopes mentioned herein below.

The antibody or functional equivalent thereof may be any antibody known in the art, for example a polyclonal or a monoclonal antibody derived from a mammal or a synthetic antibody, such as a single chain antibody or hybrids comprising antibody fragments. Furthermore, the antibody may be mixtures of monoclonal antibodies or artificial polyclonal antibodies. In addition functional equivalents of antibodies may be antibody fragments, in particular epitope binding fragments. Furthermore, antibodies or functional equivalent thereof may be small molecule mimic, micking an antibody. Naturally occurring antibodies are immunoglobulin molecules consisting of heavy and light chains. In preferred embodiments of the invention, the antibody is a monoclonal antibody.

Monoclonal antibodies (Mab's) are antibodies, wherein every antibody molecule are similar and thus recognises the same epitope. Monoclonal antibodies are in general produced by a hybridoma cell line. Methods of making monoclonal antibodies and antibody-synthesizing hybridoma cells are well known to those skilled in the art. Antibody producing hybridomas may for example be prepared by fusion of an antibody producing B lymphocyte with an immortalized B-lymphocyte cell line. Monoclonal antibodies according to the present invention may for example be prepared as described in Antibodies: A Laboratory Manual, By Ed Harlow and David Lane, Cold Spring Harbor Laboratory Press, 1988. Said monoclonal antibodies may be derived from any suitable mammalian species, however frequently the monoclonal antibodies will be rodent antibodies for example murine or rat monoclonal antibodies. It is preferred that the antibodies according to the present invention are monoclonal antibodies or derived from monoclonal antibodies.

Polyclonal antibodies is a mixture of antibody molecules recognising a specific given antigen, hence polyclonal antibodies may recognise different epitopes within said antigen. In general polyclonal antibodies are purified from serum of a mammal, which previously has been immunized with the antigen. Polyclonal antibodies may for example be prepared by any of the methods described in Antibodies: A Laboratory Manual, By Ed Harlow and David Lane, Cold Spring Harbor Laboratory Press, 1988. Polyclonal antibodies may be derived from any suitable mammalian species, for example from mice, rats, rabbits, donkeys, goats, sheeps, cows or camels. The antibody is preferably not derived from a non-mammalian species, i.e. the antibody is for example preferably not a chicken antibody. The antibody may also for example be an artificial polyclonal antibody as for example described in U.S. Pat. Nos. 5,789,208 or 6,335,163, both patent specifications are hereby incorporated by reference into the application in their entirety.

In one embodiment of the invention the antibody is a human antibody, such as a human monoclonal antibody. Human antibodies may be made to human target molecules for example by protein engineering, by selection from synthetic libraries, or by immunization of transgenic mice carrying human antibody genes.

Alternatively, the antibody may be a humanised antibody. Humanised antibodies are in general chimeric antibodies comprising regions derived from a human antibody and regions derived from a non-human antibody, such as a rodent antibody. Humanisation (also called Reshaping or CDR-grafting) is a well-established technique for reducing the immunogenicity of monoclonal antibodies (mAbs) from xenogeneic sources (commonly rodent) and for improving their activation of the human immune system. frameworks in which to graft the rodent CDRs. The term "humanised antibody molecule" (HAM) is used herein to describe a molecule having an antigen binding site derived from an immunoglobulin from a non-human species, whereas some or all of the remaining immunoglobulin-derived parts of the molecule is derived from a human immunoglobulin. The antigen binding site may comprise: either a complete variable domain from the non-human immunoglobulin fused onto one or more human constant domains; or one or more of the complementarity determining regions (CDRs) grafted onto appropriate human framework regions in the variable domain. One method for humanising MAbs related to production of chimeric antibodies in which an antigen binding site comprising the complete variable domains of one antibody are fused to constant domains derived from a second antibody, preferably a human antibody. Methods for carrying out such chimerisation procedures are for example described in EP-A-0 120 694 (Celltech Limited), EP-A-0 125 023 (Genentech Inc.), EP-A-0 171 496 (Res. Dev. Corp. Japan), EP-A-0173494 (Stanford University) and EP-A-0 194 276 (Celltech Limited). A more complex form of humanisation of an antibody involves the re-design of the variable region domain so that the amino acids constituting the non-human antibody binding site are integrated into the framework of a human antibody variable region (Jones et al., 1986).

The antibodies according to the present invention may also be recombinant antibodies. Recombinant antibodies are antibodies or fragments thereof or functional equivalents thereof produced using recombinant technology. For example recombinant antibodies may be produced using a synthetic library or by phage display. Recombinant antibodies may be produced according to any conventional method for example the methods outlined in "Recombinant Antibodies", Frank Breitling, Stefan Dübel, Jossey-Bass, September 1999.

The antibodies according to the present invention may also be bispecific antibodies, i.e. antibodies specifically recognising two different epitopes. Bispecific antibodies may in general be prepared starting from monoclonal antibodies, or from recombinant antibodies, for example by fusing two hybridoma's in order to combine their specificity, by Chemical crosslinking or using recombinant technologies. Antibodies according to the present invention may also be tri-specific antibodies.

Functional equivalents of antibodies may in one preferred embodiment be a fragment of an antibody, preferably an antigen binding fragment or a variable region. Examples of antibody fragments useful with the present invention include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Preferred antibody fragments retain some or essential all the ability of an antibody to selectively binding with its antigen or receptor. Some preferred fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule and can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

In one embodiment of the present invention the antibody is a single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "scFv" antibody fragments. Generally, the Fv polypeptide further comprises a polypeptide linker between the VH and VL domains that enables the scFv to form the desired structure for antigen binding.

The antibody may also be selected for useful properties, for example it may be desirable to control serum half life of the antibody. In general, complete antibody molecules have a very long serum persistence, whereas fragments (<60-80 kDa) are filtered very rapidly through the kidney. Glycosylation on complete antibodies in general, prolongs serum persistence. Hence, if long term action of the MASP-2 antibody is desireable, the MASP-2 antibody is preferably a complete antibody, whereas if shorter action of the MASP-2 antibody is desirable, an antibody fragment might be preferred.

In another embodiment of the present invention the functional equivalent of an antibody is a small molecule mimic, mimicking an antibody.

Preferred antibodies within the scope of the present invention are antibodies or functional equivalents thereof capable of inhibiting the function of MASP-2. The activity of MASP-2 may be the serine protease activity of MASP-2, such as serine protease activity to C4 and/or to C2. In particular, antibodies or functional equivalents thereof capable of inhibiting the serine protease activity of MASP-2 are preferred. Even more preferred are antibodies or functional equivalents thereof capable of inhibiting C4 deposition of MBL-MASP-2 complexes. Yet more preferred antibodies according to the present invention are antibodies or functional equivalents thereof capable of inhibiting C4 deposition in full serum. Yet more preferred antibodies or functional equivalents thereof are capable of inhibiting C4 deposition in full serum from individuals with C4 disposition activity. Useful assays for determining C4 deposition are described herein below.

In addition, preferred antibodies, are antibodies or functional equivalents thereof capable of inhibiting C2 deposition of MBL-MASP-2 complexes. Yet more preferred antibodies according to the present invention are antibodies or functional equivalents thereof capable of inhibiting C2 deposition in full serum. Yet more preferred antibodies or functional equivalents thereof are capable of inhibiting C2 deposition in full serum from individuals with C2 disposition activity. Useful assays for determining C2 deposition are described herein below.

Hence, preferred antibodies or functional equivalents thereof are capable of inhibiting C4 and/or C2 deposition in full serum to less than 50%, such as less than 40%, for example less than 30%, such as less than 25%, for example less than 20%, such as less than 15%, for example less than 10%, such as less than 5% of control C4 deposition. Preferably, the antibody is capable of inhibiting C4 deposition in full serum to less than 30%, preferably less than 25%, more preferably less than 20%, even more preferably less than 15%, yet more preferably less than 10%. Alternatively or in addition, preferred antibodies are capable of inhibiting C2 deposition in full serum to less than 30%, preferably less than 25%, more preferably less than 20%, even more preferably less than 15%, yet more preferably less than 10%.

In one very preferred embodiment of the invention the antibody is selected from the group of monoclonal antibodies produced by the hybridoma cell lines deposited under accession number 03050904. Furthermore, the functional equivalents may be fragments, preferably binding fragments of said antibodies.

In one embodiment of the present invention the antibody or functional equivalent thereof comprises specific hypervariable regions, designated CDR. Preferably, the CDRs are CDRs according to the Kabat CDR definition. CDRs or hypervariable regions may for example be identified by sequence alignment to other antibodies. Preferably, the antibody or functional equivalent thereof comprises at least one, more preferably at least 2, even more preferably all three of the following heavy chain CDRs:
1. H1 of the DWE16140-4con indicated in FIG. 10 (SEQ ID 6);
2. H2 of the DWE16140-4con indicated in FIG. 10 (SEQ ID 7);
3. H3 of the DWE16140-4con indicated in FIG. 10 (SEQ ID 8)

More preferably, the antibody or functional equivalent thereof comprises a heavy chain comprising or consisting of a sequence which is at least 95%, more preferably at least 98%, even more preferably at least 99% homologous or identical to SEQ ID 4. Yet more preferably, the antibody or functional equivalent thereof comprises a heavy chain comprising or consisting of the sequence set forth in SEQ ID 4.

Even more preferably the antibody or functional equivalent thereof comprises a heavy chain comprising or consisting of a sequence which is at least 95%, yet more preferably at least 98%, even more preferably at least 99% homologous or identical to SEQ ID NO:2. Yet more preferably the heavy chain consists of the sequence DWE16140-4 (SEQ ID NO:27) of FIG. 10.

% homology may be determined as described herein for functional homologues of MASP-2. Most preferably, the antibody or functional equivalent thereof comprises a heavy chain comprising or consisting of the sequence set forth in SEQ ID 2. Preferably, said antibody or functional equivalent thereof is capable of specifically recognising the epitope recognised by the antibody designated NimoAb101.

In another embodiment of the present invention the antibody or functional equivalent thereof comprises specific hypervariable regions, designated CDR. Preferably, the CDRs are CDRs according to the Kabat CDR definition. Preferably, the antibody or functional equivalent thereof comprises at least one, more preferably at least 2, even more preferably all three of the following light chain CDRs:
4. L1 of the DWE16140-10con indicated in FIG. 11 (SEQ ID 9);
5. L2 of the DWE16140-10con indicated in FIG. 11 (SEQ ID 10);
6. L3 of the DWE16140-10con indicated in FIG. 11 (SEQ ID 11)

More preferably, the antibody or functional equivalent thereof comprises a light chain comprising or consisting of a sequence which is at least 95%, more preferably at least 98%, even more preferably at least 99% homologous or identical to SEQ ID 5. Yet more preferably, the antibody or functional equivalent thereof comprises a light chain comprising or consisting of the sequence set forth in SEQ ID 5.

Even more preferably, the antibody or functional equivalent thereof comprises a light chain comprising or consisting of a sequence which is at least 95%, yet more preferably at least 98%, even more preferably at least 99% homologous or identical to SEQ ID NO:3. % homology may be determined as described herein for functional homologues of MASP-2. More preferably, the antibody or functional equivalent thereof comprises a light chain comprising or consisting of the sequence set forth in SEQ ID NO:3. Yet more preferably, the light chain consists of the sequence DWE16140-10con (SEQ ID NO:39) of FIG. 11. Preferably, said antibody or functional equivalent thereof is capable of specifically recognizing the epitope recognized by the antibody designated NimoAb101.

In a preferred embodiment the antibody or functional equivalent thereof comprises the CDRs of the heavy chain and the CDRs of the light chain described herein above. More preferably, the antibody or functional equivalent thereof comprises the variable region of the heavy chain described above and the variable region of the light chain described above. Even more preferably, the antibody or functional equivalent thereof comprises the heavy chain described herein above and the light chain described herein above. Thus, in a very preferred embodiment the invention relates to an antibody comprising one or more, preferably at least 2, even more preferably at least 3, yet more preferably at least 4, even more preferably at least 5, yet more preferably all 6 CDRs selected from the group consisting of
1) CDR1 of the heavy chain of SEQ ID 6;
2) CDR2 of the heavy chain of SEQ ID 7;
3) CDR3 of the heavy chain of SEQ ID 8;
4) CDR1 of the light chain of SEQ ID 9;
5) CDR1 of the light chain of SEQ ID 10; and
6) CDR1 of the light chain of SEQ ID 11.

or a functional equivalent thereof. This antibody furthermore, preferably is capable of inhibiting MASP-2 activity and/or capable of specifically recognising a MASP-2 epitope as described herein below.

MASP-2 Epitopes and Peptides

Figure 2:
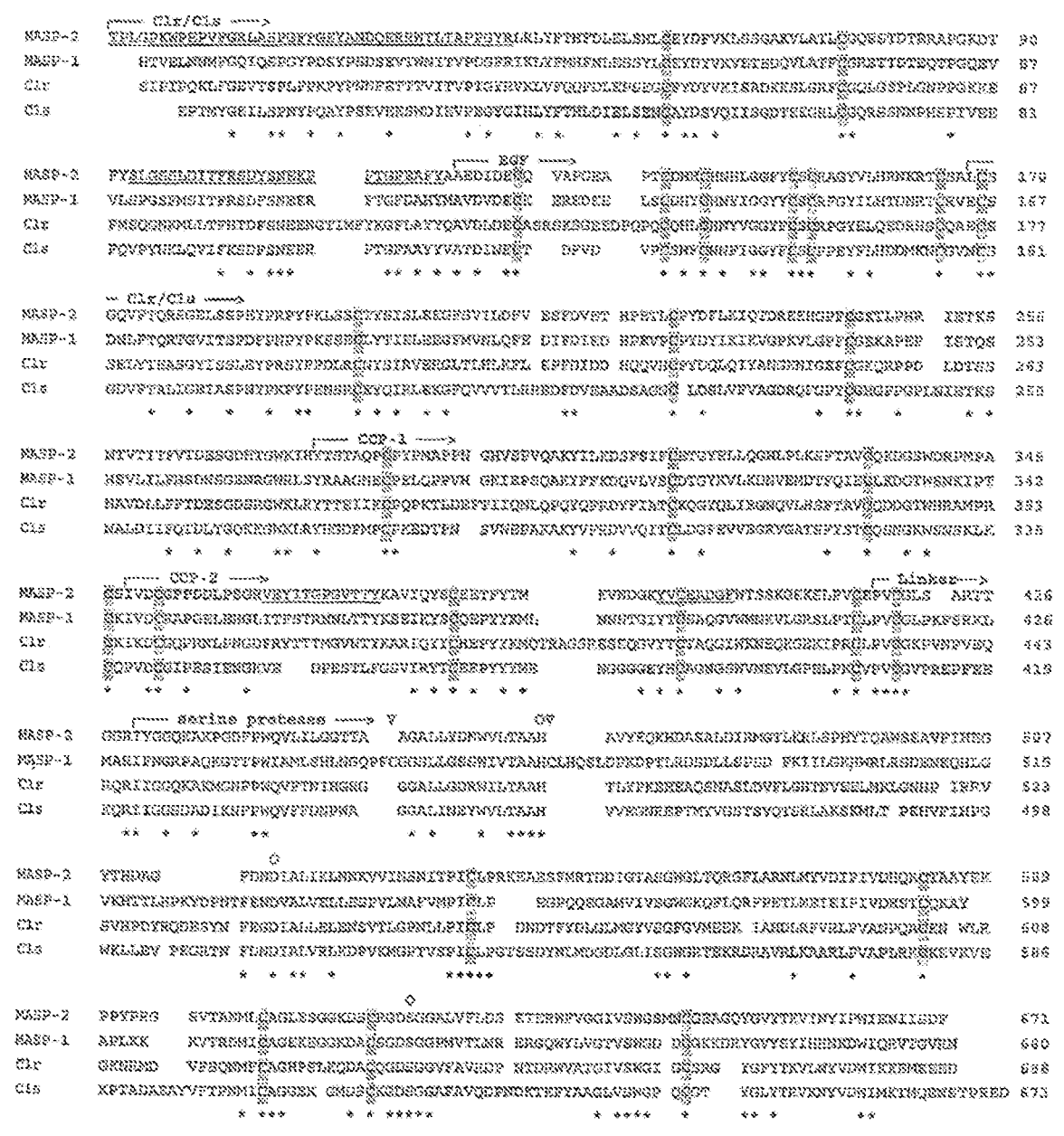

The MASP-2 protein comprises of a number of domains namely the CUB1, EGF, CUB2, CCP1, CCP2 and serine protease domains. A schematic presentation of MASP-2 is given in FIG. 1. Position of the individual domains within human MASP-2 is indicated in FIG. 2. It is believed that the domain responsible for association with MBL is situated in the N-terminus, whereas the serine protease domain is responsible for the serine protease activity of MASP-2. Surprisingly, antibodies raised to the C-terminus of MASP-2 are more efficient in inhibiting the activity of MASP-2 in full serum than other antibodies to MASP-2.

The antibodies and functional equivalents thereof according to the present invention specifically recognises an epitope within the C-terminal part of MASP-2. "Specifically recognises" means that the antibody binds to said epitope with significantly higher affinity than to any other molecule or part thereof. Preferably, the antibody only binds said epitope as detected by Western blotting or ELISA. To ensure that the antibody specifically recognises an epitope within a given fragment of MASP-2 said fragment may be used as antigen during generation of said antibody. It is preferred within the present invention, that the MASP-2 antigen used for immunisation is larger than 18 amino acids, for example at least 20, such as at least 25, for example at least 30 amino acids in length. By way of example, if the antibody should recognise an epitope within the CCP1, CCP2 and serine protease domains, a peptide consisting of the CCP1, CCP2 and serine protease domains may be used as antigen during generation of said antibody.

Preferably, the antibody or the functional equivalent thereof specifically recognises an epitope within the C-terminal part of MASP-2, wherein the C-terminal part comprises or even more preferably consists of the EGF, CUB2, CCP1, CCP2 and serine protease domains. In one embodiment of the invention, the C-terminal part of MASP-2 comprises or preferably consists of the CUB2, CCP1, CCP2 and serine protease domains. In another embodiment of the present invention the C-terminal part of MASP-2 comprises or preferably consists of the CCP1, CCP2 and serine protease domains. In yet another embodiment of the invention the C-terminal part of MASP-2 comprises or consists of the CCP2 and serine protease domains. In a preferred embodiment of the invention the C-terminal part of MASP-2 comprises or preferably consists of the serine protease domain.

In a still further embodiment of the invention the antibody specifically recognises and binds an epitope within a MASP-2 fragment that comprises or preferably consists of the CCP1 domain. In yet another embodiment of the invention the antibody specifically recognises and binds an epitope within a MASP-2 fragment that comprises or preferably consists of the CCP2 domain. In yet a further embodiment of the invention the antibody specifically recognises and binds an epitope within a MASP-2 fragment that comprises or preferably consists of the CCP1 and CCP2 domains.

By the term "MASP-2" is meant any MASP-2 molecule known to the person skilled in the art. Said MASP-2 may for example be derived from a mammal, for example MASP-2 may be derived from a human being. In a preferred embodiment of the present invention, MASP-2 is human MASP-2 as identified by SEQ ID 1 or a functional homologue thereof sharing at least 50%, preferably at least 60%, more preferably at least 70%, even more preferably at least 80%, yet more preferably at least 90%, yet even more preferably at least 95% homology or more preferably identity with SEQ ID 1. In a very preferred embodiment of the invention MASP-2 is MASP-2 of SEQ ID 1.

Hence, in a preferred embodiment the antibody specifically recognises and binds an epitope within a MASP-2 fragment that comprises or consists of aa 136 to 686 of SEQ ID 1 or a functional equivalent thereof, hence said fragment comprises the EGF, CUB2, CCP1, CCP2 and serine protease domains of human MASP-2.

In another embodiment of the invention the antibody specifically recognises and binds an epitope within a MASP-2 fragment that comprises or consists of aa 183 to 686 of SEQ ID 1 or a functional equivalent thereof. Said fragment thus comprises the CUB2, CCP1, CCP2 and serine protease domains of human MASP-2.

In yet another embodiment of the invention, the antibody specifically recognises and binds an epitope within a MASP-2 fragment that comprises or consists of aa 293 to 362 of SEQ ID 1 or a functional equivalent thereof. Said fragment comprises the CCP1 domain of human MASP-2.

In a further embodiment of the invention the antibody specifically recognises and binds an epitope within a MASP-2 fragment that comprises or consists of aa 293 to 431 of SEQ ID 1 or a functional homologue thereof. Said fragment comprises the CCP1 and CCP2 domains of human MASP-2.

In a still further embodiment of the present invention said antibody specifically recognises and binds an epitope within a MASP-2 fragment that comprises or consists of aa 363 to 431 of SEQ ID 1 or a functional equivalent thereof. Said fragment comprises the CCP2 domain of human MASP-2.

In an even further embodiment of the present invention the antibody specifically recognises and binds an epitope within a MASP-2 fragment that comprises or consists of aa 293 to 686 of SEQ ID 1 or a functional equivalent thereof. Said fragment comprises the CCP1, CCP2 and serine protease domains of human MASP-2.

In yet a further embodiment of the present invention the antibody specifically recognises and binds an epitope within a MASP-2 fragment that comprises or consists of aa 363 to 686 of SEQ ID 1 or a functional equivalent thereof. Said fragment(=CCP2, serine protease)

In a yet even further embodiment the antibody specifically recognises and binds an epitope within a MASP-2 fragment that comprises or consists of aa 445 to 686 of SEQ ID 1 or a functional equivalent thereof. Said fragment comprises the serine protease domain of human MASP-2.

In one embodiment of the present invention the epitope is not within aa 505 to 523 and aa 538 to 556 of SEQ ID 1.

In one preferred embodiment of the invention the antibody specifically recognises and binds an epitope within a MASP-2 fragment that comprises or preferably consists of aa 363 to 385, such a 370 to 390, for example 380 to 400, such a 390 to 410, for example 400 to 420, such a 410 to 430, for example 420 to 440, such a 430 to 450, for example 440 to 460, such a 450 to 470, for example 460 to 480, such a 470 to 490, for example 480 to 500, such a 490 to 510, for example 500 to 520, such a 510 to 530, for example 520 to 540, such a 530 to 550, for example 540 to 560, such a 550 to 570 for example 560 to 580, such a 570 to 590, for example 580 to 600, such a 590 to 610, for example 600 to 620, such a 610 to 630, for example 620 to 640, such a 630 to 650, for example 640 to 660, such a 650 to 670, for example 660 to 686 of SEQ ID 1, wherein said fragment at the most comprises 100, preferably at the most 80, more preferably at the most 60, even more preferably at the most 40 amino acids.

In another preferred embodiment, the antibody specifically recognises and binds an epitope within a MASP-2 fragment that comprises or preferably consists of aa 400 to 420, such a 410 to 430, for example 420 to 440, such a 430 to 450, for example 440 to 460, such a 450 to 470, for example 460 to 480, such a 470 to 490, for example 480 to 500, such a 490 to 510, for example 500 to 520, such a 510 to 530, for example 520 to 540, such a 530 to 550 of SEQ ID 1, wherein said fragment at the most comprises 100, preferably at the most 80, more preferably at the most 60, even more preferably at the most 40 amino acids.

In yet another preferred embodiment the antibody specifically recognises and binds an epitope within a MASP-2 fragment that comprises or preferably consists of aa 410 to 430, for example 420 to 440, such a 430 to 450, for example 440 to 460 of SEQ ID 1, wherein said fragment at the most comprises 100, preferably at the most 80, more preferably at the most 60, even more preferably at the most 40 amino acids.

In another very preferred embodiment the antibody specifically recognises and binds an epitope within a MASP-2 fragment that comprises or preferably consists of aa 420 to 440 or aa 430 to 450.

In one preferred embodiment of the present invention the antibodies or functional equivalents thereof specifically recognises the epitope recognised by the monoclonal antibody produced by the hybridoma cell line designated M0545YM035.

In another preferred embodiment of the present invention the antibodies or functional equivalents thereof specifically recognises the epitope recognised by the monoclonal antibody produced by the hybridoma cell line designated M0545YM029.

In another preferred embodiment of the present invention the antibodies or functional equivalents thereof specifically recognises the epitope recognised by the monoclonal antibody produced by the hybridoma cell line designated M0545YM046.

In another preferred embodiment of the present invention the antibodies or functional equivalents thereof specifically recognises the epitope recognised by the monoclonal antibody produced by the hybridoma cell line designated M0545YM048.

In one especially preferred embodiment of the present invention the antibodies or functional equivalents thereof specifically recognises the epitope recognised by the monoclonal antibody produced by the hybridoma cell line deposited under the deposition number 03050904.

In particular, the antibodies produced by the hybridoma cell line deposited under the deposition number 03050904 and the hybridoma cell lines designated M0545YM029 and M0545YM035 recognise overlapping epitopes. Thus it is preferred that the antibodies or functional equivalents thereof specifically recognises an epitope or part thereof recognised by one or more selected from the group consisting of:
 the monoclonal antibody produced by the hybridoma cell line deposited under the deposition number 03050904;
 the hybridoma cell line designated M0545YM029; and
 the hybridoma cell line designated M0545YM035

According to the present invention, when a given antibody recognises at least part of an epitope recognised by another given antibody, these two antibody are said to recognise the same or overlapping epitopes.

Different assays available to the person skilled in the art may be used to determine whether an antibody (also designated test antibody) recognises the same or an overlapping epitope as a particular monoclonal antibody (also designated reference antibody). Preferably, the assay involves the steps of:
 Providing MASP-2 or a fragment thereof comprising the epitope recognised by the reference antibody
 Add the test antibody and the reference antibody to the said MASP-2, wherein either the test antibody or the reference antibody is labelled with a detectable label. Alternatively, both antibodies may be labelled with different detectable labels
 Detecting the presence of the detectable label at MASP-2
 Thereby detecting whether the test antibody may displace the reference antibody If the reference antibody is displaced, the test antibody recognises the same or an overlapping epitope as the reference antibody. Thus if the reference antibody is labelled with a detectable label, then a low detectable signal at MASP-2 is indicative of displacement of the reference antibody. If the test antibody is labelled with a detectable label, then a high detectable signal at MASP-2 is indicative of displacement of the reference antibody. The MASP-2 fragment may preferably be immobilised on a solid support enabling facile handling. The detectable label may be any directly or indirectly detectable label, such as an enzyme, a radioactive isotope, a heavy metal, a coloured compound or a fluorescent compound. In example 5 in the section "MASP-2 competitive ELISA" herein below one very preferred method of determining whether a test antibody recognises the same or an overlapping epitope as a reference antibody is described. The person skilled in the art may easily adapt said method to the particular antibodies in question.

It is also an object of the present invention to provide isolated MASP-2 polypeptides useful as antigens for generation of MASP-2 antibodies, in particular MASP-2 antibodies capable of inhibiting the activity of MASP-2 in full serum. Said polypeptides may for example be used to immunise an animal in order to generate antibodies to the polypeptides.

Any C-terminal MASP-2 polypeptide may be used with the present invention, preferred polypeptides are however isolated polypeptides comprising or more preferably consisting of the EGF, CUB2, CCP1, CCP2 and serine protease domains of MASP-2. Hence, a very preferred MASP-2 polypeptide according to the invention comprises or even more preferably consists of aa 136 to 686 of SEQ ID 1 or a functional equivalent thereof.

In another embodiment, the isolated MASP-2 polypeptide comprises or preferably consists of the CUB2, CCP1, CCP2 and serine protease domains. Hence, a preferred MASP-2 polypeptide comprises or consists of aa 183 to 686 of SEQ ID 1 or a functional equivalent thereof.

In yet another embodiment of the present invention the isolated MASP-2 polypeptide comprises or preferably consists of the CCP1 domain. Hence, a preferred polypeptide comprises or even more preferably consists of aa 293 to 362 of SEQ ID 1 or a functional equivalent thereof.

In a further embodiment of the invention the isolated MASP-2 polypeptide comprises or preferably consists of the CCP2 domain. For example, the polypeptide may comprise or more preferably consist of aa 363 to 431 of SEQ ID 1 or a functional equivalent thereof.

In a yet further embodiment of the invention the isolated MASP-2 polypeptide comprises or preferably consists of the CCP1 and CCP2 domains. Hence, the polypeptide may comprises or even consist of aa 293 to 431 of SEQ ID 1 or a functional equivalent thereof.

The C-terminal MASP-2 polypeptides are preferably at the most 570 amino acids long, for example the polypeptides may be in the range of 20 to 570 amino acids, such as 30 to 500, for example 50 to 400, such as 100 to 300, for example 150 to 250 amino acids long.

Functional equivalents or functional homologues of MASP-2 polypeptides or fragments comprising a predetermined amino acid sequence, for example a fragment of the amino acid sequence outlined in SEQ ID 1 are defined as polypeptides comprising an amino acid sequence capable of being recognised by an antibody also capable of recognising the predetermined amino acid sequence. The terms "functional equivalent" and "functional homologue" are used interchangeably herein.

Functional homologues according to the present invention comprise polypeptides with an amino acid sequence, which are sharing a homology with the predetermined MASP-2 polypeptide sequences as outlined herein above. For example such polypeptides are at least about 40 percent, such as at least about 50 percent homologous, for example at least about 60 percent homologous, such as at least about 70 percent homologous, for example at least about 75 percent homologous, such as at least about 80 percent homologous, for example at least about 85 percent homologous, such as at least about 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with the predetermined polypeptide sequences as outlined herein above.

Homology may preferably be calculated by any suitable algorithm or by computerised implementations of such algorithms for example CLUSTAL in the PC/Gene program by Intelligenetics or GAP, BESTFIT, BLAST, FASTA and TFASTA in the Wisconsin Genetics Software Package, Genetics Computer Group (GCG). The homology between amino acid sequences may furthermore be calculated with the aid of well known matrices such as for example any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90.

Functional homologues according to the present invention are preferably polypeptides with an amino acid sequence, which is at least about 50 percent, preferably at least about 60 percent, more preferably at least about 70 percent, even more preferably at least about 75 percent, yet more preferably at least about 80 percent, even more preferably at least about 85 percent, yet more preferably at least about 90 percent, even more preferably at least 95 percent homologous, most preferably at least 98 percent identical with the predetermined MASP-2 polypeptide sequences as outlined herein above.

Functional homologues may comprise an amino acid sequence that comprises at least one substitution of one amino acid for any other amino acid. For example such a substitution may be a conservative amino acid substitution or it may be a non-conservative substitution. Preferably, said substitutions are conservative substitution.

A conservative amino acid substitution is a substitution of one amino acid within a predetermined group of amino acids for another amino acid within the same group, wherein the amino acids within a predetermined groups exhibit similar or substantially similar characteristics. Within the meaning of the term "conservative amino acid substitution" as applied herein, one amino acid may be substituted for another within groups of amino acids characterised by having
i) polar side chains (Asp, Glu, Lys, Arg, His, Asn, Gln, Ser, Thr, Tyr, and Cys)
ii) non-polar side chains (Gly, Ala, Val, Leu, Ile, Phe, Trp, Pro, and Met)
iii) aliphatic side chains (Gly, Ala Val, Leu, Ile)
iv) cyclic side chains (Phe, Tyr, Trp, His, Pro)
v) aromatic side chains (Phe, Tyr, Trp)
vi) acidic side chains (Asp, Glu)
vii) basic side chains (Lys, Arg, His)
viii) amide side chains (Asn, Gln)
ix) hydroxy side chains (Ser, Thr)
x) sulphur-containing side chains (Cys, Met), and
xi) amino acids being monoamino-dicarboxylic acids or monoamino-monocarboxylic-monoamidocarboxylic acids (Asp, Glu, Asn, Gln).

The addition or deletion of an amino acid may be an addition or deletion of from 2 to 5 amino acids, such as from 5 to 10 amino acids, for example from 10 to 20 amino acids, such as from 20 to 50 amino acids. However, additions or deletions of more than 50 amino acids, such as additions from 50 to 200 amino acids, are also comprised within the present invention.

In addition to the polypeptide compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates, including dimers or unrelated chemical moieties. Such functional equivalents are prepared by linkage of functionalities to groups which are found in fragment including at any one or both of the N- and C-termini, by means known in the art.

Functional equivalents may thus comprise fragments conjugated to aliphatic or acyl esters or amides of the carboxyl terminus, alkylamines or residues containing carboxyl side chains, e.g., conjugates to alkylamines at aspartic acid residues; O-acyl derivatives of hydroxyl group-containing residues and N-acyl derivatives of the amino terminal amino acid or amino-group containing residues, e.g. conjugates with Met-Leu-Phe. Derivatives of the acyl groups are selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups.

Functional homologues may furthermore be polypeptide encoded by a nucleic acid which is able to hybridise to the complementary strand of a nucleic acid sequence encoding the predetermined MASP-2 polypeptide sequences as outlined herein above under stringent conditions.

Stringent conditions as used herein shall denote stringency as normally applied in connection with Southern blotting and hybridisation as described e.g. by Southern E. M., 1975, J. Mol. Biol. 98:503-517. For such purposes it is routine practise to include steps of prehybridization and hybridization. Such steps are normally performed using solutions containing 6×SSPE, 5% Denhardt's, 0.5% SDS, 50% formamide, 100 µg/ml denatured salmon testis DNA (incubation for 18 hrs at 42° C.), followed by washings with 2×SSC and 0.5% SDS (at room temperature and at 37° C.), and a washing with 0.1×SSC and 0.5% SDS (incubation at 68° C. for 30 min), as described by Sambrook et al., 1989, in "Molecular Cloning/A Laboratory Manual", Cold Spring Harbor), which is incorporated herein by reference.

The epitope(s) recognised by a specific antibody may be determined by any conventional method, for example methods involving the use of mass spectrometry. Non-limiting examples of methods of epitope mapping using mass spectrometry include:

1. Baerga-Ortiz, A, Hughes, C A, Mandell, J G, Komives, E A: Epitope mapping of a monoclonal antibody against human thrombin by H/D-exchange mass spectrometry reveals selection of a diverse sequence in a highly conserved protein. *Protein Sci.* 11:1300-1308, 2002
2. Hochleitner, E O, Borchers, C, Parker, C, Bienstock, R J, Tomer, K B: Characterization of a discontinuous epitope of the human immunodeficiency virus (HIV) core protein p24 by epitope excision and differential chemical modification followed by mass spectrometric peptide mapping analysis.
3. Hochleitner, E O, Gorny, M K, Zolla-Pazner, S, Tomer, K B: Mass spectrometric characterization of a discontinuous epitope of the HIV envelope protein HIV-gp120 recognized by the human monoclonal antibody 1331A. *J. Immunol.* 164:4156-4161, 2000
4. Parker, C E, Tomer, K B: MALDI/MS-based epitope mapping of antigens bound to immobilized antibodies. *Mol. Biotechnol.* 20:49-62, 2002
5. Peter, J F, Tomer, K B: A general strategy for epitope mapping by direct MALDI-TOF mass spectrometry using secondary antibodies and cross-linking. *Anal. Chem.* 73:4012-4019, 2001
6. Van De, W J, Deininger, S O, Macht, M, Przybylski, M, Gershwin, M E: Detection of molecular determinants and epitope mapping using MALDI-TOF mass spectrometry. *Clin. Immunol. Immunopathol.* 85:229-235, 1997
7. Yu, L, Gaskell, S J, Brookman, J L: Epitope mapping of monoclonal antibodies by mass spectrometry: identification of protein antigens in complex biological systems. *J. Am. Soc. Mass Spectrom.* 9:208-215, 1998
8. Zhao, Y, Chalt, B T: Protein epitope mapping by mass spectrometry. *Anal. Chem.* 66:3723-3726, 1994

Methods of Preparing MASP-2 Antibodies

The antibodies and functional equivalents thereof may be produced by any suitable method known to the person skilled in the art.

One method of producing an antibody specifically recognising and binding an epitope within the C-terminal part of MASP-2 comprises the step of administering to a mammal the C-terminal part of MASP-2 or a fragment thereof or a functional homologue thereof. Said C-terminal part of MASP-2 or a fragment thereof or a functional homologue thereof may be any of the MASP-2 fragments and peptides described herein above. In particular, the MASP-2 fragment may be any of the MASP-2 fragments described herein above, wherein said fragments comprise an epitope. The C-terminal part of MASP-2 or fragment thereof or functional homologue thereof administrated to said mammal is also designated the "MASP-2 antigen" herein.

In one embodiment, the present invention relates to methods of producing an antibody capable of inhibiting the activity of MASP-2, wherein said antibody specifically recognises an epitope within the C-terminal part of MASP-2.

The MASP-2 antigen is preferably at least 18 amino acids in length, more preferably at least 20, even more preferably at least 25 amino acids in length.

The MASP-2 antigen may be administrated to said mammal more than once, such as twice, for example 3 times, such as 3 to 5 times, for example 5 to 10 times, such as 10 to 20 times, for example 20 to 50 times, such as more than 50 times. It is also possible that different MASP-2 antigens are administered to the same mammal, either simultaneously of sequentially in any order.

In general, the MASP-2 antigen will be in an aqueous solution or suspension prior to administration. Furthermore, the MASP-2 antigen may be mixed with one or more other compounds. For example, the MASP-2 antigen may be mixed with one or more suitable adjuvants and/or with one or more carriers.

Adjuvants are any substance whose admixture with an administered antigen increases or otherwise modifies the immune response to said antigen. Adjuvants may for example be selected from the group consisting of AlK $(SO_4)_2$, $AlNa(SO_4)_2$, $AlNH_4 (SO_4)$, silica, alum, $Al(OH)_3$, $Ca_3 (PO_4)_2$, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+ TDM+CWS) in a 2% squalene/Tween-80® emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from *Mycobacterium*, tuberculosis, substances found in *Corynebacterium parvum*, *Bordetella pertussis*, and members of the genus *Brucella*, liposomes or other lipid emulsions, Titermax, ISCOMS, Quil A, ALUN (see U.S. Pat. Nos. 58,767 and 5,554,372), Lipid A derivatives, choleratoxin derivatives, HSP derivatives, LPS derivatives, synthetic peptide matrixes or GMDP, Interleukin 1, Interleukin 2, Montanide ISA-51 and QS-21. Preferred adjuvants to be used with the invention include Freund's Complete Adjuvant (FCA), Freund's Incomplete Adjuvants.

Carriers are scaffold structures, e.g. a polypeptide or a polysaccharide, to which an antigen is capable of being associated. A carrier may be present independently of an adjuvant. The function of a carrier can for example be to increase the molecular weight of in particular MASP-2 antigen in order to increase the immunogenicity, to confer stability, to increase the biological activity, or to increase serum half-life. The carrier may be any suitable carrier known to the person skilled in the art, for example a protein or an antigen presenting cell. A carrier protein could be, but is not limited to keyhole limpet hemocyanin, serum proteins such as transferrin, bovine serum albumin, human serum albumin, thyroglobulin or ovalbumin, immunoglobulins, or hormones, such as insulin or palmitic acid.

The MASP-2 antigen may be administered by any suitable method, for example parenterally, orally or topically. Preferably, however the antigen is administered by injection, for example intramuscular, intradermal, intravenous or subcutaneous injection, more preferably by subcutaneous or intravenous injection.

The mammal may be any suitable mammal. Monoclonal antibodies are frequently prepared using a rodent, for example a mouse or a rat Polyclonal antibodies may be prepared by administering the MASP-2 antigen to any mammal, for example mice, rats, rabbits, donkeys, goats, sheeps, cows or camels. Antibodies according to the invention may also be mixtures of antibodies, such as mixtures of monoclonal antibodies, mixtures of polyclonal antibodies or both. Hence, it is also comprised within the invention that more than one kind of animal may be used.

If the antibody is a monoclonal antibody, antibody producing cells are usually isolated from said mammal subsequent to immunisation. The method may for example comprise the steps of isolating antibody producing cells from said mammal, preparing hybridoma cells from said antibody producing cells, cultivating said hybridomas and isolating antibodies produced by said hybridomas.

For example said cells may be isolated from said mammal 1 day, such as in the range of 2 to 10 days, for example in the range of 10 to 20 days, such as in the range of 20 to 40 days, for example in the range of 1 to 3 months, such as in the range of 3 to 6 months, for example in the range of 6 to 12 months, such as in the range of 12 to 24 months, for example more than 24 months after first administration of the MASP-2 antigen.

The antibody producing cells are in general B-cells and said cells may for example be isolated from said mammal by excising the spleen of said mammal.

Once the antibody producing cells have been isolated from said mammal, the cells may be fused with other cells in order to obtain hybridoma cells. Said cells may for example be cancer cells, such as cells derived from a leukaemia, for example myeloma cells. After fusion said hybridoma cells may be cultivated using standard cultivation protocols. The cultivation medium (supernatant) may be tested for the presence of suitable MASP-2 antibodies and hybridoma cells capable of producing suitable MASP-2 antibodies may be selected and cultivated.

Testing may be performed by any suitable method, for example methods detecting the presence of antibodies capable of associating with the MASP-2 antigen. Such methods include, but are not limited to Western blotting, ELISA (Enzyme-Linked Immunosorbent Assay), dot-blotting or TRIFMA. In addition or alternatively, said cultivation medium may be tested for the presence of MASP-2 antibodies capable of inhibiting MASP-2 activity. Suitable assays to determine MASP-2 activity are described herein below.

Once hybridoma cells capable of producing suitable MASP-2 antibodies have been identified, said cells may be cultivated using any standard protocol and antibodies produced by said cells may be purified. Purification of antibodies may be done using any standard protocol, for example purification using anti-Ig antibodies, protein G or protein A.

If the antibody is a polyclonal antibody, said antibody may for example be purified directly from serum from a mammal, immunised with the MASP-2 antigen. Purification may be done using any standard method, for example purification using anti-Ig antibodies, protein G or protein A.

Methods of preparing monoclonal antibodies, mixtures of monoclonal antibodies or polyclonal antibodies are for example described in Antibodies: A Laboratory Manual, By Ed Harlow and David Lane, Cold Spring Harbor Laboratory Press, 1988.

One non-limiting example of a method to prepare antibodies according to the present invention is described in example 1 herein below.

Depending of the nature of the antibody, several other methods may be employed.

In one embodiment of the invention the antibody may be produced using recombinant methods, for example protein engineering or by screening of libraries. Libraries may be synthetic libraries or libraries comprising natural material. One useful method is phage display. In general phage display, involves screening one or more phage libraries for phages encoding a useful antibody or functional equivalent thereof.

In another embodiment of the present invention, the methods involve use of animals, for example rodents, such as mice genetically engineered to produce chimeric antibodies or antibodies of another species, for example human antibodies. For example, transgenic animals, such as transgenic mice, carrying antibody genes from another species, such as human antibody genes, may be immunised with any pf the above mentioned MASP-2 fragments.

Antibody fragments may be produced by fragmentation of the antibodies according to the invention using any method known to the person skilled in the art. The methods include, but are not limited to digestion with one or more proteases, for example papain or pepsin, as well as reduction or a combination of both.

Inhibiting MASP-2 Activity

The present invention also relates to methods of inhibiting the activity of MASP-2. In particular, the methods may involve the steps of 1) Providing a composition comprising MASP-2;
2) Providing a MASP-2 antibody according to the invention;
3) Incubating said composition with said antibody, thereby inhibiting MASP-2 activity The composition may be any composition comprising MASP-2, for example serum. The MASP-2 antibody is preferably a MASP-2 antibody capable of inhibiting the activity of MASP-2.

Assays to Detect MASP-2 Activity

MASP-2 activity may be determined by any suitable assay. Useful assays include the in particular assays, wherein serine protease activity of MASP-2/MBL complexes are tested. Preferred assays, are assays determining inhibition of C2 and/or C4 deposition.

The assays may involved the steps of preparing a solid surface on which an MBL associating agent is immobilised, binding MBL/MASP-2 complexes to said MBL associating agent and screening for inhibition of MASP-2 catalysed reactions.

The solid surface may be any useful solid surface, for example microtiter wells. The MBL associating agent, may be any compound to which MBL binds with high affinity, for example MBL antibodies, mannan or mannose, preferably however it is mannan. The MBL/MASP-2 complexes may be derived from any suitable source, it may for example be recombinant MBL, recombinant MASP-2 or MBL and/or MASP-2 purified from serum. Recombinant MBL/MASP-2 may be full length MBL/MASP-2 or functional fragments thereof. Furthermore, recombinant MBL/MASP-2 may be attached to one or more other compounds, such as genetic tags. MBL and/or MASP-2 may be derived from any suitable species for example it may be human MBL/MASP-2. In one embodiment of the invention, the MBL/MASP-2 complexes are found in full serum and are not purified prior to performing the assay. Said assays then test inhibition of deposition of substrate, i.e. C4 in full serum. The MASP-2 catalysed reaction is preferably deposition of C2 and/or C4.

The antibody or functional equivalent thereof to be screened for inhibition activity is added to the bound MBL/MASP-2. The antibody may have been purified or it may be for example crude hybridoma cell culture supernatant. Controls without added antibody are preferably also performed. The antibody may be added in concentrations in the range of 1 µg/ml to 500 µg/ml, preferably in the range of 5 µg/ml to 400 µg/ml, more preferably in the range of 10
1 µg/ml to 300 µg/ml, even more preferably in the range of 15 µg/ml to 200 µg/ml, yet more preferably in the range of 20 to 100 µg/ml.

A MASP-2 substrate is added to the MBL/MASP-2 complexes. Preferably, said substrate is either C2 or C4 or a mixture of both. The substrate may be recombinantly produced or a serum derived substrate. The substrate may or may not have been purified prior to use, but preferably it is purified. In order to monitor deposition, the substrate, may be labeled with a detectable label, for example with an enzyme, a radioactive compound, a fluorescent compound, a dye, a heavy metal, a chemiluminescent compound or the like.

It is however preferred that deposition is detected using specific binding agent, such as an antibody, specifically recognising digested substrate. For example, antibodies recognising human complement C4c may be used. Said antibodies may be labelled, by a directly or indirectly detectable label. For example by an enzyme, a radioactive compound, a fluorescent compound, a dye, a heavy metal, a chemiluminescent compound or an affinity compound. Affinity compounds includes for example other antibodies or biotin, streptavidin.

The above mentioned steps may be performed in any useful order, i.e. substrate may be added before or simultaneously to inhibiting antibody, MBL/MASP-2 complexes may be mixed with the substrate and/or the inhibiting antibody prior to immobilisation on a solid surface etc. The steps may also be performed in the order described.

If MBL/MASP-2 complexes, substrate and antibody are mixed prior to immobilisation, then said mixture may be preincubated for a given time, for example preincubation may be in the range of 5 min to 2 hours. In general, MBL/MASP-2, substrate and antibody is premixed, when MBL/MASP-2 complexes are present in serum and have not previously been purified from serum.

In one preferred embodiment of the present invention, the activity of MASP-2 is determined using any of the methods described in examples 2 and 3. In particular, antibodies capable of inhibiting C4 deposition, should preferably be able to inhibit C4 deposition in at least one, preferably both of the methods described in example 2 and 3. Antibodies capable of inhibiting C4 deposition, should more preferably at least be able to inhibit C4 deposition according to the methods described in example 2, whereas antibodies capable of inhibiting C4 deposition in full serum should be capable of inhibiting C4 deposition in full serum as described in example 3.

Pharmaceutical Compositions and Administration Thereof.

In one embodiment the present invention relates to pharmaceutical compositions comprising the antibodies and functional equivalents thereof according to the invention. The invention furthermore relates to medicaments for treatment of a clinical condition comprising the antibody, methods of treatment of a clinical condition comprising administration of said antibody or use of said antibody for preparation of a medicament for treatment of a clinical condition.

The clinical condition may be any of the conditions mentioned herein below. The individual in need of administration of MASP-2 antibodies may be any individual suffering from said condition or at risk of acquiring said clinical condition. Preferably, the individual is a human being.

Treatment may be curative, palliative, ameliorating and/or prophylactic treatment.

The pharmaceutical compositions of the present invention preferably comprise a pharmaceutical effective amount of at least one antibody or functional equivalent thereof specifically recognising an epitope within the C-terminus of MASP-2 (herein above and below designated "MASP-2 antibody"). A pharmaceutical effective amount is an amount of MASP-2 antibody, which in induces the desired response in an individual receiving said pharmaceutical composition.

The pharmaceutically effective amount of the MASP-2 antibody depends on the individual to which it should be administered, in particular on the size of said individual as well as the clinical condition and the specific mode of administration. In general however, in the range of 1 mg to 5000 mg, preferably in the range of 10 mg to 3000 mg, more preferably in the range of 50 mg to 1000 mg, for example in the range of 100 mg to 750 mg, such as in the range of 150 mg to 500 mg, for example in the range of 200 mg to 400 mg, such as in the range of 250 mg to 350 mg, for example around 300 mg MASP-2 antibody should be administered to an adult human being per dose.

The composition of the present invention may be a pharmaceutical composition suitable for parenteral administration. Such compositions preferably, include aqueous and non-aqueous sterile injection solutions which may contain wetting or emulsifying reagents, anti-oxidants, pH buffering agents, bacteriostatic compounds and solutes which render the formulation isotonic with the body fluid, preferably the blood, of the individual; and aqueous and non-aqueous sterile suspensions which may include suspending agents or thickening agents. The pharmaceutical composition may be presented in unit-dose or multi-dose containers, for example, sealed ampoules and vials and may be stored in a freeze-dried condition requiring only the addition of the sterile liquid carrier immediately prior to use.

Preferably, the composition of the present invention comprises one or more suitable pharmaceutical excipients, which could be non-sterile or sterile, for use with cells, tissues or organisms, such as a pharmaceutical excipients suitable for administration to an individual. Such excipients may include, but are not limited to, saline, buffered saline, dextrose, water, glycerol, ethanol and combinations of these excipients in various amounts. The formulation should suit the mode of administration. The invention further relates to pharmaceutical kit of parts comprising one or more containers filled with one or more of the ingredients of the aforementioned compositions of the invention. Examples of non-aqueous excipients are propylene glycol, polyethylene glycol, vegetable oils such as olive oil, and injectable organic esters such as ethyl oleate.

Preferably, the pharmaceutical compositions of the present invention are prepared in a form which is injectable, either as liquid solutions or suspensions; furthermore solid forms suitable for solution in or suspension in liquid prior to injection are also within the scope of the present invention.

The preparation may be emulsified or the immunogenic determinant as well as the collectins and/or collectin homologues according to the present invention may be encapsulated in liposomes.

The MASP-2 antibody may be administered alone or in combination with other compounds, either simultaneously or sequentially in any order.

Administration could for example be parenteral injection or infusion, rapid infusion, nasopharyngeal absorption, dermal absorption, and enterally, such as oral administration. Parenteral injection could for example be intravenous, intramuscular, intradermal or subcutaneous injection. Preferably, said administration is parenterally by injection or infusion.

The MASP-2 antibody should be administered as often as required, hence the MASP-2 antibody may be administered more than once, such as at least two times, for example at least 3 times, such as at least 4 times, for example at least 5 times, such as in the range of 1 to 100 times, for example in the range of 1 to 50 times, such as in the range of 1 to 25 times, for example in the range of 1 to 10 times.

Preferably, there is at least 1 day between 2 administrations, such as at least 2 days, for example at least 3 days, such as at least 5 days, for example at least one week, such as at least 2 weeks, for example at least one month, such as at least 6 months, for example at least 1 year, such as at least 2 years, for example at least 3 years, such as at least 5 years, for example at least 10 years.

Clinical Conditions

The clinical condition according to the present invention may be any condition, which may be treated curative, ameliorating or prophylactic by administration of MASP-2 antibodies.

The clinical condition may be one preferred embodiment of the present invention be a chronic inflammatory disease. Chronic inflammatory diseases may for example be autoimmune inflammatory conditions.

Autoimmune inflammatory conditions (also designated "autoimmune disorders" herein) may be loosely grouped into those primarily restricted to specific organs or tissues and those that affect the entire body. Examples of organ-specific disorders (with the organ affected) include multiple sclerosis (myelin coating on nerve processes), type I diabetes mellitus (pancreas), Hashimotos thyroiditis (thyroid gland), pernicious anemia (stomach), Addison's disease (adrenal glands), myasthenia gravis (acetylcholine receptors at neuromuscular junction), rheumatoid arthritis (joint lining), uveitis (eye), psoriasis (skin), Guillain-Barre Syndrome (nerve cells) and Grave's disease (thyroid). Systemic autoimmune diseases include systemic lupus erythematosus, glomeronephritis and dermatomyositis.

In one embodiment of the present invention the preferred clinical condition is selected from the group consisting of rheumatoid arthritis and systemic lupus erythermatosis.

Other examples of autoimmune disorders include asthma, eczema, atopical dermatitis, contact dermatitis, other eczematous dermatitides, seborrheic dermatitis, rhinitis, Lichen planus, Pemplugus, bullous Pemphigoid, Epidermolysis bullosa, uritcaris, angioedemas, vasculitides, erythemas, cutaneous eosinophilias, Alopecia areata, atherosclerosis, primary biliary cirrhosis and nephrotic syndrome. Related diseases include intestinal inflammations, such as Coeliac disease, proctitis, eosinophilia gastroenteritis, mastocytosis, inflammatory bowel disease, Chrohn's disease and ulcerative colitis, as well as food-related allergies.

In another embodiment of the present invention the clinical condition is characterised by massive cell loss, for example due to apoptosis or necrosis. Said necrosis or apoptosis may be induced by a number of different factors.

In a preferred embodiment of the invention, the clinical condition is ischemia/reperfusion injury. Ischemia may arise from various different causes, for example after stroke, myocardial infarction, major surgery or organ transplantation. Thus, the clinical condition may be ischemia/reperfusion injury caused by for example stroke, myocardial infarction, major surgery or organ transplantation.

Hence, the clinical condition may be ischemia/reperfusion injury, which is a result of PTCA (percutaneous transluminal coronary angioplasty) or CABG (coronary artery bypass grafting). Furthermore, the clinical condition may be ischemia/reperfusion injury, which is a result of acute myocardial infarction or brain ischemia.

EXAMPLES

Example 1

Monoclonal Anti-MASP-2 Antibody:

Female Wistar rats (8 weeks old) were injected subcutaneous with 3 µg recombinant human MASP-2 CCP1-CCP2-serine protease domain (CCP1/2-SP) (Rossi et al., 2001) emulsified in complete Freund's adjuvant and boosted three times with the 3 µg CCP1/2-SP in incomplete Freund's adjuvant. Three days prior to removal of the spleen the rat was boosted intravenously with 3 µg CCP1/2-SP in saline.

Fusion of a suspension of spleen cells with mouse myeloma cells (X63-Ag8.653) and culture on mouse feeder cells were as described (Liu et al., 2001).

For the detection of anti-MASP-2 antibody in the supernatants, microtiter plates (FluoroNunc, Nunc, Kamstrup, Denmark) were coated with 1 µg mannan (Nakajima and Ballou, 1974) in 100 µl 15 mM $Na_2CO_3$, 35 mM $NaHCO_3$, 1.5 mM $NaN_3$, pH 9.6 (coating buffer) overnight at 4° C. Residual protein-binding sites were blocked by 200 µg human serum albumin (HSA) in 200 µl of 10 mM Tris-HCl, 140 mM NaCl, 1.5 mM $NaN_3$, pH 7.4 (TBS) for 1 hour at room temperature.

The wells were washed in TBS containing 0.05% (v/v) Tween 20 and 5 mM $CaCl_2$) (TBS/Tw/$Ca^{2+}$) followed by incubation overnight at 4° C. with 0.5 µg MBL/MASP preparation in 100 µl TBS/Tw/$Ca^{2+}$.

After wash, hybridoma supernatants diluted 5 fold in TBS/Tw/$Ca^{2+}$ were added to the wells and incubated for 2 hours at room temperature. Bound anti-MASP-2 antibodies were detected by adding 50 ng rabbit-anti rat Ig antibody (Dako, Glostrup, Denmark) labelled with europium (Perkin Elmer, Gaithersburg, USA) (Hemmila et al., 1984) in 100 µl TBS/Tw, 25 µM EDTA. After 1 hour at room temperature the wells were washed and bound europium was detected by the addition of 200 µl enhancement solution (Perkin Elmer), and reading the time resolved fluorescence on a DELFIA® fluorometer (Perkin Elmer). Selected positive cultures were cloned twice by limiting dilution and frozen in 60% (v/v) DMEM, 30% (v/v) fetal calf serum, 10% (v/v) DMSO.

An MBL/MASP preparation was separated on SDS-PAGE followed by blotting onto a PVDF membrane. The selected antibodies were tested for recognition of MASP-2 on the blot.

Inhibiting antibodies were identified by screening for inhibition of MASP-2 catalysed C4 deposition as described in example 2 herein below.

Culture supernatant of hybridoma cell lines producing the selected antibodies was centrifuged at 10,000 g for 15 minutes and the supernatant buffed with 10 mM $Na_2HPO_4$, 10 mM EDTA, pH 7. One hundred ml supernatant was passed through a 1 ml anti-bovine Ig column (5 mg anti-bovine Ig (Dako) per ml CNBr activated Sepharose 4B beads (Amersham Bioscience, Uppsala, Sweden)) equilibrated in 1.5 mM $KH_2PO_4$, 8.1 mM $Na_2HPO_4$, 137 mM NaCl, 2.7 mM KCl, pH 7.4 (PBS) with 10 mM EDTA (PBS/EDTA). The effluent was passed onto a 1 ml protein G Sepharose (Amersham Bioscience) column pre-washed with 0.1 M glycine, pH 2.5 and re-equilibrated with PBS/EDTA. The columns were washed with 30 ml PBS/EDTA and eluted with 0.1 M glycine pH 2.5. The eluate was collected in fractions of 0.5 ml into 40 µl 1 M Tris-HCL, pH 8.5.

Example 2

Assay for Inhibition of MASP-2 Catalysed C4 Deposition:

The assay is composed of three steps 1) preparation of mannan coated microtiter wells 2) binding of rMBL and rMASP-2 to mannan coated wells 3) screening for inhibition of MASP-2 catalysed C4 deposition.

1) Preparation of Mannan Coated Microtiter Wells:

96 wells microtiter plates (FluroNunc, Nalgene Nunc Int., Denmark) are coated with mannan (10 mg/L, Sigma Chemical Co., St. Louis, USA) in a coating buffer ($Na_2CO_3$: 3.18 g/L; $NaHCO_3$: 5.86 g/L; pH adjusted to 9.6 using HCl) over night at 4° C. Wells are washed twice in TBS (10 mM Tris, 150 mM NaCl, pH adjusted to 7.4 using HCl). Wells are then blocked by incubation for 1 hr at room temperature in a buffer as above except that 1 mg/mL of human albumin is added (State Serum Institute, Copenhagen Denmark). Wells are washed 3 times in TBST+$Ca^{2+}$ (10 mM Tris, 150 mM NaCl, 10 mM $CaCl_2$); 0.05% Tween 20, pH adjusted to 7.4 using HCl, from now on washing buffer) and are now ready for use.

2) Binding of rMBL and rMASP-2 to Mannan Coated Wells:

0.8 ng/well of recombinant purified human His-tagged MASP-2 and 1 ng/well of recombinant purified human MBL are bound to mannan coated microtiter wells by incubation over night at 4° C. in the above washing buffer except that 1 mg/mL of human albumin is added (State Serum Institute, Copenhagen Denmark). Wells are then washed 3 timers in washing buffer and are ready for use.

3) Screening for Inhibition of MASP-2 Catalysed C4 Deposition:

The substance to be screened for inhibition activity (e.g. hybridoma cell culture supernatant, purified antibody) is added to rMBL/rMASP-2 bound to mannan coated microtiter wells in the above washing buffer except that 1 mg/mL of human albumin is added (State Serum Institute, Copenhagen Denmark) and incubated for 1 hr at room temperature. Wells are washed 3 times in washing buffer and incubated 1.5 hr at 37° C. with purified human complement component C4 (approx. 1.5-2 ng/mL) in a buffer of barbital sodium (5 mM), NaCl (181 mM), CaCl2 (2.5 mM), MgCl2 (1.25 mM), pH 7.4, 1 mg/mL of human albumin (State Serum Institute, Copenhagen Denmark) is added before use. Wells are washed 3 times in washing buffer and 0.89 mg/L biotinylated rabbit anti-human complement component C4c is added (Dako, Denmark, biotinylated according to standard procedures). Wells are incubated for 1 hr at room temperature and washed 3 times in washing buffer. Europium labelled streptavidin (Wallac, Turku, Finland) is added at a concentration of 0.1 mg/L in the above washing buffer except that calcium is omitted and 50 µM EDTA is included. Wells are incubated 1 hr at room temperature and washed 3 times in washing buffer. Wells are developed by adding 100 µL of Delfia Enhancement Solution (Perkin Elmer Wallac, Norton, USA) and incubated on an orbital shaker for 5 min. at room temperature. Wells are counted in a Wallac Victor $2^d$ Multi counter 1420 (Wallac, Turku, Finland).

Inhibition is seen as decreased counts compared to wells where no inhibiting substance has been added.

Example 3

Assay for Inhibition of MASP-2 Catalysed C4 Deposition in Full Serum:

The serum sample to be analysed is diluted 250 times (final concentration) in the above barbital buffer and C4 is added (1.5-2 ng/mL, final concentration). The substance to be screened for inhibition activity (e.g. purified antibody) is added and samples are incubated between 5 min and 2 hours at 37° C. Normally incubation is 15 min. 100 µl is added to mannan coated microtiter wells prepared as described above and incubated 1½ hr at 37° C. Wells are washed 3 times in the above washing buffer and 0.89 mg/L biotinylated rabbit anti-human complement component C4c is added (Dako, Denmark, biotinylated according to standard procedures). Wells are incubated for 1 hr at room temperature and washed 3 times in washing buffer. Europium labelled streptavidin (Wallac, Turku, Finland) is added at a concentration of 0.1 mg/L in the above washing buffer except that calcium is omitted and 50 µM EDTA is included. Wells are incubated 1 hr at room temperature and washed 3 times in washing buffer. Wells are developed by adding 100 µL of Delfia Enhancement Solution (Perkin Elmer Wallac, Norton, USA) and incubated on an orbital shaker for 5 min. at room temperature. Wells are counted in a Wallac Victor $2^d$ Multi counter 1420 (Wallac, Turku, Finland).

Figure 3:
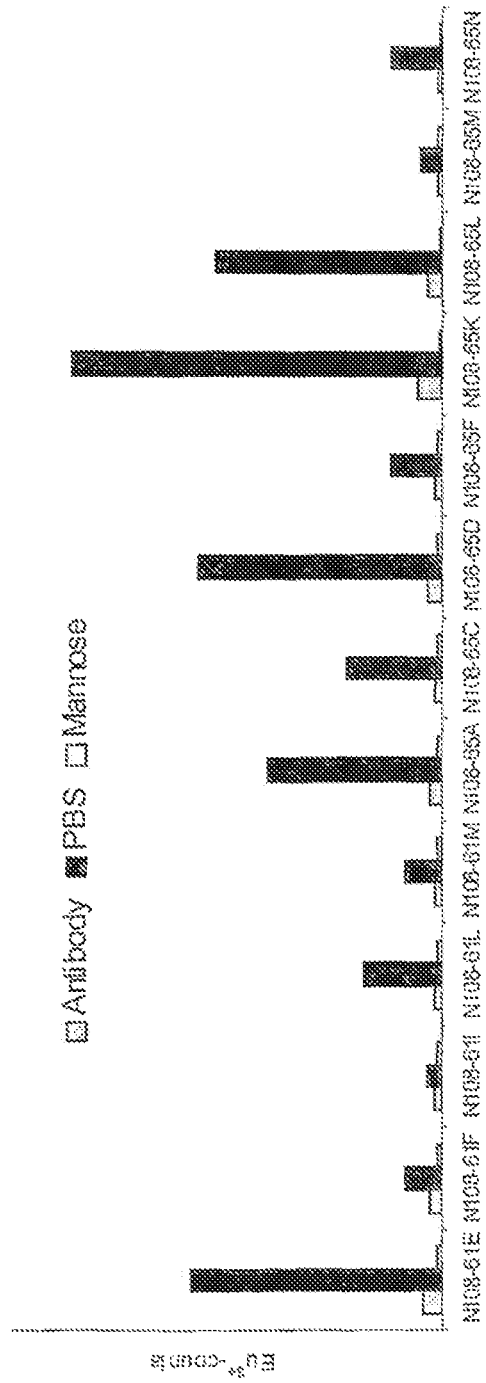
FIG. 3 depicts inhibition of C4 deposition in full serum by a MASP-2 antibody.

FIG. 3 illustrates the Eu3 counts obtained after performing the inhibition assay using either the monoclonal antibody produced by the hybridoma cell line deposited under 03050904, PBS or mannose. The antibody is capable of largely inhibiting C4 deposition in all the serums teste.

Figure 4:
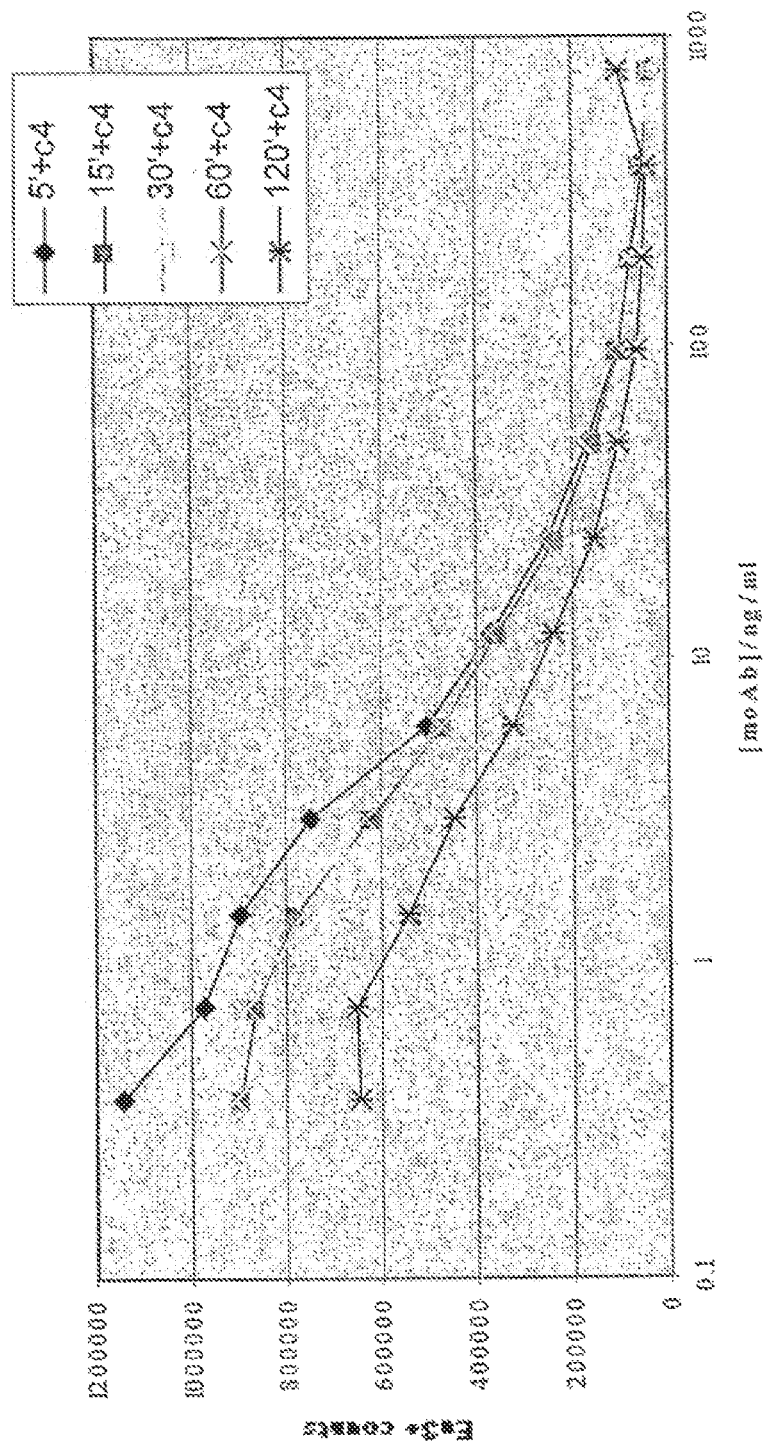
FIG. 4 depicts inhibition of C4 deposition by different concentrations of a MASP-2 antibody.

FIG. 4 illustrates inhibition of C4 deposition in full serum by the monoclonal antibody produced by the hybridoma cell line deposited under 03050904 as a function of concentration of the antibody.

Example 4

Pharmaceutical Composition

One dosis unit of a pharmaceutical composition according to the invention may comprise 300 mg MASP-2 antibody produced by the hybridoma cell line deposited under deposition number 03050904, purified as described in example 1, and formulated in 10 mM Tris-buffer, pH 7.4 and 140 mM NaCl.

The pharmaceutical composition is filtered through a Planova 75N and a Planova 35N filter to remove any vira, and sterile filtered over a 0.22 µm filter.

This formulation is suitable for parenteral administration to a human adult.

Example 5

Production and Characterisation of Inhibitory Anti-hu-MASP-2 Murine Monoclonal Antibodies Immunization Four mice (6-8 weeks old) were immunized. A total of four injections was administered (50 µg antigen per animal per injection). Mice were injected on day 0 with equal parts (v/v) of complete Freund's adjuvant and 10 µg of His-tagged human MASP2 (N039-76C). Three following boosts were carried out with equal parts (v/v) incomplete Freund's adjuvant and antigen, with three weeks between boosts. The best responding mouse 10 days after the last injection was selected using an ELISA test against MASP-2.

Hybridization, Fusion

Fusions were performed using conventional methodology. The splenic lymphocytes of the best responding animal were fused with the cell line Sp2/O—Ag-14 using PEG (polyethylene glycol), and the resulting hybridomas were seeded in 96-well plates in HAT medium.

Medium was changed 2-3 times before screening. Usually, hybridoma colonies were ready for screening in 3-5 weeks. Supernatants were tested for the presence of inhibitory antibody by C4 deposition assay. The hybridomas were sub-cloned by limiting dilution.

785 primary clones were screened for inhibition activity and 50 inhibiting clones were selected for subcloning. Subclones were screened for inhibition and clones showing the most inhibitory activity were subcloned again. After 2 to 3 subclonings, 4 inhibitory clones of interest remained (see table 1 herein below).

Inhibition of C-4 Deposition Assay

Buffer B1/HSA: a buffer of barbital sodium (5 mM), NaCl (181 mM), CaCl2 (2.5 mM), MgCl2 (1.25 mM), pH 7.4. 1 mg/mL of human albumin (State Serum Institute, Copenhagen Denmark) is added before use.

The assay is composed of three steps 1) preparation of mannan coated microtiter wells 2) Preincubation of antibodies with human serum 3) measurement of MASP-2 catalysed C4 deposition.

Preparation of Mannan Coated Microtiter Wells:

96 wells microtiter plates (FluroNunc, Nalgene Nunc Int., Denmark) are coated with mannan (10 mg/L, Sigma Chemical Co., St. Louis, USA) in a coating buffer (Na2CO3: 3.18 g/L; NaHCO$_3$: 5.86 g/L; pH adjusted to 9.6 using HCl) over night at room temperature. Wells are washed 2 times in TBS (10 mM Tris, 150 mM NaCl, pH=7.4 using HCl). Wells are then blocked by incubation for 1 hr at room temperature in a buffer as above except that 1 mg/mL of human albumin is added (State Serum Institute, Copenhagen Denmark). Wells are then washed 3 times in TBST (10 mM Tris, 150 mM NaCl, 0.05% Tween 20, pH=7.4 using HCl, from) and are ready for use.

Preincubation of Antibodies with Human Serum:

The antibodies to be tested are serial diluted in B1/HSA. 100 µL from each dilution is transferred to a well of a 96-well Nucleon surface plate. 100 µL full human serum diluted ×125 (final 250×) is added to each well together with purified human complement component C4 (approx. 3-4 mg/L). Incubate at 37C 15 min. 100 µL of the antibody-human serum mix is then transferred to the previous made mannan coated plates.

Measurement of MASP-2 Catalysed C4 Deposition:

The mannan coated plates are then incubated 1.5 hr at 37° C. Wells are washed 3 times in washing buffer TBST+Ca(10 mM Tris, 150 mM NaCl, 10 mM CaCl2), 0.05% Tween 20, pH=7.4 using HCl) and 0.89 mg/L biotinylated rabbit anti-human complement component C4c diluted in TBST+Ca is added (Dako, Denmark, biotinylated according to standard procedures). Wells are incubated for 1 hr at room temperature and washed 3 times in washing buffer. Europium labelled streptavidin (Wallac, Turku, Finland) is added at a concentration of 0.1 mg/L in the above washing buffer except that calcium is omitted and 50 µM EDTA is included. Wells are incubated 1 hr at room temperature and washed 3 times in washing buffer. Wells are developed by adding 100 µL of Delfia Enhancement Solution (Perkin Elmer Wallac, Norton, USA) and incubated on an orbital shaker for 5 min. at room temperature. Wells are counted in a Wallac Victor 2d Multi counter 1420 (Wallac, Turku, Finland).

Western Blot

Human serum (0.15 µl/lane) was run on NuPage 4-12% Bis-Tris polyacrylamide gels and transferred to PVDF membrane. The blots were blocked with 0.5% gelatine in incubation buffer (5×: 250 mM Tris; 750 mM NaCl; 25 mM EDTA; 0.5% IGEPAL CA-630. pH 7.4) and incubated with the monoclonal antibodies, followed by HRP-conjugated rabbit anti-mouse IgG (DAKO Po260). The blots were detected with SuperSignal West Pico Chemiluminescent kit (Pierce Inc.)

MASP-2 Competitive ELISA

Coating buffer: PBS (137 mM NaCl, 2.7 mM KCl, 1.5 mM KH2PO4, 8.1 mM Na2HPO4 pH=7.2 using NaOH)

Blocking Buffer: TBS (10 mM Tris, 150 mM NaCl, pH=7.4 using HCl) containing 1 mg/ml HSA Wash Buffer: TBST+Ca (10 mM Tris, 150 mM NaCl, 10 mM CaCl2), 0.05% Tween 20, pH=7.4 using HCl)

Coating of ELISA Plate:

MASP-2 antigen is diluted to 1 µg/ml in coating buffer [PBS pH 7.2]. 100 µl of MASP-2 coating solution is added to each well of the microtiter plate. The plate is incubated at room temperature 1 hour. The microtiter plate is emptied and each well of the plate is filled with Blocking Buffer and incubated for 1 hour at room temperature. The microtiter plate is emptied and each well is filled with Wash Buffer. The microtiter plate is emptied. This is repeated three times. The wells are filled with wash buffer and stored at 4° C.

The murine antibodies are appropriately diluted (0.2 and 1.0 ug/ml final) with Wash Buffer Biotinylated NimoAb101 is diluted (0.2 ug/ml final) in wash Buffer. The diluted murine Antibodies are added (100 ul/well) to the MASP-2 coated plate. The plate is incubated for 1 hour at room temperature. The microtiter plate is emptied.

The microtiter plate is washed by completely filling the wells with Wash Buffer and emptying. This step is repeated twice for a total of three washes.

Europium labelled streptavidin (Wallac, Turku, Finland) is added at a concentration of 0.1 mg/L in the above washing buffer except that calcium is omitted and 50 µM EDTA is included. Wells are incubated 1 hr at room temperature. The microtiter plate is emptied and the wells are washed three times with Wash Buffer. Wells are developed by adding 100 µL of Delfia Enhancement Solution (Perkin Elmer Wallac, Norton, USA) and incubated on an orbital shaker for 5 min. at room temperature. Wells are counted in a Wallac Victor 2d Multi counter 1420 (Wallac, Turku, Finland).

Results

Table 1 indicates four hybridomas producing inhibitory antibodies identified as outlined above.

TABLE 1

| NimoAb-Name | hybridoma-ID | trival name |
| --- | --- | --- |
| NimoAb104 | M0545YM035 | 035 |
| NimoAb108 | M0545YM029 | 029 |
| NimoAb109 | M0545YM046 | 046 |
| NimoAb110 | M0545YM048 | 048 |

Potency of the New Antibodies

Figure 5:
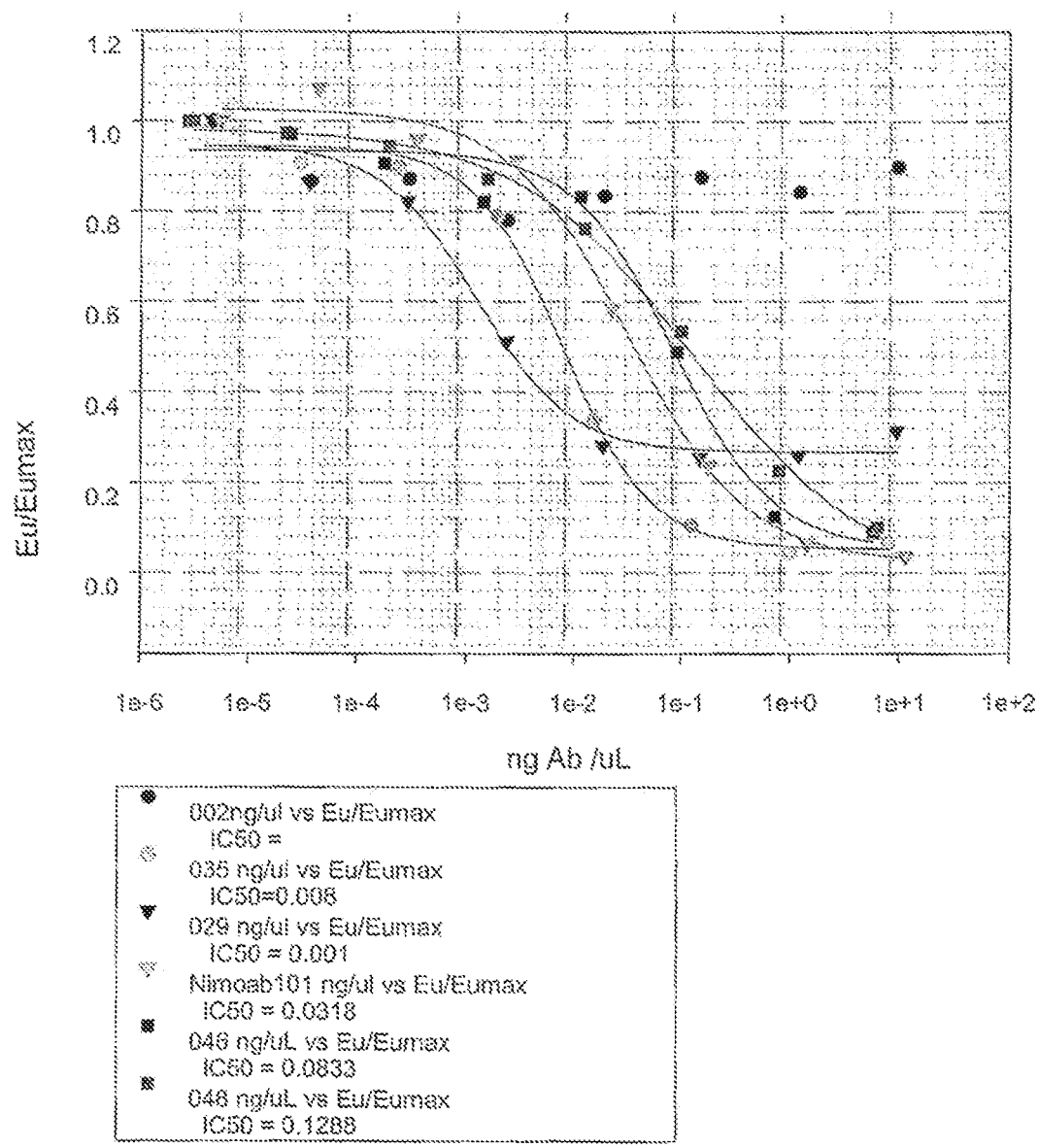
FIG. 5 shows a C4 deposition assay. The figure illustrates inhibition of C4 deposition in human serum using different purified anti-MASP-2 antibodies.

The four described hybridoma clones were transformed to serum free growth and antibodies were purified from culture supernatant by MEP HyperCel purification. The ability to inhibit lectin pathway in a full human serum was determined by the C4-deposition assay as described above. The results are shown in FIG. 5.

From the data it can be concluded that the antibody (035) is at least 3.9 times more potent than NimoAb101 in inhibition of MASP-2 activity, whereas the antibody (029) is at least 30 times more potent. The control antibody (002) is a non-inhibitory antibody obtained during the screening that most probably binds to the N-terminus of MASP-2. The antibodies (046) and (048) also inhibit, but they are less potent than NimoAb101.

Epitope Mapping

Figure 6:
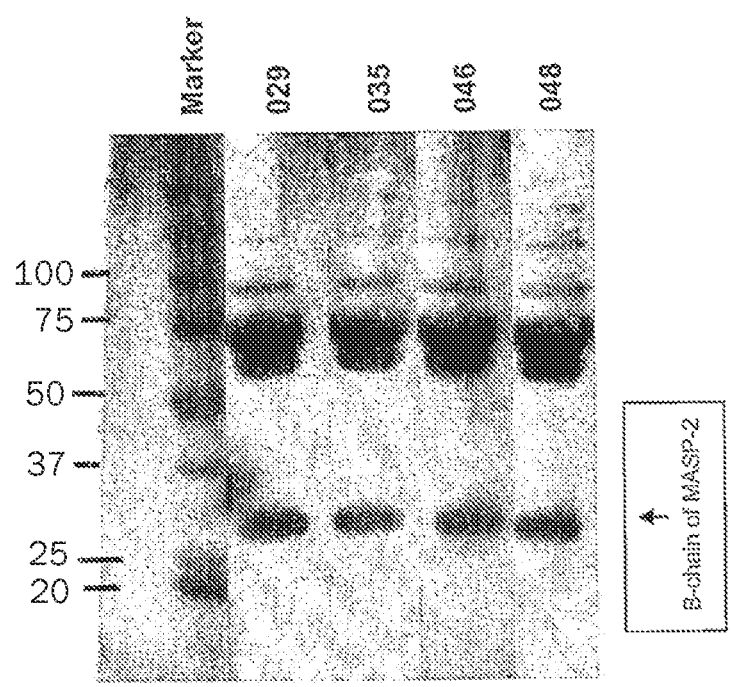
FIG. 6 shows an assembly of Western blots against MASP-2 in human serum using 4 different antibodies. Human serum was loaded on each lane. The figure is assembled from four separate Western blots using the antibodies shown in the lanes above for detection.

Western Blot:

Westerns were made in order to distinguish between binding of the antibodies to the N terminal A-chain (dimerization and MBL-binding part) or to the C-terminal B-chain (serine protease part of MASP-2). Human serum was run on a reduced SDS-PAGE and immunodetection was done with the four antibodies separate. Full length nonactivated MASP-2 will exhibit a band of 74 kDa, the A-chain and the B-chain exhibit bands of 47 kDa and 27 kDa respectively. FIG. 6 shows the results of the Western blots against MASP-2 in human serum using the different murine antibodies.

It can be concluded from the blot that all four antibodies recognize a 27 kDa band (B-chain), whereas the A-chain (47 kDa) not could be detected. Thus all four antibodies recognize a linear epitope on the B-chain.

Competitive ELISA

With the aim of elucidating whether the antibodies share the same epitope as the rat antibody NimoAb101 we have conducted competitive ELISA. The ELISA was directed toward recombinant His-tagged MASP-2 using a biotinylated NimoAb101 competing against two different concentrations (0.2 and 1.0 µg/ml) of the mouse antibodies.

Figure 7:
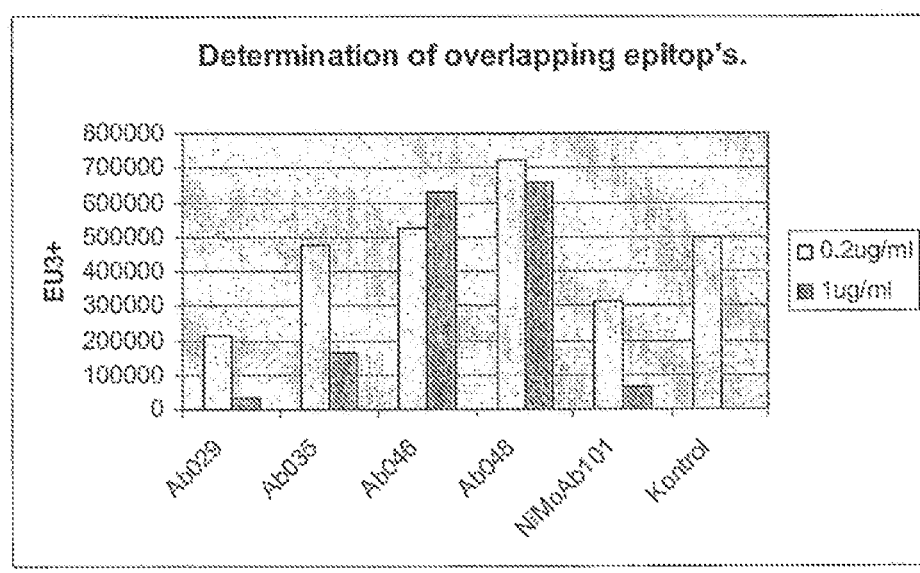
FIG. 7 shows the results of a competive ELISA for determination of overlapping epitopes.

The results are displayed in FIG. 7. The better an antibody competes with NimoAb101, the lower the EU3+ signal will be. It can thus be concluded that the antibodies 029(NimoAb108) and 035(NimoAb104) compete very well with the NimoAb101 antibody, thus they must share at least part of the epitope.

Example 6

Identification and Cloning of the VH and the VL Region of the Antibody NimoAb101 Expressed in Hybridoma Cells Deposited Under ECACC Accession No. 03050904.

The specificity of antibodies resides in the complementarity determining regions (CDRs) within the variable domains of the heavy- and light chains. In order to characterize the monoclonal antibody Nimoab101 the VH and VL domains variable region were cloned.

Abbreviations Used $V_H$=the variable region of the heavy chain of Ig; $V_L$=the variable region of the light chain of Ig CDR=complementarity-determining region; CDR1, CDR2 and CDR3=three regions on either $V_H$ or $V_L$, which are numbered from the amino terminus;

FR=framework region; FR3=the third framework region on either $V_H$ or $V_L$, numbered from the amino terminus scFv=single-chain Fv fragment;

cDNA (complementary DNA)=A single-stranded DNA molecule that is complementary in base sequence to an RNA strand.

5'RACE=rapid amplification of cDNA 5'end

Materials and Methods

Isolation of Total RNA and mRNA

Hybridoma cells of the cell line deposited under the ECAAC number 03050904 were dispensed into 4 tubes. Cells were pelleted and the supernatant was removed. Two of the tubes were frozen at −80C Two of the tubes were used for purification of RNA using GenElute™ Mammalian Total RNA Kit RTN70. RNA concentration was determined spectrophotometrically.

Total RNA was also purified using Total RNA purification with NucleoSpin® RNA II Kit: Cat. No. 740955.20 Macherey-Nagel. The yield was determined spectrophotometrically.

Poly(A) RNA was isolated from total RNA with Nucleo-Trap® mRNA Kit: Cat. No. 740655 Macherey-Nagel Purified mRNA was eluted in H2O (RNase-free) and was immediately stored at −80° C.

Construction of cDNA

5'RACE

5' rapid amplification of cDNA ends (RACE) was carried out using the SMART RACE cDNA amplification kit (Clontech) according to the manufacturer's instructions. $G_{RT}$ was used for reverse transcription (RT), and amplification was performed with $G_{3'}$.

The gene specific primers used in this approach were:

| Oligo name | Oligo sequence |
|---|---|
| RACKFOR | CTCATTCCTGTTGAAGCTCTTGACGA (SEQ ID 12) |
| RACERAG1 | AGGCTTGCAATCACCTCCACA (SEQ ID 13) |

Plasmid Construction: Cloning of PCR Fragments

Parental Plasmid:

pCR2.1-TOPO (InVitrogen TOPO TA clonings kit)

The purified PCR fragment were cloned into the vector using the Topo reaction.

Sequence Analysis

DNA from plasmid mini-preparation of four recombinant clones of VL and plasmid mini-preparation of six recombinant clones of VH were sequenced of the insert in both directions using standard sequencing primers M13F and M13R. The two respective sequences from each plasmid were assembled to a contig using VNTI contig express. The reliable part of the contig consensus sequences were imported to NTI DNA database files.

The relevant IgG orfs were identified and translated.

Sequence Alignment and Blast Search

Computer Analysis

Sequence analysis was done with VectorNTI from Informax Inc. using the Contig module.

BLAST searches were performed using NCBI home page (http://www.ncbi.nlm.nih.gov) and The European Bioinformatics Institute (EBI) (http://www.ebi.ac.uk/Tools/homology.html).

Protein alignments: All alignments were done with the VectorNTI package from Informax Inc. using the ALIGN module. Multiple alignments for the IgG VL and VH proteins were done and edited with CLUSTALW and GeneDoc.

Results and Discussion

Figure 8:
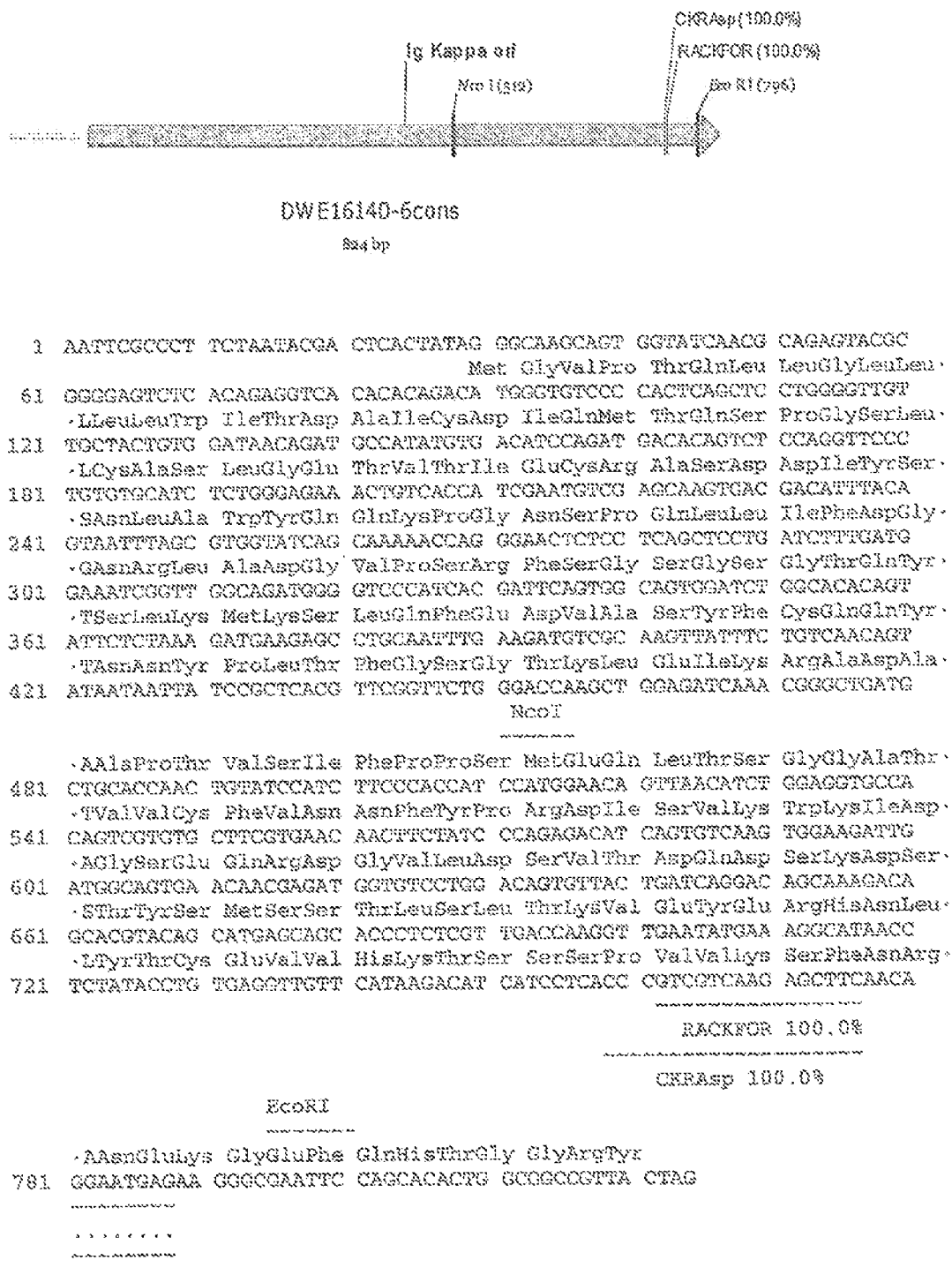
FIG. 8 illustrates the nucleotide sequence (SEQ ID NO:18) encoding the variable region of the light chain of the NimoAb101 antibody (DWE16140-6cons) (SEQ ID NO:19).
Figure 9:
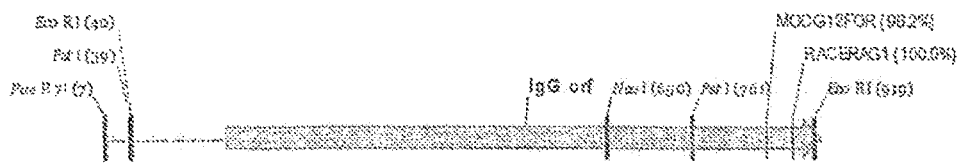
FIG. 9 illustrates the nucleotide sequence (SEQ ID NO:20) encoding the variable region of the heavy chain of NimoAb101 antibody (DWE16140-3consRev) (SEQ ID NO:21).

The antibody Nimoab101 was raised against the CCP1-CCP2-SP-subunit of human MASP-2. We amplified the genes of the Fab fragment by PCR of hybridoma mRNA, using primers hybridizing in the constant domains $C_H1$ and $C_L$ adapted from the literature (1) and primers hybridizing to an adapter that was incorporated into the the 5' end of the cDNA genes. The purified VL and VH PCR products were cloned into pCR2.1-TOPO vector and sequenced with M13F and M13R primers. All of the VH sequences and all of the VL sequences were identical. The sequences are shown in FIGS. 8 to 10.

| Kabat CRD definition | |
|---|---|
| Light Chain | CDR1: residues 24-34 |
| | CDR2: residues 50-56 |
| | CDR3: residues 89-97 |
| Heavy Chain | CDR1: residues 31-35 |
| | CDR2: residues 50-65 |
| | CDR3: residues 95-102 |

Comparison of the sequences with published antibody variable region data indicated that the NimoAb101 VL gene contained a leader sequence of 57 nucleotides encoding leader peptide of 19 amino acid residues, while the NimoAb101 VH gene had a 60 bases long leader sequences that encoded a 20 residues leader peptide.

While the light chain is a typical member of (rat-mouse-human) kappa chain subgroup, the heavy chain differs from heavy chain other in the data base. It has an insertion of 6 amino acids in CDR H3 (after residue 100, Kabat numbering).

REFERENCES

1) *Protein Sequence and Structure Analysis of Antibody Domains* published in the Springer Verlag Laboratory Manual on Antibody Engineering edited by Stefan Duebel and Roland Kontermann Biological Deposition The following biological material has been deposited at a depositary institution recognised under the Budapest Treaty.

A hybridoma cell line capable of producing antibodies to MASP-2, capable of inhibiting MASP-2 activity has been deposited under the deposit accession number 03050904 with the EUROPEAN COLLECTION OF CELL CULTURES (ECACC), Salisbury, Wiltshire SP4 0JG, United Kingdom. The cell line is a hybridoma cell line derived from a fusion of rat spleen cells and mouse myeloma cells. This hybridoma cell line is producing a monoclonal antibody, which is herein referred to as NimoAb101 or NimoAb101 N128-71B. The cells were deposited 9 May 2003.

A hybridoma cell line designated M0545YM035S2 (herein also designated M0545YM035) has been deposited with Deutsche Sammlung von Mikroorganismen und Zellkulturen (DSMZ), Mascheroder Weg 1b, D-38124 Braunschweig, Germany under deposit accession number DSMACC2660. The cell line is a hybridoma cell line derived from a fusion of murine spleen cells and mouse myeloma cells. The identification reference is N162-91A-01 to 12. This hybridoma cell line is producing a monoclonal antibody, which is herein referred to as NimoAb104 or "035" or Ab035. The cells were deposited 6 May 2004.

A hybridoma cell line designated M0545YM029S2 (herein also designated M0545YM029) has been deposited with Deutsche Sammlung von Mikroorganismen und Zellkulturen (DSMZ), Mascheroder Weg 1b, D-38124 Braunschweig, Germany_under deposit accession number DSMACC2657. The cell line is a hybridoma cell line derived from a fusion of murine spleen cells and mouse myeloma cells. The identification reference is N162-90C-01 to 12. This hybridoma cell line is producing a monoclonal antibody, which is herein referred to as NimoAb108 or "029" or Ab029. The cells were deposited 6 May 2004.

A hybridoma cell line designated M0545YM046S2 (herein also designated M0545YM046) has been deposited with Deutsche Sammlung von Mikroorganismen und Zellkulturen (DSMZ), Mascheroder Weg 1b, D-38124 Braunschweig, Germany under deposit accession number DSMACC2658. The cell line is a hybridoma cell line derived from a fusion of murine spleen cells and mouse myeloma cells. The identification reference is N162-90D-01 to 12. This hybridoma cell line is producing a monoclonal antibody, which is herein referred to as NimoAb109 or "046" or Ab046. The cells were deposited 6 May 2004.

A hybridoma cell line designated M0545YM048S2 (herein also designated M0545YM048) has been deposited with Deutsche Sammlung von Mikroorganismen und Zellkulturen (DSMZ), Mascheroder Weg 1b, D-38124 Braunschweig, Germany under deposit accession number DSMACC2659. The cell line is a hybridoma cell line derived from a fusion of murine spleen cells and mouse myeloma cells. The identification reference is N162-90E-01 to 12. This hybridoma cell line is producing a monoclonal antibody, which is herein referred to as NimoAb110 or "048" or Ab048. The cells were deposited 6 May 2004.

REFERENCES

Hemmila, I., Dakubu, S., Mukkala, V. M., Siitari, H. and Lovgren, T. (1984) Europium as a label in time-resolved immunofluorometric assays. Anal Biochem 137, 335-43.

Jones, P. T., Dear, P. H., Foote, J., Neuberger, M. S., Winter, G., 1986. Replacing the complementarity-determining regions in a human antibody with those from a mouse. Nature, 321, 522-525

Liu, H., Jensen, L., Hansen, S., Petersen, S. V., Takahashi, K., Ezekowitz, A. B., Hansen, F. D., Jensenius, J. C. and Thiel, S. (2001) Characterization and quantification of mouse mannan-binding lectins (MBL-A and MBL-C) and study of acute phase responses. Scand J Immunol 53, 489-97.

Nakajima, T. and Ballou, C. E. (1974) Characterization of the carbohydrate fragments obtained from *Saccharomyces cerevisiae* mannan by alkaline degradation. J Biol Chem 249, 7679-84.

Rossi, V., Cseh, S., Bally, I., Thielens, N. M., Jensenius, J. C. and Arlaud, G. J. (2001) Substrate specificities of recombinant mannan-binding lectin-associated serine proteases-1 and -2. J Biol Chem 276, 40880-7.

For all deposited microbial organisms mentioned in the present patent application the following applies.

Europe

In respect to those designations in which a European Patent is sought a sample of the deposited microorganism will be made available until the publication of the mention of the grant of the European patent or until the date on which application has been refused or withdrawn or is deemed to be withdrawn, only by the issue of such a sample to an expert nominated by the person requesting the sample, and approved either i) by the Applicant and/or ii) by the European Patent Office, whichever applies. (Rule 28 (4) EPC).

Canada

The applicant requests that, until either a Canadian patent has been issued on the basis of an application or the application has been refused, or is abandoned and no longer subject to reinstatement, or is withdrawn, the Commissioner of Patents only authorizes the furnishing of a sample of the deposited biological material referred to in the application to an independent expert nominated by the Commissioner, the applicant must, by a written statement, inform the International Bureau accordingly before completion of technical preparations for publication of the international application.

Norway

The applicant hereby requests that, until the application has been laid open to public inspection (by the Norwegian Patent Office), or has been finally decided upon by the Norwegian Patent Office without having been laid open inspection, the furnishing of a sample shall only be effected to an expert in the art. The request to this effect shall be filed by the applicant with the Norwegian Patent Office not later than at the time when the application is made available to the public under Sections 22 and 33(3) of the Norwegian Patents Act. If such a request has been filed by the applicant, any request made by a third party for the furnishing of a sample shall indicate the 'expert to be used. That expert may be any person entered on the list of recognized experts drawn up by the Norwegian Patent Office or any person approved by the applicant in the individual case.

Australia

The applicant hereby gives notice that the furnishing of a sample of a microorganism shall only be effected prior to the grant of a patent, or prior to the lapsing, refusal or withdrawal of the application, to a person who is a skilled addressee without an interest in the invention (Regulation 3.25(3) of the Australian Patents Regulations).

Finland

The applicant hereby requests that, until the application has been laid open to public inspection (by the National Board of Patents and Regulations), or has been finally decided upon by the National Board of Patents and Registration without having been laid open to public inspection, the furnishing of a sample shall only be effected to an expert in the art.

United Kingdom

The applicant hereby requests that the furnishing of a sample of a microorganism shall only be made available to an expert. The request to this effect must be filed by the applicant with the International Bureau before the completion of the technical preparations for the international publication of the application.

Denmark

The applicant hereby requests that, until the application has been laid open to public inspection (by the Danish Patent Office), or has been finally decided upon by the Danish Patent office without having been laid open to public inspection, the furnishing of a sample shall only be effected to an expert in the art. The request to this effect shall be filed by the applicant with the Danish Patent Office not later that at the time when the application is made available to the public under Sections 22 and 33(3) of the Danish Patents Act. If such a request has been filed by the applicant, any request made by a third party for the furnishing of a sample shall indicate the expert to be used. That expert may be any person entered on a list of recognized experts drawn up by the Danish Patent Office or any person by the applicant in the individual case.

Sweden

The applicant hereby requests that, until the application has been laid open to public inspection (by the Swedish Patent Office), or has been finally decided upon by the Swedish Patent Office without having been laid open to public inspection, the furnishing of a sample shall only be effected to an expert in the art. The request to this effect shall be filed by the applicant with the International Bureau before the expiration of 16 months from the priority date (preferably on the Form PCT/RO/134 reproduced in annex Z of Volume I of the PCT Applicant's Guide). If such a request has been filed by the applicant any request made by a third party for the furnishing of a sample shall indicate the expert to be used. That expert may be any person entered on a list of recognized experts drawn up by the Swedish Patent Office or any person approved by a applicant in the individual case.

Netherlands

The applicant hereby requests that until the date of a grant of a Netherlands patent or until the date on which the application is refused or withdrawn or lapsed, the microorganism shall be made available as provided in the 3 IF(1) of the Patent Rules only by the issue of a sample to an expert. The request to this effect must be furnished by the applicant with the Netherlands Industrial Property Office before the date on which the application is made available to the public under Section 22C or Section 25 of the Patents Act of the Kingdom of the Netherlands, whichever of the two dates occurs earlier.

The invention claimed is:

1. A method of treating a subject suffering from, or at risk for developing, an ischemia/reperfusion injury resulting from a percutaneous transluminal coronary angioplasty or resulting from coronary artery bypass grafting or resulting from brain ischemia comprising administering to said subject a therapeutically effective dosage of a monoclonal antibody or antigen-binding fragment thereof specifically recognizing and binding an epitope within the C-terminal part of MASP-2 consisting of the CCP1, CCP2 and serine protease domains (amino acid residues 293 to 686 of SEQ ID NO:1), wherein the monoclonal antibody, or antigen-binding fragment thereof, is capable of inhibiting MASP-2 catalyzed C4 deposition.

2. The method of claim 1, wherein said antibody is a human antibody.

3. The method of claim 1, wherein said antibody has been humanized.

4. The method of claim 1, wherein said antigen-binding fragment is selected from the group consisting of Fab, Fab', F(ab')2 and Fv fragments.

5. The method of claim 1, wherein said antibody is a single chain antibody.

* * * * *

SEQUENCE LISTING

```
<160> NUMBER OF SEQ ID NOS: 48

<210> SEQ ID NO 1
<211> LENGTH: 686
<212> TYPE: PRT
<213> ORGANISM: Homo sapiens

<400> SEQUENCE: 1

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80
```

-continued

```
Ser Gly Ala Lys Val Leu Ala Thr Leu Cys Gly Gln Glu Ser Thr Asp
             85                  90                  95
Thr Glu Arg Ala Pro Gly Lys Asp Thr Phe Tyr Ser Leu Gly Ser Ser
            100                 105                 110
Leu Asp Ile Thr Phe Arg Ser Asp Tyr Ser Asn Glu Lys Pro Phe Thr
            115                 120                 125
Gly Phe Glu Ala Phe Tyr Ala Ala Glu Asp Ile Asp Glu Cys Gln Val
130                 135                 140
Ala Pro Gly Glu Ala Pro Thr Cys Asp His His Cys His Asn His Leu
145                 150                 155                 160
Gly Gly Phe Tyr Cys Ser Cys Arg Ala Gly Tyr Val Leu His Arg Asn
            165                 170                 175
Lys Arg Thr Cys Ser Ala Leu Cys Ser Gly Gln Val Phe Thr Gln Arg
            180                 185                 190
Ser Gly Glu Leu Ser Ser Pro Glu Tyr Pro Arg Pro Tyr Pro Lys Leu
            195                 200                 205
Ser Ser Cys Thr Tyr Ser Ile Ser Leu Glu Glu Gly Phe Ser Val Ile
210                 215                 220
Leu Asp Phe Val Glu Ser Phe Asp Val Glu Thr His Pro Glu Thr Leu
225                 230                 235                 240
Cys Pro Tyr Asp Phe Leu Lys Ile Gln Thr Asp Arg Glu Glu His Gly
            245                 250                 255
Pro Phe Cys Gly Lys Thr Leu Pro His Arg Ile Glu Thr Lys Ser Asn
            260                 265                 270
Thr Val Thr Ile Thr Phe Val Thr Asp Glu Ser Gly Asp His Thr Gly
            275                 280                 285
Trp Lys Ile His Tyr Thr Ser Thr Ala His Ala Cys Pro Tyr Pro Met
            290                 295                 300
Ala Pro Pro Asn Gly His Val Ser Pro Val Gln Ala Lys Tyr Ile Leu
305                 310                 315                 320
Lys Asp Ser Phe Ser Ile Phe Cys Glu Thr Gly Tyr Glu Leu Leu Gln
            325                 330                 335
Gly His Leu Pro Leu Lys Ser Phe Thr Ala Val Cys Gln Lys Asp Gly
            340                 345                 350
Ser Trp Asp Arg Pro Met Pro Ala Cys Ser Ile Val Asp Cys Gly Pro
            355                 360                 365
Pro Asp Asp Leu Pro Ser Gly Arg Val Glu Tyr Ile Thr Gly Pro Gly
            370                 375                 380
Val Thr Thr Tyr Lys Ala Val Ile Gln Tyr Ser Cys Glu Glu Thr Phe
385                 390                 395                 400
Tyr Thr Met Lys Val Asn Asp Gly Lys Tyr Val Cys Glu Ala Asp Gly
            405                 410                 415
Phe Trp Thr Ser Ser Lys Gly Glu Lys Ser Leu Pro Val Cys Glu Pro
            420                 425                 430
Val Cys Gly Leu Ser Ala Arg Thr Gly Gly Arg Ile Tyr Gly Gly Gly
            435                 440                 445
Gln Lys Ala Lys Pro Gly Asp Phe Pro Trp Gln Val Leu Ile Leu Gly
            450                 455                 460
Gly Thr Thr Ala Ala Gly Ala Leu Leu Tyr Asp Asn Trp Val Leu Thr
465                 470                 475                 480
Ala Ala His Ala Val Tyr Glu Gln Lys His Asp Ala Ser Ala Leu Asp
            485                 490                 495
```

Ile Arg Met Gly Thr Leu Lys Arg Leu Ser Pro His Tyr Thr Gln Ala
                500                 505                 510

Trp Ser Glu Ala Val Phe Ile His Gly Tyr Thr His Asp Ala Gly
        515                 520                 525

Phe Asp Asn Asp Ile Ala Leu Ile Lys Leu Asn Asn Lys Val Val Ile
        530                 535                 540

Asn Ser Asn Ile Thr Pro Ile Cys Leu Pro Arg Lys Glu Ala Glu Ser
545                 550                 555                 560

Phe Met Arg Thr Asp Asp Ile Gly Thr Ala Ser Gly Trp Gly Leu Thr
                565                 570                 575

Gln Arg Gly Phe Leu Ala Arg Asn Leu Met Tyr Val Asp Ile Pro Ile
        580                 585                 590

Val Asp His Gln Lys Cys Thr Ala Ala Tyr Glu Lys Pro Pro Tyr Pro
        595                 600                 605

Arg Gly Ser Val Thr Ala Asn Met Leu Cys Ala Gly Leu Glu Ser Gly
        610                 615                 620

Gly Lys Asp Ser Cys Arg Gly Asp Ser Gly Gly Ala Leu Val Phe Leu
625                 630                 635                 640

Asp Ser Glu Thr Glu Arg Trp Phe Val Gly Gly Ile Val Ser Trp Gly
                645                 650                 655

Ser Met Asn Cys Gly Glu Ala Gly Gln Tyr Gly Val Tyr Thr Lys Val
                660                 665                 670

Ile Asn Tyr Ile Pro Trp Ile Glu Asn Ile Ile Ser Asp Phe
            675                 680                 685

<210> SEQ ID NO 2
<211> LENGTH: 142
<212> TYPE: PRT
<213> ORGANISM: Rattus norvegicus

<400> SEQUENCE: 2

Met Ser Phe Ser Asn Thr Leu Val Phe Leu Leu Phe Leu Leu Lys Gly
1               5                   10                  15

Ile Leu Cys Glu Val Gln Leu Val Glu Ser Gly Gly Gly Leu Val Gln
                20                  25                  30

Pro Gly Arg Ser Leu Lys Leu Ser Cys Leu Val Ser Gly Phe Thr Phe
            35                  40                  45

Ser Asn Phe Gly Met Asn Trp Ile Arg Gln Ala Pro Gly Lys Gly Leu
        50                  55                  60

Glu Trp Val Ala Ser Ile Ser Ser Gly Gly Thr Tyr Ile Tyr His Ala
65                  70                  75                  80

Asp Thr Leu Lys Gly Arg Phe Thr Ile Ser Arg Glu Asn Ala Lys Asn
                85                  90                  95

Thr Leu Tyr Leu Gln Met Thr Ser Leu Arg Ser Glu Asp Thr Ala Leu
            100                 105                 110

Tyr Tyr Cys Ala Arg Gly Pro Tyr His Ser Arg Tyr Ile Pro Tyr Leu
        115                 120                 125

Met Asp Ala Trp Gly Gln Gly Ala Ser Val Thr Val Ser Ser
        130                 135                 140

<210> SEQ ID NO 3
<211> LENGTH: 132
<212> TYPE: PRT
<213> ORGANISM: Rattus norvegicus

<400> SEQUENCE: 3

-continued

Met Gly Val Pro Thr Gln Leu Leu Gly Leu Leu Leu Trp Ile Thr
1               5                   10                  15

Asp Ala Ile Cys Asp Ile Gln Met Thr Gln Ser Pro Gly Ser Leu Cys
            20                  25                  30

Ala Ser Leu Gly Glu Thr Val Thr Ile Glu Cys Arg Ala Ser Asp Asp
        35                  40                  45

Ile Tyr Ser Asn Leu Ala Trp Tyr Gln Gln Lys Pro Gly Asn Ser Pro
    50                  55                  60

Gln Leu Leu Ile Phe Asp Gly Asn Arg Leu Ala Asp Gly Val Pro Ser
65              70                  75                  80

Arg Phe Ser Gly Ser Gly Ser Gly Thr Gln Tyr Ser Leu Lys Met Lys
                85                  90                  95

Ser Leu Gln Phe Glu Asp Val Ala Ser Tyr Phe Cys Gln Gln Tyr Asn
            100                 105                 110

Asn Tyr Pro Leu Thr Phe Gly Ser Gly Thr Lys Leu Glu Ile Lys Arg
        115                 120                 125

Ala Asp Ala Ala
    130

<210> SEQ ID NO 4
<211> LENGTH: 156
<212> TYPE: PRT
<213> ORGANISM: Rattus norvegicus

<400> SEQUENCE: 4

Glu Ser Gly Gly Gly Leu Val Gln Pro Gly Arg Ser Leu Lys Leu Ser
1               5                   10                  15

Cys Leu Val Ser Gly Phe Thr Phe Ser Asn Phe Gly Met Asn Trp Ile
            20                  25                  30

Arg Gln Ala Pro Gly Lys Gly Leu Glu Trp Val Ala Ser Ile Ser Ser
        35                  40                  45

Gly Gly Thr Tyr Ile Tyr His Ala Asp Thr Leu Lys Gly Arg Phe Thr
    50                  55                  60

Ile Ser Arg Glu Asn Ala Lys Asn Thr Leu Tyr Leu Gln Met Thr Ser
65              70                  75                  80

Leu Arg Ser Glu Asp Thr Ala Leu Tyr Tyr Cys Ala Arg Gly Pro Tyr
                85                  90                  95

His Ser Arg Tyr Ile Pro Tyr Leu Met Asp Ala Trp Gly Gln Gly Ala
            100                 105                 110

Ser Val Thr Val Ser Ser Ala Glu Thr Thr Ala Pro Ser Val Tyr Pro
        115                 120                 125

Leu Ala Pro Gly Thr Ala Leu Lys Ser Asn Ser Met Val Thr Leu Gly
    130                 135                 140

Cys Leu Val Lys Gly Tyr Phe Pro Glu Pro Val Thr
145                 150                 155

<210> SEQ ID NO 5
<211> LENGTH: 159
<212> TYPE: PRT
<213> ORGANISM: Rattus norvegicus

<400> SEQUENCE: 5

Ile Gln Met Thr Gln Ser Pro Gly Ser Leu Cys Ala Ser Leu Gly Glu
1               5                   10                  15

Thr Val Thr Ile Glu Cys Arg Ala Ser Asp Asp Ile Tyr Ser Asn Leu
            20                  25                  30

```
Ala Trp Tyr Gln Gln Lys Pro Gly Asn Ser Pro Gln Leu Leu Ile Phe
         35                  40                  45

Asp Gly Asn Arg Leu Ala Asp Gly Val Pro Ser Arg Phe Ser Gly Ser
 50                  55                  60

Gly Ser Gly Thr Gln Tyr Ser Leu Lys Met Lys Ser Leu Gln Phe Glu
 65                  70                  75                  80

Asp Val Ala Ser Tyr Phe Cys Gln Gln Tyr Asn Asn Tyr Pro Leu Thr
                 85                  90                  95

Phe Gly Ser Gly Thr Lys Leu Glu Ile Lys Arg Ala Asp Ala Ala Pro
             100                 105                 110

Thr Val Ser Ile Phe Pro Pro Ser Met Glu Gln Leu Thr Ser Gly Gly
         115                 120                 125

Ala Thr Val Val Cys Phe Val Asn Asn Phe Tyr Pro Arg Asp Ile Ser
 130                 135                 140

Val Lys Trp Lys Ile Asp Gly Ser Glu Gln Arg Asp Gly Val Leu
145                 150                 155
```

```
<210> SEQ ID NO 6
<211> LENGTH: 9
<212> TYPE: PRT
<213> ORGANISM: Rattus norvegicus

<400> SEQUENCE: 6

Gly Phe Thr Phe Ser Asn Phe Gly Met
1               5

<210> SEQ ID NO 7
<211> LENGTH: 9
<212> TYPE: PRT
<213> ORGANISM: Rattus norvegicus

<400> SEQUENCE: 7

Ser Ile Ser Ser Gly Gly Thr Tyr Ile
1               5

<210> SEQ ID NO 8
<211> LENGTH: 14
<212> TYPE: PRT
<213> ORGANISM: Rattus norvegicus

<400> SEQUENCE: 8

Gly Pro Tyr His Ser Arg Tyr Ile Pro Tyr Leu Met Asp Ala
1               5                   10

<210> SEQ ID NO 9
<211> LENGTH: 11
<212> TYPE: PRT
<213> ORGANISM: Rattus norvegicus

<400> SEQUENCE: 9

Arg Ala Ser Asp Asp Ile Tyr Ser Asn Leu Ala
1               5                   10

<210> SEQ ID NO 10
<211> LENGTH: 7
<212> TYPE: PRT
<213> ORGANISM: Rattus norvegicus

<400> SEQUENCE: 10

Asp Gly Asn Arg Leu Ala Asp
1               5
```

<210> SEQ ID NO 11
<211> LENGTH: 9
<212> TYPE: PRT
<213> ORGANISM: Rattus norvegicus

<400> SEQUENCE: 11

Gln Gln Tyr Asn Asn Tyr Pro Leu Thr
1               5

<210> SEQ ID NO 12
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer

<400> SEQUENCE: 12
ctcattcctg ttgaagctct tgacga                                        26

<210> SEQ ID NO 13
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer

<400> SEQUENCE: 13
aggcttgcaa tcacctccac a                                             21

<210> SEQ ID NO 14
<211> LENGTH: 671
<212> TYPE: PRT
<213> ORGANISM: Homo sapiens

<400> SEQUENCE: 14

Thr Pro Leu Gly Pro Lys Trp Pro Glu Pro Val Phe Gly Arg Leu Ala
1               5                   10                  15

Ser Pro Gly Phe Pro Gly Glu Tyr Ala Asn Asp Gln Glu Arg Arg Trp
                20                  25                  30

Thr Leu Thr Ala Pro Pro Gly Tyr Arg Leu Arg Leu Tyr Phe Thr His
            35                  40                  45

Phe Asp Leu Glu Leu Ser His Leu Cys Glu Tyr Asp Phe Val Lys Leu
    50                  55                  60

Ser Ser Gly Ala Lys Val Leu Ala Thr Leu Cys Gly Gln Glu Ser Thr
65                  70                  75                  80

Asp Thr Glu Arg Ala Pro Gly Lys Asp Thr Phe Tyr Ser Leu Gly Ser
                85                  90                  95

Ser Leu Asp Ile Thr Phe Arg Ser Asp Tyr Ser Asn Glu Lys Pro Phe
            100                 105                 110

Thr Gly Phe Glu Ala Phe Tyr Ala Ala Glu Asp Ile Asp Glu Cys Gln
        115                 120                 125

Val Ala Pro Gly Glu Ala Pro Thr Cys Asp His His Cys His Asn His
    130                 135                 140

Leu Gly Gly Phe Tyr Cys Ser Cys Arg Ala Gly Tyr Val Leu His Arg
145                 150                 155                 160

-continued

```
Asn Lys Arg Thr Cys Ser Ala Leu Cys Ser Gly Gln Val Phe Thr Gln
            165                 170                 175
Arg Ser Gly Glu Leu Ser Ser Pro Glu Tyr Pro Arg Pro Tyr Pro Lys
        180                 185                 190
Leu Ser Ser Cys Thr Tyr Ser Ile Ser Leu Glu Glu Gly Phe Ser Val
    195                 200                 205
Ile Leu Asp Phe Val Glu Ser Phe Asp Val Glu Thr His Pro Glu Thr
210                 215                 220
Leu Cys Pro Tyr Asp Phe Leu Lys Ile Gln Thr Asp Arg Glu Glu His
225                 230                 235                 240
Gly Pro Phe Cys Gly Lys Thr Leu Pro His Arg Ile Glu Thr Lys Ser
                245                 250                 255
Asn Thr Val Thr Ile Thr Phe Val Thr Asp Glu Ser Gly Asp His Thr
            260                 265                 270
Gly Trp Lys Ile His Tyr Thr Ser Thr Ala Gln Pro Cys Pro Tyr Pro
        275                 280                 285
Met Ala Pro Pro Asn Gly His Val Ser Pro Val Gln Ala Lys Tyr Ile
    290                 295                 300
Leu Lys Asp Ser Phe Ser Ile Phe Cys Glu Thr Gly Tyr Glu Leu Leu
305                 310                 315                 320
Gln Gly His Leu Pro Leu Lys Ser Phe Thr Ala Val Cys Gln Lys Asp
                325                 330                 335
Gly Ser Trp Asp Arg Pro Met Pro Ala Cys Ser Ile Val Asp Cys Gly
            340                 345                 350
Pro Pro Asp Asp Leu Pro Ser Gly Arg Val Glu Tyr Ile Thr Gly Pro
        355                 360                 365
Gly Val Thr Thr Tyr Lys Ala Val Ile Gln Tyr Ser Cys Glu Glu Thr
    370                 375                 380
Phe Tyr Thr Met Lys Val Asn Asp Gly Lys Tyr Val Cys Glu Ala Asp
385                 390                 395                 400
Gly Phe Trp Thr Ser Ser Lys Gly Glu Lys Ser Leu Pro Val Cys Glu
                405                 410                 415
Pro Val Cys Gly Leu Ser Ala Arg Thr Thr Gly Gly Arg Ile Tyr Gly
            420                 425                 430
Gly Gln Lys Ala Lys Pro Gly Asp Phe Pro Trp Gln Val Leu Ile Leu
        435                 440                 445
Gly Gly Thr Thr Ala Ala Gly Ala Leu Leu Tyr Asp Asn Trp Val Leu
    450                 455                 460
Thr Ala Ala His Ala Val Tyr Glu Gln Lys His Asp Ala Ser Ala Leu
465                 470                 475                 480
Asp Ile Arg Met Gly Thr Leu Lys Arg Leu Ser Pro His Tyr Thr Gln
                485                 490                 495
Ala Trp Ser Glu Ala Val Phe Ile His Glu Gly Tyr Thr His Asp Ala
            500                 505                 510
Gly Phe Asp Asn Asp Ile Ala Leu Ile Lys Leu Asn Asn Lys Val Val
        515                 520                 525
Ile Asn Ser Asn Ile Thr Pro Ile Cys Leu Pro Arg Lys Glu Ala Glu
    530                 535                 540
Ser Phe Met Arg Thr Asp Asp Ile Gly Thr Ala Ser Gly Trp Gly Leu
545                 550                 555                 560
Thr Gln Arg Gly Phe Leu Ala Arg Asn Leu Met Tyr Val Asp Ile Pro
                565                 570                 575
Ile Val Asp His Gln Lys Cys Thr Ala Ala Tyr Glu Lys Pro Pro Tyr
```

```
            580                 585                 590
Pro Arg Gly Ser Val Thr Ala Asn Met Leu Cys Ala Gly Leu Glu Ser
            595                 600                 605

Gly Gly Lys Asp Ser Cys Arg Gly Asp Ser Gly Gly Ala Leu Val Phe
        610                 615                 620

Leu Asp Ser Glu Thr Glu Arg Trp Phe Val Gly Ile Val Ser Trp
625                 630                 635                 640

Gly Ser Met Asn Cys Gly Glu Ala Gly Gln Tyr Gly Val Tyr Thr Lys
            645                 650                 655

Val Ile Asn Tyr Ile Pro Trp Ile Glu Asn Ile Ile Ser Asp Phe
        660                 665                 670

<210> SEQ ID NO 15
<211> LENGTH: 680
<212> TYPE: PRT
<213> ORGANISM: Homo sapiens

<400> SEQUENCE: 15

His Thr Val Glu Leu Asn Asn Met Phe Gly Gln Ile Gln Ser Pro Gly
1               5                   10                  15

Tyr Pro Asp Ser Tyr Pro Ser Asp Ser Glu Val Thr Trp Asn Ile Thr
            20                  25                  30

Val Pro Asp Gly Phe Arg Ile Lys Leu Tyr Phe Met His Phe Asn Leu
        35                  40                  45

Glu Ser Ser Tyr Leu Cys Glu Tyr Asp Tyr Val Lys Val Glu Thr Glu
    50                  55                  60

Asp Gln Val Leu Ala Thr Phe Cys Gly Arg Glu Thr Thr Asp Thr Glu
65                  70                  75                  80

Gln Thr Pro Gly Gln Glu Val Val Leu Ser Pro Gly Ser Phe Met Ser
                85                  90                  95

Ile Thr Phe Arg Ser Asp Phe Ser Asn Glu Glu Arg Phe Thr Gly Phe
            100                 105                 110

Asp Ala His Tyr Met Ala Val Asp Val Asp Glu Cys Lys Glu Arg Glu
        115                 120                 125

Asp Glu Glu Leu Ser Cys Asp His Tyr Cys His Asn Tyr Ile Gly Gly
    130                 135                 140

Tyr Tyr Cys Ser Cys Arg Phe Gly Tyr Ile Leu His Thr Asp Asn Arg
145                 150                 155                 160

Thr Cys Arg Val Glu Cys Ser Asp Asn Leu Phe Thr Gln Arg Thr Gly
                165                 170                 175

Val Ile Thr Ser Pro Asp Phe Pro Asn Pro Tyr Pro Lys Ser Ser Glu
            180                 185                 190

Cys Leu Tyr Thr Ile Glu Leu Glu Glu Gly Phe Met Val Asn Leu Gln
        195                 200                 205

Phe Glu Asp Ile Phe Asp Ile Glu Asp His Pro Glu Val Pro Cys Pro
    210                 215                 220

Tyr Asp Tyr Ile Lys Ile Lys Val Gly Pro Lys Val Leu Gly Pro Phe
225                 230                 235                 240

Cys Gly Glu Lys Ala Pro Glu Pro Ile Ser Thr Gln Ser His Ser Val
                245                 250                 255

Leu Ile Leu Phe His Ser Asp Asn Ser Gly Glu Asn Arg Gly Trp Arg
            260                 265                 270

Leu Ser Tyr Arg Ala Ala Gly Asn Glu Cys Pro Glu Leu Gln Pro Pro
        275                 280                 285
```

```
Val His Gly Lys Ile Glu Pro Ser Gln Ala Lys Tyr Phe Phe Lys Asp
    290                 295                 300

Gln Val Leu Val Ser Cys Asp Thr Gly Tyr Lys Val Leu Lys Asp Asn
305                 310                 315                 320

Val Glu Met Asp Thr Phe Gln Ile Glu Cys Leu Lys Asp Gly Thr Trp
                325                 330                 335

Ser Asn Lys Ile Pro Thr Cys Lys Ile Val Asp Cys Arg Ala Pro Gly
            340                 345                 350

Glu Leu Glu His Gly Leu Ile Thr Phe Ser Thr Arg Asn Asn Leu Thr
        355                 360                 365

Thr Tyr Lys Ser Glu Ile Lys Tyr Ser Cys Gln Glu Pro Tyr Tyr Lys
370                 375                 380

Met Leu Asn Asn Asn Thr Gly Ile Tyr Thr Cys Ser Ala Gln Gly Val
385                 390                 395                 400

Trp Met Asn Lys Val Leu Gly Arg Ser Leu Pro Thr Cys Leu Pro Val
                405                 410                 415

Cys Gly Leu Pro Lys Phe Ser Arg Lys Leu Met Ala Arg Ile Phe Asn
            420                 425                 430

Gly Arg Pro Ala Gln Lys Gly Thr Thr Pro Trp Ile Ala Met Leu Ser
        435                 440                 445

His Leu Asn Gly Gln Pro Phe Cys Gly Gly Ser Leu Leu Gly Ser Ser
450                 455                 460

Trp Ile Val Thr Ala Ala His Cys Leu His Gln Ser Leu Asp Pro Lys
465                 470                 475                 480

Asp Pro Thr Leu Arg Asp Ser Asp Leu Leu Ser Pro Ser Asp Phe Lys
                485                 490                 495

Ile Ile Leu Gly Lys His Trp Arg Leu Arg Ser Asp Glu Asn Glu Gln
            500                 505                 510

His Leu Gly Val Lys His Thr Thr Leu His Pro Lys Tyr Asp Pro Asn
        515                 520                 525

Thr Phe Glu Asn Asp Val Ala Leu Val Glu Leu Leu Gly Ser Pro Val
530                 535                 540

Leu Asn Ala Phe Val Met Pro Ile Cys Leu Pro Glu Gly Pro Gln Gln
545                 550                 555                 560

Glu Gly Ala Met Val Ile Val Ser Gly Trp Gly Lys Gln Phe Leu Gln
                565                 570                 575

Arg Phe Pro Glu Thr Leu Met Glu Ile Glu Ile Pro Ile Val Asp His
            580                 585                 590

Ser Thr Cys Gln Lys Ala Tyr Ala Pro Leu Lys Lys Lys Val Thr Arg
        595                 600                 605

Asp Met Ile Cys Ala Gly Glu Lys Glu Gly Gly Lys Asp Ala Cys Ser
610                 615                 620

Gly Asp Ser Gly Gly Pro Met Val Thr Leu Asn Arg Glu Arg Gly Gln
625                 630                 635                 640

Trp Tyr Leu Val Gly Thr Val Ser Trp Gly Asp Asp Cys Gly Lys Lys
                645                 650                 655

Asp Arg Tyr Gly Val Tyr Ser Tyr Ile His His Asn Lys Asp Trp Ile
            660                 665                 670

Gln Arg Val Thr Gly Val Arg Asn
        675                 680

<210> SEQ ID NO 16
<211> LENGTH: 688
<212> TYPE: PRT
```

-continued

<213> ORGANISM: Homo sapiens

<400> SEQUENCE: 16

```
Ser Ile Pro Ile Pro Gln Lys Leu Phe Gly Glu Val Thr Ser Pro Leu
1               5                   10                  15

Phe Pro Lys Pro Tyr Pro Asn Asn Phe Glu Thr Thr Thr Val Ile Thr
            20                  25                  30

Val Pro Thr Gly Tyr Arg Val Lys Leu Val Phe Gln Gln Phe Asp Leu
        35                  40                  45

Glu Pro Ser Glu Gly Cys Phe Tyr Asp Tyr Val Lys Ile Ser Ala Asp
    50                  55                  60

Lys Lys Ser Leu Gly Arg Phe Cys Gly Gln Leu Gly Ser Pro Leu Gly
65                  70                  75                  80

Asn Pro Pro Gly Lys Lys Glu Phe Met Ser Gln Gly Asn Lys Met Leu
                85                  90                  95

Leu Thr Phe His Thr Asp Phe Ser Asn Glu Glu Asn Gly Thr Ile Met
            100                 105                 110

Phe Tyr Lys Gly Phe Leu Ala Tyr Tyr Gln Ala Val Asp Leu Asp Glu
        115                 120                 125

Cys Ala Ser Arg Ser Lys Ser Gly Glu Glu Asp Pro Gln Pro Gln Cys
    130                 135                 140

Gln His Leu Cys His Asn Tyr Val Gly Gly Tyr Phe Cys Ser Cys Arg
145                 150                 155                 160

Pro Gly Tyr Glu Leu Gln Glu Asp Arg His Ser Cys Gln Ala Glu Cys
                165                 170                 175

Ser Ser Glu Leu Tyr Thr Glu Ala Ser Gly Tyr Ile Ser Ser Leu Glu
            180                 185                 190

Tyr Pro Arg Ser Tyr Pro Pro Asp Leu Arg Cys Asn Tyr Ser Ile Arg
        195                 200                 205

Val Glu Arg Gly Leu Thr Leu His Leu Lys Phe Leu Glu Pro Phe Asp
    210                 215                 220

Ile Asp Asp His Gln Gln Val His Cys Pro Tyr Asp Gln Leu Gln Ile
225                 230                 235                 240

Tyr Ala Asn Gly Lys Asn Ile Gly Glu Phe Cys Gly Lys Gln Arg Pro
                245                 250                 255

Pro Asp Leu Asp Thr Ser Ser Asn Ala Val Asp Leu Leu Phe Phe Thr
            260                 265                 270

Asp Glu Ser Gly Asp Ser Arg Gly Trp Lys Leu Arg Tyr Thr Thr Glu
        275                 280                 285

Ile Ile Lys Cys Pro Gln Pro Lys Thr Leu Asp Glu Phe Thr Ile Ile
    290                 295                 300

Gln Asn Leu Gln Pro Gln Tyr Gln Phe Arg Asp Tyr Phe Ile Ala Thr
305                 310                 315                 320

Cys Lys Gln Gly Tyr Gln Leu Ile Glu Gly Asn Gln Val Leu His Ser
                325                 330                 335

Phe Thr Ala Val Cys Gln Asp Asp Gly Thr Trp His Arg Ala Met Pro
            340                 345                 350

Arg Cys Lys Ile Lys Asp Cys Gly Gln Pro Arg Asn Leu Pro Asn Gly
        355                 360                 365

Asp Phe Arg Tyr Thr Thr Thr Met Gly Val Asn Thr Tyr Lys Ala Arg
    370                 375                 380

Ile Gln Tyr Tyr Cys His Glu Pro Tyr Tyr Lys Met Gln Thr Arg Ala
385                 390                 395                 400
```

-continued

Gly Ser Arg Glu Ser Glu Gln Gly Val Tyr Thr Cys Thr Ala Gln Gly
               405                 410                 415

Ile Trp Lys Asn Glu Gln Lys Gly Glu Lys Ile Pro Arg Cys Leu Pro
            420                 425                 430

Val Cys Gly Lys Pro Val Asn Pro Val Glu Gln Arg Gln Arg Ile Ile
        435                 440                 445

Gly Gly Gln Lys Ala Lys Met Gly Asn Phe Pro Trp Gln Val Phe Thr
    450                 455                 460

Asn Ile His Gly Arg Gly Gly Ala Leu Leu Gly Asp Arg Trp Ile
465                 470                 475                 480

Leu Thr Ala Ala His Thr Leu Tyr Pro Lys Glu His Glu Ala Gln Ser
                485                 490                 495

Asn Ala Ser Leu Asp Val Phe Leu Gly His Thr Asn Val Glu Glu Leu
            500                 505                 510

Met Lys Leu Gly Asn His Pro Ile Arg Arg Val Ser Val His Pro Asp
        515                 520                 525

Tyr Arg Gln Asp Glu Ser Tyr Asn Phe Glu Gly Asp Ile Ala Leu Leu
    530                 535                 540

Glu Leu Glu Asn Ser Val Thr Leu Gly Pro Asn Leu Leu Pro Ile Cys
545                 550                 555                 560

Leu Pro Asp Asn Asp Thr Phe Tyr Asp Leu Gly Leu Met Gly Tyr Val
                565                 570                 575

Ser Gly Phe Gly Val Met Glu Glu Lys Ile Ala His Asp Leu Arg Phe
            580                 585                 590

Val Arg Leu Pro Val Ala Asn Pro Gln Ala Cys Glu Asn Trp Leu Arg
        595                 600                 605

Gly Lys Asn Arg Met Asp Val Phe Ser Gln Asn Met Phe Cys Ala Gly
    610                 615                 620

His Pro Ser Leu Lys Gln Asp Ala Cys Gln Gly Asp Ser Gly Gly Val
625                 630                 635                 640

Phe Ala Val Arg Asp Pro Asn Thr Asp Arg Trp Val Ala Thr Gly Ile
                645                 650                 655

Val Ser Trp Gly Ile Gly Cys Ser Arg Gly Tyr Gly Phe Tyr Thr Lys
            660                 665                 670

Val Leu Asn Tyr Val Asp Trp Ile Lys Lys Glu Met Glu Glu Glu Asp
        675                 680                 685

<210> SEQ ID NO 17
<211> LENGTH: 673
<212> TYPE: PRT
<213> ORGANISM: Homo sapiens

<400> SEQUENCE: 17

Glu Pro Thr Met Tyr Gly Glu Ile Leu Ser Pro Asn Tyr Pro Gln Ala
1               5                   10                  15

Tyr Pro Ser Glu Val Glu Lys Ser Trp Asp Ile Glu Val Pro Glu Gly
            20                  25                  30

Tyr Gly Ile His Leu Tyr Phe Thr His Leu Asp Ile Glu Leu Ser Glu
        35                  40                  45

Asn Cys Ala Tyr Asp Ser Val Gln Ile Ile Ser Gly Asp Thr Glu Glu
    50                  55                  60

Gly Arg Leu Cys Gly Gln Arg Ser Ser Asn Pro His Ser Pro Ile
65                  70                  75                  80

Val Glu Glu Phe Gln Val Pro Tyr Asn Lys Leu Gln Val Ile Phe Lys
                85                  90                  95

-continued

```
Ser Asp Phe Ser Asn Glu Glu Arg Phe Thr Gly Phe Ala Ala Tyr Tyr
            100                 105                 110

Val Ala Thr Asp Ile Asn Glu Cys Thr Asp Phe Val Asp Val Pro Cys
            115                 120                 125

Ser His Phe Cys Asn Asn Phe Ile Gly Gly Tyr Phe Cys Ser Cys Pro
            130                 135                 140

Pro Glu Tyr Phe Leu His Asp Asp Met Lys Asn Cys Gly Val Asn Cys
145                 150                 155                 160

Ser Gly Asp Val Phe Thr Ala Leu Ile Gly Glu Ile Ala Ser Pro Asn
                165                 170                 175

Tyr Pro Lys Pro Tyr Pro Glu Asn Ser Arg Cys Glu Tyr Gln Ile Arg
            180                 185                 190

Leu Glu Lys Gly Phe Gln Val Val Thr Leu Arg Arg Glu Asp Phe
            195                 200                 205

Asp Val Glu Ala Ala Asp Ser Ala Gly Asn Cys Leu Asp Ser Leu Val
            210                 215                 220

Phe Val Ala Gly Asp Arg Gln Phe Gly Pro Tyr Cys Gly His Gly Phe
225                 230                 235                 240

Pro Gly Pro Leu Asn Ile Glu Thr Lys Ser Asn Ala Leu Asp Ile Ile
                245                 250                 255

Phe Gln Thr Asp Leu Thr Gly Gln Lys Lys Gly Trp Lys Leu Arg Tyr
            260                 265                 270

His Gly Asp Pro Met Pro Cys Pro Lys Glu Asp Thr Pro Asn Ser Val
            275                 280                 285

Trp Glu Pro Ala Lys Ala Lys Tyr Val Phe Arg Asp Val Val Gln Ile
            290                 295                 300

Thr Cys Leu Asp Gly Phe Glu Val Val Glu Gly Arg Val Gly Ala Thr
305                 310                 315                 320

Ser Phe Tyr Ser Thr Cys Gln Ser Asn Gly Lys Trp Ser Asn Ser Lys
                325                 330                 335

Leu Lys Cys Gln Pro Val Asp Cys Gly Ile Pro Glu Ser Ile Glu Asn
            340                 345                 350

Gly Lys Val Glu Asp Pro Glu Ser Thr Leu Phe Gly Ser Val Ile Arg
            355                 360                 365

Tyr Thr Cys Glu Glu Pro Tyr Tyr Tyr Met Glu Asn Gly Gly Gly Gly
            370                 375                 380

Glu Tyr His Cys Ala Gly Asn Gly Ser Trp Val Asn Glu Val Leu Gly
385                 390                 395                 400

Pro Glu Leu Pro Lys Cys Val Pro Val Cys Gly Val Pro Arg Glu Pro
                405                 410                 415

Phe Glu Glu Lys Gln Arg Ile Ile Gly Gly Ser Asp Ala Asp Ile Lys
            420                 425                 430

Asn Phe Pro Trp Gln Val Phe Phe Asp Asn Pro Trp Ala Gly Gly Ala
            435                 440                 445

Leu Ile Asn Glu Tyr Trp Val Leu Thr Ala Ala His Val Val Glu Gly
            450                 455                 460

Asn Arg Glu Pro Thr Met Tyr Val Gly Ser Thr Ser Val Gln Thr Ser
465                 470                 475                 480

Arg Leu Ala Lys Ser Lys Met Leu Thr Pro Glu His Val Phe Ile His
                485                 490                 495

Pro Gly Trp Lys Leu Leu Glu Val Pro Glu Gly Arg Thr Asn Phe Asp
            500                 505                 510
```

```
Asn Asp Ile Ala Leu Val Arg Leu Lys Asp Pro Val Lys Met Gly Pro
            515                 520                 525

Thr Val Ser Pro Ile Cys Leu Pro Gly Thr Ser Asp Tyr Asn Leu
530                 535                 540

Met Asp Gly Asp Leu Gly Leu Ile Ser Gly Trp Gly Arg Thr Glu Lys
545                 550                 555                 560

Arg Asp Arg Ala Val Arg Leu Lys Ala Ala Arg Leu Pro Val Ala Pro
                565                 570                 575

Leu Arg Lys Cys Lys Glu Val Lys Val Glu Lys Pro Thr Ala Asp Ala
            580                 585                 590

Glu Ala Tyr Val Phe Thr Pro Asn Met Ile Cys Ala Gly Gly Glu Lys
        595                 600                 605

Gly Met Asp Ser Cys Lys Gly Asp Ser Gly Gly Ala Phe Ala Val Gln
    610                 615                 620

Asp Pro Asn Asp Lys Thr Lys Phe Tyr Ala Ala Gly Leu Val Ser Trp
625                 630                 635                 640

Gly Pro Gln Cys Gly Thr Tyr Gly Leu Tyr Thr Arg Val Lys Asn Tyr
                645                 650                 655

Val Asp Trp Ile Met Lys Thr Met Gln Glu Asn Ser Thr Pro Arg Glu
            660                 665                 670

Asp

<210> SEQ ID NO 18
<211> LENGTH: 824
<212> TYPE: DNA
<213> ORGANISM: Rattus norvegicus
<220> FEATURE:
<221> NAME/KEY: CDS
<222> LOCATION: (90)..(824)

<400> SEQUENCE: 18
aattcgccct tctaatacga ctcactatag ggcaagcagt ggtatcaacg cagagtacgc      60
ggggagtctc acagaggtca cacacagac atg ggt gtc ccc act cag ctc ctg     113
                                 Met Gly Val Pro Thr Gln Leu Leu
                                  1               5 ggg ttg ttg cta ctg tgg ata aca gat gcc ata tgt gac atc cag atg     161
Gly Leu Leu Leu Leu Trp Ile Thr Asp Ala Ile Cys Asp Ile Gln Met
 10                  15                  20 aca cag tct cca ggt tcc ctg tgt gca tct ctg gga gaa act gtc acc     209
Thr Gln Ser Pro Gly Ser Leu Cys Ala Ser Leu Gly Glu Thr Val Thr
25                  30                  35                  40 atc gaa tgt cga gca agt gac gac att tac agt aat tta gcg tgg tat     257
Ile Glu Cys Arg Ala Ser Asp Asp Ile Tyr Ser Asn Leu Ala Trp Tyr
                45                  50                  55 cag caa aaa cca ggg aac tct cct cag ctc ctg atc ttt gat gga aat     305
Gln Gln Lys Pro Gly Asn Ser Pro Gln Leu Leu Ile Phe Asp Gly Asn
            60                  65                  70 cgg ttg gca gat ggg gtc cca tca cga ttc agt ggc agt gga tct ggc     353
Arg Leu Ala Asp Gly Val Pro Ser Arg Phe Ser Gly Ser Gly Ser Gly
        75                  80                  85 aca cag tat tct cta aag atg aag agc ctg caa ttt gaa gat gtc gca     401
Thr Gln Tyr Ser Leu Lys Met Lys Ser Leu Gln Phe Glu Asp Val Ala
    90                  95                  100 agt tat ttc tgt caa cag tat aat aat tat ccg ctc acg ttc ggt tct     449
Ser Tyr Phe Cys Gln Gln Tyr Asn Asn Tyr Pro Leu Thr Phe Gly Ser
105                 110                 115                 120 ggg acc aag ctg gag atc aaa cgg gct gat gct gca cca act gta tcc     497
Gly Thr Lys Leu Glu Ile Lys Arg Ala Asp Ala Ala Pro Thr Val Ser
```

```
                    125                 130                 135
atc ttc cca cca tcc atg gaa cag tta aca tct gga ggt gcc aca gtc      545
Ile Phe Pro Pro Ser Met Glu Gln Leu Thr Ser Gly Gly Ala Thr Val
        140                 145                 150 gtg tgc ttc gtg aac aac ttc tat ccc aga gac atc agt gtc aag tgg      593
Val Cys Phe Val Asn Asn Phe Tyr Pro Arg Asp Ile Ser Val Lys Trp
            155                 160                 165 aag att gat ggc agt gaa caa cga gat ggt gtc ctg gac agt gtt act      641
Lys Ile Asp Gly Ser Glu Gln Arg Asp Gly Val Leu Asp Ser Val Thr
        170                 175                 180 gat cag gac agc aaa gac agc acg tac agc atg agc agc acc ctc tcg      689
Asp Gln Asp Ser Lys Asp Ser Thr Tyr Ser Met Ser Ser Thr Leu Ser
185                 190                 195                 200 ttg acc aag gtt gaa tat gaa agg cat aac ctc tat acc tgt gag gtt      737
Leu Thr Lys Val Glu Tyr Glu Arg His Asn Leu Tyr Thr Cys Glu Val
                205                 210                 215 gtt cat aag aca tca tcc tca ccc gtc gtc aag agc ttc aac agg aat      785
Val His Lys Thr Ser Ser Ser Pro Val Val Lys Ser Phe Asn Arg Asn
            220                 225                 230 gag aag ggc gaa ttc cag cac act ggc ggc cgt tac tag                  824
Glu Lys Gly Glu Phe Gln His Thr Gly Gly Arg Tyr
        235                 240

<210> SEQ ID NO 19
<211> LENGTH: 244
<212> TYPE: PRT
<213> ORGANISM: Rattus norvegicus

<400> SEQUENCE: 19

Met Gly Val Pro Thr Gln Leu Leu Gly Leu Leu Leu Leu Trp Ile Thr
1               5                   10                  15

Asp Ala Ile Cys Asp Ile Gln Met Thr Gln Ser Pro Gly Ser Leu Cys
            20                  25                  30

Ala Ser Leu Gly Glu Thr Val Thr Ile Glu Cys Arg Ala Ser Asp Asp
        35                  40                  45

Ile Tyr Ser Asn Leu Ala Trp Tyr Gln Gln Lys Pro Gly Asn Ser Pro
    50                  55                  60

Gln Leu Leu Ile Phe Asp Gly Asn Arg Leu Ala Asp Gly Val Pro Ser
65                  70                  75                  80

Arg Phe Ser Gly Ser Gly Ser Gly Thr Gln Tyr Ser Leu Lys Met Lys
                85                  90                  95

Ser Leu Gln Phe Glu Asp Val Ala Ser Tyr Phe Cys Gln Gln Tyr Asn
            100                 105                 110

Asn Tyr Pro Leu Thr Phe Gly Ser Gly Thr Lys Leu Glu Ile Lys Arg
        115                 120                 125

Ala Asp Ala Ala Pro Thr Val Ser Ile Phe Pro Pro Ser Met Glu Gln
    130                 135                 140

Leu Thr Ser Gly Gly Ala Thr Val Val Cys Phe Val Asn Asn Phe Tyr
145                 150                 155                 160

Pro Arg Asp Ile Ser Val Lys Trp Lys Ile Asp Gly Ser Glu Gln Arg
                165                 170                 175

Asp Gly Val Leu Asp Ser Val Thr Asp Gln Asp Ser Lys Asp Ser Thr
            180                 185                 190

Tyr Ser Met Ser Ser Thr Leu Ser Leu Thr Lys Val Glu Tyr Glu Arg
        195                 200                 205

His Asn Leu Tyr Thr Cys Glu Val Val His Lys Thr Ser Ser Ser Pro
    210                 215                 220
```

```
Val Val Lys Ser Phe Asn Arg Asn Glu Lys Gly Glu Phe Gln His Thr
225                 230                 235                 240

Gly Gly Arg Tyr

<210> SEQ ID NO 20
<211> LENGTH: 927
<212> TYPE: DNA
<213> ORGANISM: Rattus norvegicus
<220> FEATURE:
<221> NAME/KEY: CDS
<222> LOCATION: (163)..(927)

<400> SEQUENCE: 20
gcatgctcga gcggccgcca gtgtgatgga tatctgcaga attcgcccct ctaataccga      60
ctcactatag ggcaagcagt ggtatcaacg cagagtccgc gggggacccc tggttttcca     120
ggtcctcaca ttcagtgatc tgcactgcac agaccatcca cc atg agt ttc agc       174
                                              Met Ser Phe Ser
                                              1 aac acc ttg gtt ttc ctt ttg ttt ctt tta aaa ggt atc ctg tgt gag      222
Asn Thr Leu Val Phe Leu Leu Phe Leu Leu Lys Gly Ile Leu Cys Glu
5               10                  15                  20 gtg cag ctg gtg gag cct gga gga ggc tta gtg cag cct gga agg tcc      270
Val Gln Leu Val Glu Pro Gly Gly Gly Leu Val Gln Pro Gly Arg Ser
            25                  30                  35 ctg aaa ctc tcc tgt tta gtc tct gga ttc act ttc agt aac ttt gga      318
Leu Lys Leu Ser Cys Leu Val Ser Gly Phe Thr Phe Ser Asn Phe Gly
        40                  45                  50 atg aac tgg att cgc cag gct cca ggg aag gga ctg gag tgg gtt gca      366
Met Asn Trp Ile Arg Gln Ala Pro Gly Lys Gly Leu Glu Trp Val Ala
    55                  60                  65 tct atc agt agt ggt ggt act tat atc tac cat gca gac aca ttg aag      414
Ser Ile Ser Ser Gly Gly Thr Tyr Ile Tyr His Ala Asp Thr Leu Lys
70                  75                  80 ggc cga ttc acc atc tcc aga gaa aat gcc aag aac acc ctg tac ctg      462
Gly Arg Phe Thr Ile Ser Arg Glu Asn Ala Lys Asn Thr Leu Tyr Leu
85                  90                  95                  100 caa atg acc agt ctg agg tct gaa gac act gcc ttg tat tac tgt gca      510
Gln Met Thr Ser Leu Arg Ser Glu Asp Thr Ala Leu Tyr Tyr Cys Ala
            105                 110                 115 aga ggg cct tac cat agc agg tat atc ccc tat ctt atg gat gcc tgg      558
Arg Gly Pro Tyr His Ser Arg Tyr Ile Pro Tyr Leu Met Asp Ala Trp
        120                 125                 130 ggt caa gga gct tca gtc act gtc tcc tca gct gaa aca aca gcc cca      606
Gly Gln Gly Ala Ser Val Thr Val Ser Ser Ala Glu Thr Thr Ala Pro
    135                 140                 145 tct gtc tat cca ctg gct cct gga act gct ctc aaa agt agc tcc atg      654
Ser Val Tyr Pro Leu Ala Pro Gly Thr Ala Leu Lys Ser Ser Ser Met
150                 155                 160 gtg acc ctg gga tgc ctg gtc aag ggc tat ttc cct gag cca gtc acc      702
Val Thr Leu Gly Cys Leu Val Lys Gly Tyr Phe Pro Glu Pro Val Thr
165                 170                 175                 180 gtg acc tgg aac tct gga gcc ctg tcc agc ggt gtg cac acc ttc cca      750
Val Thr Trp Asn Ser Gly Ala Leu Ser Ser Gly Val His Thr Phe Pro
            185                 190                 195 gct gtc ctg cag tct ggg ctc tac act ctc acc agc tca gtg act gta      798
Ala Val Leu Gln Ser Gly Leu Tyr Thr Leu Thr Ser Ser Val Thr Val
        200                 205                 210 ccc tcc agc acc tgg ccc agc cag acc gtc acc tgc aac gta gcc cac      846
Pro Ser Ser Thr Trp Pro Ser Gln Thr Val Thr Cys Asn Val Ala His
    215                 220                 225
```

```
                215                 220                 225
ccg gcc agc agc acc aag gtg gac aag aaa att gtg ccc aga aac tgt    894
Pro Ala Ser Ser Thr Lys Val Asp Lys Lys Ile Val Pro Arg Asn Cys
    230                 235                 240 gga ggt gat tgc aag cct aag ggc gaa ttc cag                        927
Gly Gly Asp Cys Lys Pro Lys Gly Glu Phe Gln
245                 250                 255

<210> SEQ ID NO 21
<211> LENGTH: 255
<212> TYPE: PRT
<213> ORGANISM: Rattus norvegicus

<400> SEQUENCE: 21

Met Ser Phe Ser Asn Thr Leu Val Phe Leu Leu Phe Leu Leu Lys Gly
1               5                   10                  15

Ile Leu Cys Glu Val Gln Leu Val Glu Pro Gly Gly Gly Leu Val Gln
                20                  25                  30

Pro Gly Arg Ser Leu Lys Leu Ser Cys Leu Val Ser Gly Phe Thr Phe
            35                  40                  45

Ser Asn Phe Gly Met Asn Trp Ile Arg Gln Ala Pro Gly Lys Gly Leu
        50                  55                  60

Glu Trp Val Ala Ser Ile Ser Ser Gly Gly Thr Tyr Ile Tyr His Ala
65                  70                  75                  80

Asp Thr Leu Lys Gly Arg Phe Thr Ile Ser Arg Glu Asn Ala Lys Asn
                85                  90                  95

Thr Leu Tyr Leu Gln Met Thr Ser Leu Arg Ser Glu Asp Thr Ala Leu
            100                 105                 110

Tyr Tyr Cys Ala Arg Gly Pro Tyr His Ser Arg Tyr Ile Pro Tyr Leu
        115                 120                 125

Met Asp Ala Trp Gly Gln Gly Ala Ser Val Thr Val Ser Ser Ala Glu
130                 135                 140

Thr Thr Ala Pro Ser Val Tyr Pro Leu Ala Pro Gly Thr Ala Leu Lys
145                 150                 155                 160

Ser Ser Ser Met Val Thr Leu Gly Cys Leu Val Lys Gly Tyr Phe Pro
                165                 170                 175

Glu Pro Val Thr Val Thr Trp Asn Ser Gly Ala Leu Ser Ser Gly Val
            180                 185                 190

His Thr Phe Pro Ala Val Leu Gln Ser Gly Leu Tyr Thr Leu Thr Ser
        195                 200                 205

Ser Val Thr Val Pro Ser Ser Thr Trp Pro Ser Gln Thr Val Thr Cys
    210                 215                 220

Asn Val Ala His Pro Ala Ser Ser Thr Lys Val Asp Lys Lys Ile Val
225                 230                 235                 240

Pro Arg Asn Cys Gly Gly Asp Cys Lys Pro Lys Gly Glu Phe Gln
                245                 250                 255

<210> SEQ ID NO 22
<211> LENGTH: 117
<212> TYPE: PRT
<213> ORGANISM: Artificial Sequence
<220> FEATURE:
<223> OTHER INFORMATION: Synthetic

<400> SEQUENCE: 22

Met Asn Phe Gly Leu Ser Leu Ile Phe Leu Val Leu Val Leu Lys Gly
1               5                   10                  15
```

```
Val Leu Cys Glu Val Lys Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Ser Tyr Thr Met Ser Trp Val Arg Gln Thr Pro Glu Lys Arg Leu
50                  55                  60

Glu Trp Val Ala Tyr Ile Ser Asn Gly Gly Gly Ser Thr Tyr Tyr Pro
65                  70                  75                  80

Asp Thr Val Lys Gly Arg Phe Thr Ile Ser Arg Asp Asn Ala Lys Asn
                85                  90                  95

Asn Leu Tyr Leu Gln Met Ser Ser Leu Lys Ser Glu Asp Thr Ala Met
            100                 105                 110

Tyr Tyr Cys Ala Arg
        115

<210> SEQ ID NO 23
<211> LENGTH: 117
<212> TYPE: PRT
<213> ORGANISM: Artificial Sequence
<220> FEATURE:
<223> OTHER INFORMATION: Synthetic

<400> SEQUENCE: 23

Met Asn Phe Gly Leu Arg Leu Ile Phe Leu Val Leu Thr Leu Lys Gly
1               5                   10                  15

Val Lys Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Ala Phe
        35                  40                  45

Ser Ser Tyr Asp Met Ser Trp Val Arg Gln Thr Pro Glu Lys Arg Leu
50                  55                  60

Glu Trp Val Ala Tyr Ile Ser Ser Gly Gly Gly Ser Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg
        115

<210> SEQ ID NO 24
<211> LENGTH: 117
<212> TYPE: PRT
<213> ORGANISM: Artificial Sequence
<220> FEATURE:
<223> OTHER INFORMATION: Synthetic

<400> SEQUENCE: 24

Met Asn Phe Val Leu Ser Leu Ile Phe Leu Ala Leu Ile Leu Lys Gly
1               5                   10                  15

Val Gln Cys Glu Val His Leu Val Glu Ser Gly Gly Gly Leu Val Lys
            20                  25                  30

Pro Gly Gly Ser Leu Lys Leu Ser Cys Val Val Ser Gly Phe Thr Phe
        35                  40                  45

Asn Lys Tyr Ala Met Ser Trp Val Arg Gln Thr Pro Glu Lys Arg Leu
50                  55                  60

Glu Trp Val Ala Thr Ile Ser Ser Gly Gly Leu Tyr Thr Tyr Tyr Pro
65                  70                  75                  80
```

```
Asp Ser Val Lys Gly Arg Phe Thr Ile Ser Arg Asp Asn Ala Gly Asn
                85                  90                  95

Thr Leu Tyr Leu Gln Met Ser Ser Leu Arg Ser Glu Asp Thr Ala Met
            100                 105                 110

Tyr Tyr Cys Ala Arg
        115

<210> SEQ ID NO 25
<211> LENGTH: 117
<212> TYPE: PRT
<213> ORGANISM: Artificial Sequence
<220> FEATURE:
<223> OTHER INFORMATION: Synthetic

<400> SEQUENCE: 25

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Gly
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys
        115

<210> SEQ ID NO 26
<211> LENGTH: 136
<212> TYPE: PRT
<213> ORGANISM: Artificial Sequence
<220> FEATURE:
<223> OTHER INFORMATION: Synthetic

<400> SEQUENCE: 26

Arg Leu Asn Leu Val Phe Leu Val Leu Ile Leu Lys Gly Val Gln Cys
1               5                   10                  15

Asp Val Gln Leu Val Glu Ser Gly Gly Gly Leu Val Gln Pro Gly Gly
            20                  25                  30

Ser Arg Lys Leu Ser Cys Ala Ala Ser Gly Phe Thr Phe Ser Ser Phe
        35                  40                  45

Gly Met His Trp Val Arg Gln Ala Pro Glu Lys Gly Leu Glu Trp Val
    50                  55                  60

Ala Tyr Ile Ser Ser Gly Ser Ser Thr Leu His Tyr Ala Asp Thr Val
65                  70                  75                  80

Lys Gly Arg Phe Thr Ile Ser Arg Asp Asn Pro Lys Asn Thr Leu Phe
                85                  90                  95

Leu Gln Met Thr Ser Leu Arg Ser Glu Asp Thr Ala Met Tyr Tyr Cys
            100                 105                 110

Ala Arg Trp Gly Asn Tyr Pro Tyr Tyr Ala Met Asp Tyr Trp Gly Gln
        115                 120                 125

Gly Thr Ser Val Thr Val Ser Ser
```

<210> SEQ ID NO 27
<211> LENGTH: 240
<212> TYPE: PRT
<213> ORGANISM: Rattus norvegicus

<400> SEQUENCE: 27

Met Ser Phe Ser Asn Thr Leu Val Phe Leu Leu Phe Leu Leu Lys Gly
1               5                   10                  15

Ile Leu Cys Glu Val Gln Leu Val Glu Ser Gly Gly Gly Leu Val Gln
            20                  25                  30

Pro Gly Arg Ser Leu Lys Leu Ser Cys Leu Val Ser Gly Phe Thr Phe
        35                  40                  45

Ser Asn Phe Gly Met Asn Trp Ile Arg Gln Ala Pro Gly Lys Gly Leu
    50                  55                  60

Glu Trp Val Ala Ser Ile Ser Ser Gly Gly Thr Tyr Ile Tyr His Ala
65                  70                  75                  80

Asp Thr Leu Lys Gly Arg Phe Thr Ile Ser Arg Glu Asn Ala Lys Asn
                85                  90                  95

Thr Leu Tyr Leu Gln Met Thr Ser Leu Arg Ser Glu Asp Thr Ala Leu
            100                 105                 110

Tyr Tyr Cys Ala Arg Gly Pro Tyr His Ser Arg Tyr Ile Pro Tyr Leu
        115                 120                 125

Met Asp Ala Trp Gly Gln Gly Ala Ser Val Thr Val Ser Ser Ala Glu
    130                 135                 140

Thr Thr Ala Pro Ser Val Tyr Pro Leu Ala Pro Gly Thr Ala Leu Lys
145                 150                 155                 160

Ser Asn Ser Met Val Thr Leu Gly Cys Leu Val Lys Gly Tyr Phe Pro
                165                 170                 175

Glu Pro Val Thr Val Thr Trp Asn Ser Gly Ala Leu Ser Ser Gly Val
            180                 185                 190

His Thr Phe Pro Ala Val Leu Gln Ser Gly Leu Tyr Thr Leu Thr Ser
        195                 200                 205

Ser Val Thr Val Pro Ser Ser Thr Trp Pro Ser Gln Thr Val Thr Cys
    210                 215                 220

Asn Val Ala His Pro Ala Ser Ser Thr Lys Val Asp Lys Lys Ile Val
225                 230                 235                 240

<210> SEQ ID NO 28
<211> LENGTH: 240
<212> TYPE: PRT
<213> ORGANISM: Rattus norvegicus

<400> SEQUENCE: 28

Met Ser Phe Ser Asn Thr Leu Val Phe Leu Leu Phe Leu Leu Lys Gly
1               5                   10                  15

Ile Leu Cys Glu Val Gln Leu Val Glu Ser Gly Gly Gly Leu Val Gln
            20                  25                  30

Pro Gly Arg Ser Leu Lys Leu Ser Cys Leu Val Ser Gly Phe Thr Phe
        35                  40                  45

Ser Asn Phe Gly Met Asn Trp Ile Arg Gln Ala Pro Gly Lys Gly Leu
    50                  55                  60

Glu Trp Val Ala Ser Ile Ser Ser Gly Gly Thr Tyr Ile Tyr His Ala
65                  70                  75                  80

Asp Thr Leu Lys Gly Arg Phe Thr Ile Ser Arg Glu Asn Ala Lys Asn

```
            85                  90                  95
Thr Leu Tyr Leu Gln Met Thr Ser Leu Arg Ser Glu Asp Thr Ala Leu
            100                 105                 110

Tyr Tyr Cys Ala Arg Gly Pro Tyr His Ser Arg Tyr Ile Pro Tyr Leu
            115                 120                 125

Met Asp Ala Trp Gly Gln Gly Ala Ser Val Thr Val Ser Ser Ala Glu
            130                 135                 140

Thr Thr Ala Pro Ser Val Tyr Pro Leu Ala Pro Gly Thr Ala Leu Lys
145                 150                 155                 160

Ser Asn Ser Met Val Thr Leu Gly Cys Leu Val Lys Gly Tyr Phe Pro
                165                 170                 175

Glu Pro Val Thr Val Thr Trp Asn Ser Gly Ala Leu Ser Ser Gly Val
                180                 185                 190

His Thr Phe Pro Ala Val Leu Gln Ser Gly Leu Tyr Thr Leu Thr Ser
                195                 200                 205

Ser Val Thr Val Pro Ser Ser Thr Trp Pro Ser Gln Thr Val Thr Cys
210                 215                 220

Asn Val Ala His Pro Ala Ser Ser Thr Lys Val Asp Lys Lys Ile Val
225                 230                 235                 240

<210> SEQ ID NO 29
<211> LENGTH: 240
<212> TYPE: PRT
<213> ORGANISM: Rattus norvegicus

<400> SEQUENCE: 29

Met Ser Phe Ser Asn Thr Leu Val Phe Leu Leu Phe Leu Leu Lys Gly
1               5                   10                  15

Ile Leu Cys Glu Val Gln Leu Val Glu Ser Gly Gly Gly Leu Val Gln
                20                  25                  30

Pro Gly Arg Ser Leu Lys Leu Ser Cys Leu Val Ser Gly Phe Thr Phe
            35                  40                  45

Ser Asn Phe Gly Met Asn Trp Ile Arg Gln Ala Pro Gly Lys Gly Leu
50                  55                  60

Glu Trp Val Ala Ser Ile Ser Ser Gly Gly Thr Tyr Ile Tyr His Ala
65                  70                  75                  80

Asp Thr Leu Lys Gly Arg Phe Thr Ile Ser Arg Glu Asn Ala Lys Asn
                85                  90                  95

Thr Leu Tyr Leu Gln Met Thr Ser Leu Arg Ser Glu Asp Thr Ala Leu
            100                 105                 110

Tyr Tyr Cys Ala Arg Gly Pro Tyr His Ser Arg Tyr Ile Pro Tyr Leu
            115                 120                 125

Met Asp Ala Trp Gly Gln Gly Ala Ser Val Thr Val Ser Ser Ala Glu
            130                 135                 140

Thr Thr Ala Pro Ser Val Tyr Pro Leu Ala Pro Gly Thr Ala Leu Lys
145                 150                 155                 160

Ser Asn Ser Met Val Thr Leu Gly Cys Leu Val Lys Gly Tyr Phe Pro
                165                 170                 175

Glu Pro Val Thr Val Thr Trp Asn Ser Gly Ala Leu Ser Ser Gly Val
                180                 185                 190

His Thr Phe Pro Ala Val Leu Gln Ser Gly Leu Tyr Thr Leu Thr Ser
                195                 200                 205

Ser Val Thr Val Pro Ser Ser Thr Trp Pro Ser Gln Thr Val Thr Cys
210                 215                 220
```

Asn Val Ala His Pro Ala Ser Ser Thr Lys Val Asp Lys Lys Ile Val
225                 230                 235                 240

<210> SEQ ID NO 30
<211> LENGTH: 240
<212> TYPE: PRT
<213> ORGANISM: Rattus norvegicus

<400> SEQUENCE: 30

Met Ser Phe Ser Asn Thr Leu Val Phe Leu Leu Phe Leu Leu Lys Gly
1               5                   10                  15

Ile Leu Cys Glu Val Gln Leu Val Glu Ser Gly Gly Gly Leu Val Gln
                20                  25                  30

Pro Gly Arg Ser Leu Lys Leu Ser Cys Leu Val Ser Gly Phe Thr Phe
            35                  40                  45

Ser Asn Phe Gly Met Asn Trp Ile Arg Gln Ala Pro Gly Lys Gly Leu
    50                  55                  60

Glu Trp Val Ala Ser Ile Ser Ser Gly Gly Thr Tyr Ile Tyr His Ala
65                  70                  75                  80

Asp Thr Leu Lys Gly Arg Phe Thr Ile Ser Arg Glu Asn Ala Lys Asn
                85                  90                  95

Thr Leu Tyr Leu Gln Met Thr Ser Leu Arg Ser Glu Asp Thr Ala Leu
            100                 105                 110

Tyr Tyr Cys Ala Arg Gly Pro Tyr His Ser Arg Tyr Ile Pro Tyr Leu
        115                 120                 125

Met Asp Ala Trp Gly Gln Gly Ala Ser Val Thr Val Ser Ser Ala Glu
    130                 135                 140

Thr Thr Ala Pro Ser Val Tyr Pro Leu Ala Pro Gly Thr Ala Leu Lys
145                 150                 155                 160

Ser Asn Ser Met Val Thr Leu Gly Cys Leu Val Lys Gly Tyr Phe Pro
                165                 170                 175

Glu Pro Val Thr Val Thr Trp Asn Ser Gly Ala Leu Ser Ser Gly Val
            180                 185                 190

His Thr Phe Pro Ala Val Leu Gln Ser Gly Leu Tyr Thr Leu Thr Ser
        195                 200                 205

Ser Val Thr Val Pro Ser Ser Thr Trp Pro Ser Gln Thr Val Thr Cys
    210                 215                 220

Asn Val Ala His Pro Ala Ser Ser Thr Lys Val Asp Lys Lys Ile Val
225                 230                 235                 240

<210> SEQ ID NO 31
<211> LENGTH: 240
<212> TYPE: PRT
<213> ORGANISM: Rattus norvegicus

<400> SEQUENCE: 31

Met Ser Phe Ser Asn Thr Leu Val Phe Leu Leu Phe Leu Leu Lys Gly
1               5                   10                  15

Ile Leu Cys Glu Val Gln Leu Val Glu Pro Gly Gly Gly Leu Val Gln
                20                  25                  30

Pro Gly Arg Ser Leu Lys Leu Ser Cys Leu Val Ser Gly Phe Thr Phe
            35                  40                  45

Ser Asn Phe Gly Met Asn Trp Ile Arg Gln Ala Pro Gly Lys Gly Leu
    50                  55                  60

Glu Trp Val Ala Ser Ile Ser Ser Gly Gly Thr Tyr Ile Tyr His Ala
65                  70                  75                  80

```
Asp Thr Leu Lys Gly Arg Phe Thr Ile Ser Arg Glu Asn Ala Lys Asn
                85                  90                  95
Thr Leu Tyr Leu Gln Met Thr Ser Leu Arg Ser Glu Asp Thr Ala Leu
            100                 105                 110
Tyr Tyr Cys Ala Arg Gly Pro Tyr His Ser Arg Tyr Ile Pro Tyr Leu
        115                 120                 125
Met Asp Ala Trp Gly Gln Gly Ala Ser Val Thr Val Ser Ser Ala Glu
    130                 135                 140
Thr Thr Ala Pro Ser Val Tyr Pro Leu Ala Pro Gly Thr Ala Leu Lys
145                 150                 155                 160
Ser Ser Ser Met Val Thr Leu Gly Cys Leu Val Lys Gly Tyr Phe Pro
                165                 170                 175
Glu Pro Val Thr Val Thr Trp Asn Ser Gly Ala Leu Ser Ser Gly Val
            180                 185                 190
His Thr Phe Pro Ala Val Leu Gln Ser Gly Leu Tyr Thr Leu Thr Ser
        195                 200                 205
Ser Val Thr Val Pro Ser Ser Thr Trp Pro Ser Gln Thr Val Thr Cys
    210                 215                 220
Asn Val Ala His Pro Ala Ser Ser Thr Lys Val Asp Lys Lys Ile Val
225                 230                 235                 240

<210> SEQ ID NO 32
<211> LENGTH: 240
<212> TYPE: PRT
<213> ORGANISM: Rattus norvegicus

<400> SEQUENCE: 32

Met Ser Phe Ser Asn Thr Leu Val Phe Leu Leu Phe Leu Leu Lys Gly
1               5                   10                  15
Ile Leu Cys Glu Val Gln Leu Val Glu Ser Gly Gly Gly Leu Val Gln
                20                  25                  30
Pro Gly Arg Ser Leu Lys Leu Ser Cys Leu Val Ser Gly Phe Thr Phe
            35                  40                  45
Ser Asn Phe Gly Met Asn Trp Ile Arg Gln Ala Pro Gly Lys Gly Leu
        50                  55                  60
Glu Trp Val Ala Ser Ile Ser Ser Gly Gly Thr Tyr Ile Tyr His Ala
65                  70                  75                  80
Asp Thr Leu Lys Gly Arg Phe Thr Ile Ser Arg Glu Asn Ala Lys Asn
                85                  90                  95
Thr Leu Tyr Leu Gln Met Thr Ser Leu Arg Ser Glu Asp Thr Ala Leu
            100                 105                 110
Tyr Tyr Cys Ala Arg Gly Pro Tyr His Ser Arg Tyr Ile Pro Tyr Leu
        115                 120                 125
Met Asp Ala Trp Gly Gln Gly Ala Ser Val Thr Val Ser Ser Ala Glu
    130                 135                 140
Thr Thr Val Pro Ser Val Tyr Pro Leu Ala Pro Gly Thr Ala Leu Lys
145                 150                 155                 160
Ser Asn Ser Met Val Thr Leu Gly Cys Leu Val Lys Gly Tyr Phe Pro
                165                 170                 175
Glu Pro Val Thr Val Thr Trp Asn Ser Gly Ala Leu Ser Ser Gly Val
            180                 185                 190
His Thr Phe Pro Ala Val Leu Gln Ser Gly Leu Tyr Thr Leu Thr Ser
        195                 200                 205
Ser Val Thr Val Pro Ser Ser Thr Trp Pro Ser Gln Thr Val Thr Cys
    210                 215                 220
```

```
Asn Val Ala His Pro Ala Ser Ser Thr Lys Val Asp Lys Ile Val
225                 230                 235                 240

<210> SEQ ID NO 33
<211> LENGTH: 98
<212> TYPE: PRT
<213> ORGANISM: Artificial Sequence
<220> FEATURE:
<223> OTHER INFORMATION: Synthetic

<400> SEQUENCE: 33

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val

<210> SEQ ID NO 34
<211> LENGTH: 98
<212> TYPE: PRT
<213> ORGANISM: Artificial Sequence
<220> FEATURE:
<223> OTHER INFORMATION: Synthetic

<400> SEQUENCE: 34

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val

<210> SEQ ID NO 35
<211> LENGTH: 98
<212> TYPE: PRT
<213> ORGANISM: Artificial Sequence
<220> FEATURE:
<223> OTHER INFORMATION: Synthetic

<400> SEQUENCE: 35

Ala Glu Thr Thr Ala Pro Ser Val Tyr Pro Leu Ala Pro Gly Thr Ala
1               5                   10                  15

Leu Lys Ser Asn Ser Met Val Thr Leu Gly Cys Leu Val Lys Gly Tyr
            20                  25                  30
```

Phe Pro Glu Pro Val Thr Val Thr Trp Asn Ser Gly Ala Leu Ser Ser
                35                  40                  45

Gly Val His Thr Phe Pro Ala Val Leu Gln Ser Gly Leu Tyr Thr Leu
    50                  55                  60

Thr Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val

<210> SEQ ID NO 36
<211> LENGTH: 98
<212> TYPE: PRT
<213> ORGANISM: Artificial Sequence
<220> FEATURE:
<223> OTHER INFORMATION: Synthetic

<400> SEQUENCE: 36

Ala Glu Thr Thr Ala Pro Ser Val Tyr Pro Leu Ala Pro Gly Thr Ala
1               5                   10                  15

Leu Lys Ser Asn Ser Met Val Thr Leu Gly Cys Leu Val Lys Gly Tyr
                20                  25                  30

Phe Pro Glu Pro Val Thr Val Thr Trp Asn Ser Gly Ala Leu Ser Ser
                35                  40                  45

Gly Val His Thr Phe Pro Ala Val Leu Gln Ser Gly Leu Tyr Thr Leu
    50                  55                  60

Thr Ser Ser Val Thr Val Pro Ser Ser Thr Trp Ser Ser Gln Ala Val
65                  70                  75                  80

Thr Cys Asn Val Ala His Pro Ala Ser Ser Thr Lys Val Asp Lys Lys
                85                  90                  95

Ile Val

<210> SEQ ID NO 37
<211> LENGTH: 240
<212> TYPE: PRT
<213> ORGANISM: Rattus norvegicus

<400> SEQUENCE: 37

Met Gly Val Pro Thr Gln Leu Leu Gly Leu Leu Leu Leu Trp Ile Thr
1               5                   10                  15

Asp Ala Ile Cys Asp Ile Gln Met Thr Gln Ser Pro Gly Ser Leu Cys
                20                  25                  30

Ala Ser Leu Gly Glu Thr Val Thr Ile Glu Cys Arg Ala Ser Asp Asp
                35                  40                  45

Ile Tyr Ser Asn Leu Ala Trp Tyr Gln Gln Lys Pro Gly Asn Ser Pro
    50                  55                  60

Gln Leu Leu Ile Phe Asp Gly Asn Arg Leu Ala Asp Gly Val Pro Ser
65                  70                  75                  80

Arg Phe Ser Gly Ser Gly Ser Gly Thr Gln Tyr Ser Leu Lys Met Lys
                85                  90                  95

Ser Leu Gln Phe Glu Asp Val Ala Ser Tyr Phe Cys Gln Gln Tyr Asn
                100                 105                 110

Asn Tyr Pro Leu Thr Phe Gly Ser Gly Thr Lys Leu Glu Ile Lys Arg
            115                 120                 125

Ala Asp Ala Ala Pro Thr Val Ser Ile Phe Pro Pro Ser Met Glu Gln
        130                 135                 140

```
Leu Thr Ser Gly Gly Ala Thr Val Val Cys Phe Val Asn Asn Phe Tyr
145                 150                 155                 160

Pro Arg Asp Ile Ser Val Lys Trp Lys Ile Asp Gly Ser Glu Gln Arg
            165                 170                 175

Asp Gly Val Leu Asp Ser Val Thr Asp Gln Asp Ser Lys Asp Ser Thr
            180                 185                 190

Tyr Ser Met Ser Ser Thr Leu Ser Leu Thr Lys Val Glu Tyr Glu Arg
        195                 200                 205

His Asn Leu Tyr Thr Cys Glu Val Val His Lys Thr Ser Ser Ser Pro
    210                 215                 220

Val Val Lys Ser Phe Asn Arg Asn Glu Lys Gly Glu Phe Gln His Thr
225                 230                 235                 240
```

<210> SEQ ID NO 38
<211> LENGTH: 240
<212> TYPE: PRT
<213> ORGANISM: Rattus norvegicus

<400> SEQUENCE: 38

```
Met Gly Val Pro Thr Gln Leu Leu Gly Leu Leu Leu Leu Trp Ile Thr
1               5                   10                  15

Asp Ala Ile Cys Asp Ile Gln Met Thr Gln Ser Pro Gly Ser Leu Cys
            20                  25                  30

Ala Ser Leu Gly Glu Thr Val Thr Ile Glu Cys Arg Ala Ser Asp Asp
        35                  40                  45

Ile Tyr Ser Asn Leu Ala Trp Tyr Gln Gln Lys Pro Gly Asn Ser Pro
    50                  55                  60

Gln Leu Leu Ile Phe Asp Gly Asn Arg Leu Ala Asp Gly Val Pro Ser
65                  70                  75                  80

Arg Phe Ser Gly Ser Gly Ser Gly Thr Gln Tyr Ser Leu Lys Met Lys
                85                  90                  95

Ser Leu Gln Phe Glu Asp Val Ala Ser Tyr Phe Cys Gln Gln Tyr Asn
            100                 105                 110

Asn Tyr Pro Leu Thr Phe Gly Ser Gly Thr Lys Leu Glu Ile Lys Arg
        115                 120                 125

Ala Asp Ala Ala Pro Thr Val Ser Ile Phe Pro Pro Ser Met Glu Gln
    130                 135                 140

Leu Thr Ser Gly Gly Ala Thr Val Val Cys Phe Val Asn Asn Phe Tyr
145                 150                 155                 160

Pro Arg Asp Ile Ser Val Lys Trp Lys Ile Asp Gly Ser Glu Gln Arg
            165                 170                 175

Asp Gly Val Leu Asp Ser Val Thr Asp Gln Asp Ser Lys Asp Gly Thr
            180                 185                 190

Tyr Ser Met Ser Ser Thr Leu Ser Leu Thr Lys Val Glu Tyr Glu Arg
        195                 200                 205

His Asn Leu Tyr Thr Cys Glu Val Val His Lys Thr Ser Ser Ser Pro
    210                 215                 220

Val Val Lys Ser Phe Asn Arg Asn Glu Lys Gly Glu Phe Gln His Thr
225                 230                 235                 240
```

<210> SEQ ID NO 39
<211> LENGTH: 223
<212> TYPE: PRT
<213> ORGANISM: Rattus norvegicus

<400> SEQUENCE: 39

```
Met Gly Val Pro Thr Gln Leu Leu Gly Leu Leu Leu Trp Ile Thr
1               5                   10                  15

Asp Ala Ile Cys Asp Ile Gln Met Thr Gln Ser Pro Gly Ser Leu Cys
            20                  25                  30

Ala Ser Leu Gly Glu Thr Val Thr Ile Glu Cys Arg Ala Ser Asp Asp
        35                  40                  45

Ile Tyr Ser Asn Leu Ala Trp Tyr Gln Gln Lys Pro Gly Asn Ser Pro
    50                  55                  60

Gln Leu Leu Ile Phe Asp Gly Asn Arg Leu Ala Asp Gly Val Pro Ser
65                  70                  75                  80

Arg Phe Ser Gly Ser Gly Ser Gly Thr Gln Tyr Ser Leu Lys Met Lys
                85                  90                  95

Ser Leu Gln Phe Glu Asp Val Ala Ser Tyr Phe Cys Gln Gln Tyr Asn
            100                 105                 110

Asn Tyr Pro Leu Thr Phe Gly Ser Gly Thr Lys Leu Glu Ile Lys Arg
        115                 120                 125

Ala Asp Ala Ala Pro Thr Val Ser Ile Phe Pro Pro Ser Met Glu Gln
130                 135                 140

Leu Thr Ser Gly Gly Ala Thr Val Val Cys Phe Val Asn Asn Phe Tyr
145                 150                 155                 160

Pro Arg Asp Ile Ser Val Lys Trp Lys Ile Asp Gly Ser Glu Gln Arg
                165                 170                 175

Asp Gly Val Leu Asp Ser Val Thr Asp Gln Asp Ser Lys Asp Ser Thr
            180                 185                 190

Tyr Ser Met Ser Ser Thr Leu Ser Leu Thr Lys Val Glu Tyr Glu Arg
        195                 200                 205

His Asn Leu Tyr Thr Cys Glu Val Val His Lys Thr Ser Phe Ser
210                 215                 220

<210> SEQ ID NO 40
<211> LENGTH: 240
<212> TYPE: PRT
<213> ORGANISM: Rattus norvegicus

<400> SEQUENCE: 40

Met Gly Val Pro Thr Gln Leu Leu Gly Leu Leu Leu Trp Ile Thr
1               5                   10                  15

Asp Ala Ile Cys Asp Ile Gln Met Thr Gln Ser Pro Gly Ser Leu Cys
            20                  25                  30

Ala Ser Leu Gly Glu Thr Val Thr Ile Glu Cys Arg Ala Ser Asp Asp
        35                  40                  45

Ile Tyr Ser Asn Leu Ala Trp Tyr Gln Gln Lys Pro Gly Asn Ser Pro
    50                  55                  60

Gln Leu Leu Ile Phe Asp Gly Asn Arg Leu Ala Asp Gly Val Pro Ser
65                  70                  75                  80

Arg Phe Ser Gly Ser Gly Ser Gly Thr Gln Tyr Ser Leu Lys Met Lys
                85                  90                  95

Ser Leu Gln Phe Glu Asp Val Ala Ser Tyr Phe Cys Gln Gln Tyr Asn
            100                 105                 110

Asn Tyr Pro Leu Thr Phe Gly Ser Gly Thr Lys Leu Glu Ile Lys Arg
        115                 120                 125

Ala Asp Ala Ala Pro Thr Val Ser Ile Phe Pro Pro Ser Met Glu Gln
130                 135                 140

Leu Thr Ser Gly Gly Ala Thr Val Val Cys Phe Val Asn Asn Phe Tyr
```

```
                    145                 150                 155                 160

Pro Arg Asp Ile Ser Val Lys Trp Lys Ile Asp Gly Ser Glu Gln Arg
                165                 170                 175

Asp Gly Val Leu Asp Ser Val Thr Asp Gln Asp Ser Lys Asp Ser Thr
                180                 185                 190

Tyr Ser Met Ser Ser Thr Leu Ser Leu Thr Lys Val Glu Tyr Glu Arg
                195                 200                 205

His Asn Leu Tyr Thr Cys Glu Val Val His Lys Thr Ser Ser Ser Pro
        210                 215                 220

Val Val Lys Ser Phe Asn Arg Asn Glu Lys Gly Glu Phe Gln His Thr
225                 230                 235                 240

<210> SEQ ID NO 41
<211> LENGTH: 108
<212> TYPE: PRT
<213> ORGANISM: Artificial Sequence
<220> FEATURE:
<223> OTHER INFORMATION: Synthetic

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asp Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Ser Gly Val Pro Ser Arg Phe Ser Gly
    50                  55                  60

Gly Gly Ser Gly Ala His Phe Thr Phe Thr Ile Ser Ser Leu Gln Pro
65                  70                  75                  80

Glu Asp Ile Ala Thr Tyr Tyr Cys Gln Gln Tyr Asp Tyr Leu Pro Trp
                85                  90                  95

Thr Phe Gly Gln Gly Thr Lys Val Glu Ile Lys Arg
            100                 105

<210> SEQ ID NO 42
<211> LENGTH: 108
<212> TYPE: PRT
<213> ORGANISM: Artificial Sequence
<220> FEATURE:
<223> OTHER INFORMATION: Synthetic

<400> SEQUENCE: 42

Asp Ile Gln Met Thr Gln Ser Pro Ser Pro Leu Ser Ala Ser Val Gly
1               5                   10                  15

Asp Ser Val Thr Ile Thr Cys Gln Ala Ser Gln Asp Ile Arg Asn Ser
            20                  25                  30

Leu Ile Trp Tyr Gln Gln Lys Pro Gly Lys Ala Pro Lys Phe Leu Ile
        35                  40                  45

Tyr Asp Ala Glu Asn Leu Glu Ile Gly Val Pro Ser Arg Phe Arg Gly
    50                  55                  60

Ser Gly Ser Gly Thr Asp Phe Ala Leu Ser Ile Ser Ser Leu Gln Pro
65                  70                  75                  80

Glu Asp Phe Ala Thr Tyr Tyr Cys Gln Gln Tyr Tyr Asn Leu Pro Tyr
                85                  90                  95

Thr Phe Gly Gln Gly Thr Lys Leu Glu Ile Lys Arg
            100                 105
```

-continued

```
<210> SEQ ID NO 43
<211> LENGTH: 115
<212> TYPE: PRT
<213> ORGANISM: Artificial Sequence
<220> FEATURE:
<223> OTHER INFORMATION: Synthetic

<400> SEQUENCE: 43

Met Ser Val Leu Thr Gln Val Leu Ala Leu Leu Leu Trp Leu Thr
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Gly Asn
            35                  40                  45

Ile His Asn Tyr Leu Ala Trp Tyr Gln Gln Lys Gln Gly Lys Ser Pro
        50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Ser Tyr Tyr Cys Gln His Phe Trp
            100                 105                 110

Ser Thr Pro
        115

<210> SEQ ID NO 44
<211> LENGTH: 108
<212> TYPE: PRT
<213> ORGANISM: Artificial Sequence
<220> FEATURE:
<223> OTHER INFORMATION: Synthetic

<400> SEQUENCE: 44

Asp Ile Gln Met Thr Gln Ser Pro Asp Tyr Leu Ser Ala Ser Val Gly
1               5                   10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
            35                  40                  45

Tyr Asp Ala Lys Thr Leu Val Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Ile Pro Phe
                85                  90                  95

Thr Phe Gly Ser Gly Thr Lys Leu Glu Ile Lys Arg
            100                 105

<210> SEQ ID NO 45
<211> LENGTH: 128
<212> TYPE: PRT
<213> ORGANISM: Artificial Sequence
<220> FEATURE:
<223> OTHER INFORMATION: Synthetic

<400> SEQUENCE: 45

Met Arg Thr Pro Ala Gln Phe Leu Gly Ile Leu Leu Leu Trp Phe Pro
1               5                   10                  15

Gly Ile Lys Cys Asp Ile Lys Met Thr Gln Ser Pro Ser Ser Met Tyr
```

```
                    20                  25                  30
Ala Ser Leu Gly Glu Arg Val Thr Ile Ser Cys Lys Ala Ser Gln Asp
                35                  40                  45
Ile Asn Ser Tyr Leu Thr Trp Phe Gln Gln Lys Pro Gly Lys Ser Pro
         50                  55                  60
Lys Thr Leu Leu Tyr Arg Ala Asn Arg Leu Val Asp Gly Val Pro Ser
 65                  70                  75                  80
Arg Phe Ser Gly Ser Gly Ser Gly Gln Asp Phe Ser Leu Thr Ile Ser
                 85                  90                  95
Ser Leu Glu Tyr Glu Asp Met Gly Ile Tyr Tyr Cys Leu Gln Tyr Asp
                100                 105                 110
Glu Phe Pro Leu Thr Phe Gly Ala Gly Thr Lys Leu Glu Leu Lys Arg
                115                 120                 125

<210> SEQ ID NO 46
<211> LENGTH: 106
<212> TYPE: PRT
<213> ORGANISM: Artificial Sequence
<220> FEATURE:
<223> OTHER INFORMATION: Synthetic

<400> SEQUENCE: 46

Ala Asp Ala Ala Pro Thr Val Ser Ile Phe Pro Pro Ser Thr Glu Gln
 1               5                  10                  15
Leu Ala Thr Gly Gly Ala Ser Val Val Cys Leu Met Asn Asn Phe Tyr
                20                  25                  30
Pro Arg Asp Ile Ser Val Lys Trp Lys Ile Asp Gly Thr Glu Arg Arg
                35                  40                  45
Asp Gly Val Leu Asp Ser Val Thr Asp Gln Asp Ser Lys Asp Ser Thr
         50                  55                  60
Tyr Ser Met Ser Ser Thr Leu Ser Leu Thr Lys Ala Asp Tyr Glu Ser
 65                  70                  75                  80
His Asn Leu Tyr Thr Cys Glu Val Val His Lys Thr Ser Ser Ser Pro
                 85                  90                  95
Val Val Lys Ser Phe Asn Arg Asn Glu Cys
                100                 105

<210> SEQ ID NO 47
<211> LENGTH: 106
<212> TYPE: PRT
<213> ORGANISM: Artificial Sequence
<220> FEATURE:
<223> OTHER INFORMATION: Synthetic

<400> SEQUENCE: 47

Ala Asp Ala Ala Pro Thr Val Ser Ile Phe Pro Pro Ser Met Glu Gln
 1               5                  10                  15
Leu Thr Ser Gly Gly Ala Thr Val Val Cys Phe Val Asn Asn Phe Tyr
                20                  25                  30
Pro Arg Asp Ile Ser Val Lys Trp Lys Ile Asp Gly Ser Glu Gln Arg
                35                  40                  45
Asp Gly Val Leu Asp Ser Val Thr Asp Gln Asp Ser Lys Asp Ser Thr
         50                  55                  60
Tyr Ser Met Ser Ser Thr Leu Ser Leu Thr Lys Val Glu Tyr Glu Arg
 65                  70                  75                  80
His Asn Leu Tyr Thr Cys Glu Val Val His Lys Thr Ser Ser Ser Pro
                 85                  90                  95
```

```
Val Val Lys Ser Phe Asn Arg Asn Glu Cys
            100                 105

<210> SEQ ID NO 48
<211> LENGTH: 106
<212> TYPE: PRT
<213> ORGANISM: Artificial Sequence
<220> FEATURE:
<223> OTHER INFORMATION: Synthetic

<400> SEQUENCE: 48

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
            35                  40                  45

Asn Gly Val Leu Asn Ser Trp Thr Asp Gln Asp Ser Lys Asp Ser Thr
            50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105
```